(12) United States Patent
Lemonnier et al.

(10) Patent No.: US 9,914,712 B2
(45) Date of Patent: Mar. 13, 2018

(54) ANTIBACTERIAL THIAZOLECARBOXYLIC ACIDS

(71) Applicant: ANTABIO SAS, Labege (FR)

(72) Inventors: Marc Lemonnier, Labege (FR); David Davies, Labege (FR); Thomas David Pallin, Harlow (GB)

(73) Assignee: ANTABIO SAS, Labege (FR)

( * ) Notice: Subject to any disclaimer, the term of this patent is extended or adjusted under 35 U.S.C. 154(b) by 0 days.

(21) Appl. No.: 14/897,811

(22) PCT Filed: Jun. 12, 2014

(86) PCT No.: PCT/EP2014/062281
§ 371 (c)(1),
(2) Date: Dec. 11, 2015

(87) PCT Pub. No.: WO2014/198849
PCT Pub. Date: Dec. 18, 2014

(65) Prior Publication Data
US 2016/0272601 A1    Sep. 22, 2016

(30) Foreign Application Priority Data
Jun. 13, 2013 (GB) .................................. 1310542.4

(51) Int. Cl.
| | | |
|---|---|---|
| *C07D 277/56* | (2006.01) | |
| *C07D 417/12* | (2006.01) | |
| *C07D 417/14* | (2006.01) | |
| *A61K 31/426* | (2006.01) | |
| *A61K 31/427* | (2006.01) | |
| *A61K 31/4439* | (2006.01) | |
| *A61K 31/454* | (2006.01) | |
| *A61K 31/4545* | (2006.01) | |
| *A61K 31/4709* | (2006.01) | |
| *A61K 31/506* | (2006.01) | |
| *A61K 31/5377* | (2006.01) | |
| *A61K 31/538* | (2006.01) | |
| *A61K 31/551* | (2006.01) | |
| *A61K 45/06* | (2006.01) | |

(52) U.S. Cl.
CPC .......... *C07D 277/56* (2013.01); *A61K 31/426* (2013.01); *A61K 31/427* (2013.01); *A61K 31/4439* (2013.01); *A61K 31/454* (2013.01); *A61K 31/4545* (2013.01); *A61K 31/4709* (2013.01); *A61K 31/506* (2013.01); *A61K 31/538* (2013.01); *A61K 31/5377* (2013.01); *A61K 31/551* (2013.01); *A61K 45/06* (2013.01); *C07D 417/12* (2013.01); *C07D 417/14* (2013.01)

(58) Field of Classification Search
CPC ... C07D 277/56; C07D 417/12; C07D 417/14
See application file for complete search history.

(56) References Cited

U.S. PATENT DOCUMENTS 6,936,629 B2 * 8/2005 Chan Chun Kong .................. C07D 277/56
514/365

FOREIGN PATENT DOCUMENTS

| EP | 0050965 A1 | 5/1985 |
|---|---|---|
| EP | 1321463 A1 | 6/2003 |
| EP | 3008045 A1 | 4/2016 |
| WO | 0076962 A1 | 12/2000 |
| WO | 2012088283 A1 | 6/2012 |
| WO | 2014198849 A1 | 12/2014 |

OTHER PUBLICATIONS

Adams, A., et al., "367. Thiazoles derived from Chrysean and isoChrysean." XP55054098, Journal of the Chemical Society, 1956, pp. 1870-1877.
Baskin, Jeremy M., et al., "A mild, convenient synthesis of sulfinic acid salts and sulfonamides from alkyl and aryl halides," Tetrahedron Letters, 2002, pp. 8479-8483, vol. 43, Elsevier Science Ltd.
Beling, C. Abbott, "The Treatment of Staphylococcic Infections with Thiazole Derivatives of Sulfanilamide," XP026427173, American Journal of Surgery, Aug. 1941, pp. 219-231, vol. 53, No. 2.
Borgianni, Luisa, et al. "Mutational Analysis of VIM-2 Reveals an Essential Determinant for Metallo-β-Lactamase Stability and Folding," Antimicrobial Agents and Chemotherapy, Aug. 2010, pp. 3197-3204, vol. 54, No. 8, American Society for Microbiology.
Certified United Kingdom Patent Application No. 1310542A filed on Jun. 13, 2013, 81 pages.

(Continued)

*Primary Examiner* — Laura L. Stockton
(74) *Attorney, Agent, or Firm* — Conley Rose, P.C.; Rodney B. Carroll

(57) ABSTRACT

Compounds of general formula (I):

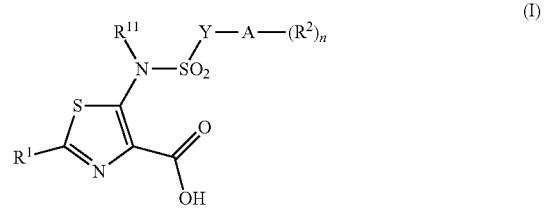

wherein $R^1$, $R^{11}$, Y, $R^2$, n and A are as defined herein are useful as inhibitors or metallo-β-lactamase (MBL) enzymes and can be used for reducing or removing antibiotic resistance in bacteria.

36 Claims, No Drawings

(56) References Cited

OTHER PUBLICATIONS

Faridoon, et al., 3-Mercapto-1,2,4-triazoles and N-acylated thiosemicarbazides as metallo-β-lactamase inhibitors, Bioorganic & Medicinal Chemistry Letters, 2012, pp. 380-386, vol. 22, Elsevier Ltd.
Foreign communication from a related counterpart application—International Search Report and Written Opinion, PCT/EP2014/062281, dated Sep. 22, 2014, 9 pages.
Foreign communication from a related counterpart application—International Preliminary Report on Patentability, PCT/EP2014/062281, dated Dec. 15, 2015, 6 pages.
Hu, Xiangdong, et al., "BCL-XL-Templated Assembly of Its Own Protein-Protein Interaction Modulator from Fragments Decorated with Thio Acids and Sulfonyl Azides," J. Am. Chem. Soc., 2008, pp. 13820-13821, vol. 130, No. 42, American Chemical Society.
Ishii, Yoshikazu, et al., "In Vitro Potentiation of Carbapenems with ME1071, a Novel Metallo-β-Lactamase Inhibitor, against Metallo-β-Lactamase-Producing Pseudomonas aeruginosa Clinical Isolates," Antimicrobial Agents and Chemotherapy, Sep. 2010, pp. 3625-3629, vol. 54, No. 9, American Society for Microbiology.
Laraki, Nezha, et al., "Biochemical Characterization of the Pseudomonas aeruginosa 101/1477 Metallo-βLactamase IMP-1 Produced by *Escherichia coli*," Antimicrobial Agents and Chemotherapy, Apr. 1999, pp. 902-906, vol. 43, No. 4, American Society for Microbiology.
Li, Jianqing, et al., "A Facile Synthesis of 1-Substituted Cyclopropylsulfonamides," Synlett, 2006, pp. 725-728, No. 5, Georg Thieme Verlag Stuttgart, New York.
Mollard, Claire, et al., "Thiomandelic Acid, a Broad Spectrum Inhibitor of Zinc β-Lactamases," The Journal of Biological Chemistry, 2001, pp. 45015-45023 plus 12 pages supplementary material and 1 page publishing information, vol. 276, No. 48, Issue of Nov. 30, The American Society for Biochemistry and Molecular Biology, Inc.
Paulekuhn, G. Steffen, et al., "Trends in Active Pharmaceutical Ingredient Salt Selection based on Analysis of the Orange Book Database," Journal of Medicinal Chemistry, 2007, pp. 6665-6672, vol. 50, No. 26, American Chemical Society.
Payne, David J., et al., "Identification of a Series of Tricyclic Natural Products as Potent Broad-Spectrum Inhibitors of Metallo-β-Lactamases," Antimicrobial Agents and Chemotherapy, Jun. 2002, pp. 1880-1886, vol. 46, No. 6, American Society for Microbiology.
Payne, David J., et aL, "Inhibition of Metallo-β-Lactamases by a Series of Mercaptoacetic Acid Thiol Ester Derivatives," Antimicrobial Agents and Chemotherapy, Jan. 1997, pp. 135-140, vol. 41. No. 1, American Society for Microbiology.
Siemann, Stefan, et al., "N-Arylsulfonyl Hydrazones as Inhibitors of IMP-1 Metallo-β-Lactamase," Antimicrobial Agents and Chemotherapy, Aug. 2002, pp. 2450-2457, vol. 46, No. 8, American Society for Microbiology.
Smith, Michael B., et al., "March's Advanced Organic Chemistry: Reactions, Mechanisms, and Structure," 2001, 1 page, Wiley & Sons, Inc. , copyright page only.
Toney, Jeffrey H., et al., "Succinic Acids as Potent Inhibitors of Plasmid-borne IMP-1 Metallo-β-lactamase," The Journal of Biological Chemistry, 2001, pp. 31913-31918 plus 1 page publishing informtion, vol. 276, No. 34, Issue of Aug. 24, The American Society for Biochemistry and Molecular Biology, Inc.
Wuts, Peter G. M., et al., "Greene's Protective Groups in Organic Synthesis," Fourth Edition, 2007, 1112 pages, John Wiley & Sons, Inc.
Yong, Dongeun, et al., "Characterization of a New Metallo-β-Lactamase Gene, blaNDM-1, and a Novel Erythromycin Esterase Gene Carried on a Unique Genetic Structure in Klebsiella pneumoniae Sequence Type 14 from India," Antimicrobial Agents and Chemotherapy, Dec. 2009, pp. 5046-5054, vol. 53, No. 12, American Society for Microbiology.
Yuriev, Elizabeth, et al., "Investigation of structure-activity relationships in a series of glibenclamide analogues," European Journal of Medicinal Chemistry, 2004. pp. 835-847, vol. 39, Elsevier SAS.
Foreign Communication from a related counterpart application—First Office Action of Chinese Application No. 2014800449998, dated Nov. 22, 2016, with English translation, 23 pages.

\* cited by examiner

ANTIBACTERIAL THIAZOLECARBOXYLIC ACIDS

CROSS-REFERENCE TO RELATED APPLICATIONS

This application is a filing under 35 U.S.C. 371 of International Application No. PCT/EP2014/062281 filed Jun. 12, 2014, entitled "Antibacterial Thiazolecarboxylic Acids," which claims priority to Great Britain Patent Application No. 1310542.4 filed Jun. 13, 2013, which applications are incorporated by reference herein in their entirety.

FIELD OF INVENTION

The present invention relates to novel compounds and their use as inhibitors of metallo-β-lactamase (MBL) enzymes. More particularly, the invention relates to thiazole-4-carboxylic acid derivatives.

BACKGROUND

Bacteria in both clinical and non-clinical settings are becoming increasingly resistant to conventional antibiotics, and this resistance is becoming a serious clinical and epidemiological problem for human health. In Gram-negative bacteria, resistance to antibiotics often arises from the production by the organism of β-lactamases, especially metallo-β-lactamases (MBL).

MBL are resistance determinants of increasing clinical relevance. In fact, because of their broad range, potent carbapenemase activity and resistance to inhibitors, these enzymes can confer resistance to almost all β-lactam antibiotics.

MBLs were first detected in the mid-1960s as carried by mobile DNA elements in species with only low pathogenic potential. However, genes encoding MBL spread among major Gram-negative bacteria during the 1990s and this has led to a health crisis arising from the international dissemination of carbapenem-resistant Enterobacteriaceae producing the VIM-type and NDM-type metallo-β-lactamases.

Functional features of these Enterobacteriaceae include potent carbapenemase activity and resistance to clinical β-lactamase inhibitors (clavulanate and sulfones). The activity against β-lactams differs between the different metallo-β-lactamases, and substrate specificity might vary from a narrow range (eg, the CphA metallo-β-lactamase of *Aeromonas hydrophila*), to an extended range (eg, the VIM-type metallo-β-lactamases, which can degrade almost all classes of β-lactams apart from the monobactams).

There are three major structural subclasses of MBL which share substantial internal diversity. Members of the different subclasses differ not only in their high degree of sequence diversity, but also in the structure of their active sites. In enzymes of subclasses B1 and B3, the active site contains two zinc ions; in members of subclass B2, the active site contains only one zinc ion.

Acquired metallo-β-lactamases have been detected in strains of Enterobacteriaceae, *Pseudomonas aeruginosa*, *Acinetobacter baumannii*, and other Gram-negative bacteria. Among acquired MBL, almost all the enzymes belong to subclass B1, which indicates an overall higher propensity for members of this subclass to be captured and spread with mobile genetic elements than for members of subclasses B2 and B3.

As an example, the subclass B1 comprises the IMP-type, the VIM-type, and the NDM-type enzymes.

The IMP-type enzymes, including IMP-1, were first detected in Japan in the late 1980s, and have since been reported worldwide in Enterobacteriaceae and in Gram-negative bacteria. The IMP-type enzymes have broad substrate specificity with a high affinity for cephalosporins and carbapenems, but they have little activity against Temocillin.

The VIM-type enzymes, including VIM-2, were first discovered in Europe in the late 1990s and have since been reported worldwide. VIM-type enzymes were initially detected in *P. aeruginosa* and in other Gram-negative bacteria, but have since emerged in Enterobacteriaceae, and have become a major problem in some settings. More than 20 different VIM allotypes are known, each with a defined geographical distribution except for VIM-1 and VIM-2, which share a broader distribution than the IMP-type enzymes. The VIM-type metallo-β-lactamases show even broader substrate specificities than the IMP-types, being able to hydrolyse 6-α-methoxy-penicillins. Furthermore, the VIM-type enzymes are unique in the metallo-β-lactamases in that they have a high affinity for carbapenems.

New Delhi metallo-β-lactamase 1 (NDM-1) is a novel metallo-β-lactamase identified initially in a patient hospitalized in New Delhi with an infection caused by *Klebsiella pneumoniae*. Subsequently, organisms in the Enterobacteriaceae family containing this new 3-lactamase have been found widely distributed throughout India, Pakistan, and Bangladesh and are now occurring in the United Kingdom and in many other countries. The New Delhi metallo-β-lactamase 1 (NDM-1) is a polypeptide of 158 amino acids in length (Accession number AB571289) capable of hydrolyzing a wide range of β-lactam antibiotics including penicillins, cephalosporins and carbapenem antibiotics that are a mainstay for the treatment of antibiotic-resistant bacterial infections. Therefore there is an urgent need for identifying new compounds for detecting and/or inhibiting MBL bacteria.

DETAILED DESCRIPTION OF THE INVENTION

The present invention is based on the surprising finding by the present inventors that the compounds of general formula (I) are capable of inhibiting MBLs, including NDM-1, and are therefore useful for use in combination with β-lactam antibiotics.

In a first aspect of the present invention there is provided a compound of general formula (I) including all polymorphs thereof:

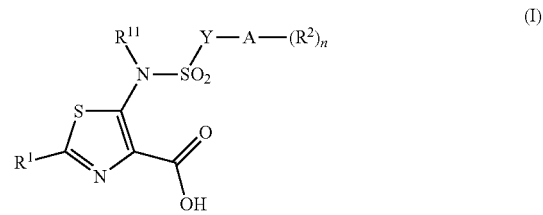

wherein
R$^1$ is hydrogen, halo, CN, R$^{12}$, OR$^{12}$, SR$^{12}$ or NR$^{12}$R$^{13}$
  wherein R$^{12}$ is C$_{1-6}$ alkyl optionally substituted with one or more substituent R$^a$; phenyl or 5- to 6-membered heteroaryl, either of which may optionally be substituted with one or more substituent R$^b$; or 3- to 6-membered cycloalkyl or 3- to 6-membered heterocyclyl, either of which is optionally substituted with one or more substituent $R^c$;

each $R^a$ is independently halo, CN, OH or $OC_{1-4}$ alkyl optionally substituted by one or more substituent selected from halo and OH;

each $R^b$ is independently halo, CN, OH or $C_{1-4}$ alkyl or $OC_{1-4}$ alkyl either of which may optionally substituted by one or more substituent selected from halo and OH;

each $R^c$ is independently halo, CN, OH, oxo or $C_{1-4}$ alkyl or $OC_{1-4}$ alkyl optionally substituted by one or more substituent selected from halo and OH;

$R^{13}$ is hydrogen or $C_{1-6}$ alkyl optionally substituted with one or more substituent $R^a$ as defined above;

Y is a single bond, $—C_{1-4}$ alkylene- or $—C_{2-4}$ alkenylene-, either of which may be substituted with a group $R^{17}$; or $—C_{1-4}$ alkylene-O—; $—C_{1-4}$ alkylene-N(R$^8$)—; $—N(R^8)—$; $—C_{1-4}$ alkylene-C(O)N(R$^8$)—; $—C_{1-4}$ alkylene-N(R$^8$)C(O)—$ or $—N(R^8)C_{1-4}$ alkylene-;

wherein $R^{17}$ is $OR^l$, $NR^lR^m$, $NR^lC(O)R^m$, $C(O)NR^lR^m$, $C(O)OR^m$;

each $R^l$ and $R^m$ is independently H or $C_{1-4}$ alkyl;

and $R^8$ is hydrogen or $C_{1-6}$ alkyl or $—C(O)C_{1-6}$ alkyl either of which is optionally substituted by one or more substituent $R^d$; and $C_{1-4}$ alkylene chains may optionally be substituted with one or more substituents $R^e$;

each $R^d$ and $R^e$ is independently halo, CN, OH or $OC_{1-4}$ alkyl optionally substituted by one or more substituent selected from halo and OH;

A represents a cyclic group selected from a 6- to 10-membered aryl, 5- to 10-membered heteroaryl or a 3- to 10-membered carbocyclyl or heterocyclyl group;

n is 0 to 4;

each $R^2$ is independently selected from $R^3$; or $C_{1-4}$ alkyl, $C_{2-4}$ alkenyl, $O(C_{1-4}$alkyl), $S(C_{1-4}$ alkyl), $SO(C_{1-4}$ alkyl) or $SO_2(C_{1-4}$ alkyl), any of which may optionally be substituted with one or more substituent $R^3$; or $C(O)OR^6$; $C(O)R^6$; $OR^5$, $NR^4R^5$; $NR^4C(O)R^6$, $NR^4C(O)NR^5R^6$ or $SO_2NR^{21}R^{22}$ or when A is saturated or partially saturated, $R^2$ may also be oxo;

each $R^3$ is independently halo, nitro, CN, OH; or $—C(O)OR^{14}$, $—C(O)NR^{14}R^{15}$ or $—NR^{14}R^{15}$; or phenyl optionally substituted with one or more substituent $R^7$; or naphthyl optionally substituted with one or more substituent $R^7$; or 5- to 10-membered heteroaryl optionally substituted with one or more substituent $R^7$; or 3- to 8-membered carbocyclyl optionally substituted with one or more substituent $R^7$; or 3- to 8-membered heterocyclyl optionally substituted with one or more substituent selected from oxo and $R^7$;

each of $R^{14}$ and $R^{15}$ is independently H, or $C_{1-6}$ alkyl optionally substituted with one or more substituents selected from halo and OH;

each $R^7$ is independently halo, CN, OH; or $C_{1-4}$ alkyl or $OC_{1-4}$ alkyl either of which may optionally substituted by one or more substituent selected from halo and OH; or $NR^jR^k$, wherein each $R^j$ and $R^k$ is independently H or $C_{1-4}$ alkyl;

each of $R^{21}$ and $R^{22}$ is hydrogen or $C_{1-4}$ alkyl or $R^{21}$ and $R^{22}$ together with the nitrogen atom to which they are attached may form a 5- or 6-membered heterocyclic ring, optionally containing one further heteroatom selected from N, O and S and optionally substituted with $C_{1-4}$ alkyl or halo;

$R^4$ is hydrogen or $C_{1-6}$ alkyl optionally substituted with halo, CN, OH, $NR^jR^k$; or $OC_{1-4}$ alkyl which may optionally substituted by one or more substituent selected from halo and OH;

wherein each $R^j$ and $R^k$ is independently H or $C_{1-4}$ alkyl;

$R^5$ is hydrogen, phenyl, 5- to 6-membered heteroaryl, 3- to 8-membered carbocyclyl or 3- to 8-membered heterocyclyl; or $C_{1-6}$ alkyl optionally substituted with phenyl, 5- to 6-membered heteroaryl, 3- to 8-membered carbocyclyl or 3- to 8-membered heterocyclyl;

wherein phenyl and heteroaryl groups are optionally substituted by one or more substituent $R^f$ and carbocyclyl and heterocyclyl groups are optionally substituted by one or more substituent $R^g$ and wherein:

each $R^f$ is independently halo, CN, OH or $C_{1-4}$ alkyl or $OC_{1-4}$ alkyl either of which may optionally be substituted by one or more substituent selected from halo and OH;

each $R^g$ is independently halo, CN, OH, oxo or $C_{1-4}$ alkyl or $OC_{1-4}$ alkyl optionally substituted by one or more substituent selected from halo and OH;

$R^6$ is $C_{1-6}$ alkyl optionally substituted with one or more $R^h$, or phenyl or 5- to 6-membered heteroaryl either of which is optionally substituted with one or more substituent $R^i$;

each $R^h$ is independently halo, CN, OH, $NH_2$, phenyl, pyridyl, COOH or $OC_{1-4}$ alkyl optionally substituted by one or more substituent selected from halo and OH;

each $R^i$ is independently halo, CN, OH, $NH_2$ or $C_{1-4}$ alkyl or $OC_{1-4}$ alkyl either of which may optionally be substituted by one or more substituent selected from halo and OH;

$R^{11}$ is hydrogen, $C_{1-4}$ alkyl optionally substituted by halo or benzyl optionally substituted by halo;

or a salt thereof, provided that the compound is not 5-(4-aminophenylsulfonamido)thiazole-4-carboxylic acid.

As explained above, the present inventors have found that, surprisingly, compounds of general formula (I) are capable of inhibiting MBLs, including NDM-1, and are therefore useful for use in combination with β-lactam antibiotics. A variety of compounds have been used as inhibitors of metallo β-lactamase enzymes. For example heteroaromatic thiols (Faridoon, H. et al, *Bioorg Med Chem Letts*, (2012), 22, 380); aliphatic thiols (WO 00/76962, Molland, C. et al, *J Biol Chem*, (2001), 276, 45015 and Payne, D. J. et al, *Antimicrobial Agents and Chemotherapy*, (1997), 41, 135); hydrazones (Siemann, S. et al, *Antimicrobial Agents and Chemotherapy*, (2002), 46, 2450); maleic acid derivatives (Ishii, Y. et al, *Antimicrobial Agents and Chemotherapy*, (2010), 54, 3625); succinic acid derivatives (Toney, J. H. et al, *J. Biol. Chem.* (2001), 276, 319); natural products (Payne, D. J. et al, *Antimicrobial Agents and Chemotherapy*, (2002), 46, 1880). However, the compounds described in these documents are very different in structure from the compounds of the present invention.

In the present invention, references to compounds of general formula (I) includes amorphous and crystalline forms, including all polymorphs, as well as isotopic variants, for example compounds of formula (I) in which one or more hydrogen atoms is replaced by deuterium, one or more carbon atoms is replaced by $^{14}C$ or one or more nitrogen atoms is replaced by $^{15}N$.

In the present specification "$C_{1-6}$ alkyl" refers to a straight or branched saturated hydrocarbon chain having one to six carbon atoms. Examples include methyl, ethyl, n-propyl, isopropyl, t-butyl and n-hexyl.

The term "$C_{1-4}$ alkyl" has a similar meaning to the above except that it refers to a straight or branched saturated hydrocarbon chain having one to four carbon atoms.

The term "haloalkyl" refers to an alkyl group substituted with one or more halogen atoms, up to perhalo substitution. Examples include trifluoromethyl and 2,2,2-trichloroethyl.

"$C_{1-4}$ alkylene" refers to a straight or branched hydrocarbon linking group having from one to four carbon atoms. Examples include —CH$_2$—, —CH$_2$CH$_2$—, —CH$_2$CH$_2$CH$_2$CH$_2$, —CH(CH$_3$)— and —CH(CH$_2$CH$_3$)—.

"$C_{2-4}$ alkenyl" refers to a straight or branched hydrocarbon chain containing at least one carbon-carbon double bond and having two to four carbon atoms. Examples include ethenyl, propen-1-yl and propen-2-yl.

"$C_{2-4}$ alkenylene" refers to a straight or branched hydrocarbon linking group having from two to four carbon atoms and at least one carbon-carbon double bond. Examples include —CH=CH— and —CH(CH$_2$CH=CH)—.

In the present specification "3- to 10-membered carbocyclyl" refers to a non-aromatic cyclic group having three to ten ring atoms, which may be fully or partially saturated and which may be fused or bridged. Examples include cycloalkyl groups such as cyclopropyl, cyclopentyl and cyclohexyl as well as cycloalkenyl groups such as cyclopentenyl and cyclohexenyl. Further examples include fused or bridged ring systems such as norbornane.

The term "3- to 10-membered heterocyclyl" refers to a cyclic group as defined above for 3- to 10-membered carbocyclyl, except that one or more ring atoms is replaced by a hetero atom selected from N, O and S. Examples include aziridine, azetidine, pyrrolidine, imidazoline, piperidine, piperazine, morpholine, oxetane, tetrahydrofuran and oxazoline. Further examples include fused or bridged ring systems such as octahydroquinoline or nor-tropane.

The term "6- to 10-membered aryl" in the context of the present specification refers to a ring system with aromatic character having from 6 to 10 ring carbon atoms and containing one ring or two fused rings. Where an aryl group contains more than one ring, not all rings must be fully aromatic in character. Examples of aromatic moieties are benzene, naphthalene, tetrahydronaphthalene, indane and indene.

The term "5- to 10-membered heteroaryl" in the context of the specification refers to a ring system with aromatic character having from 5 to 10 ring atoms, at least one of which is a heteroatom selected from N, O and S, and containing one ring or two fused rings. Where a heteroaryl group contains more than one ring, not all rings must be fully aromatic in character. Examples of monocyclic heteroaryl groups include pyridine, pyrimidine, furan, thiophene, pyrrole, pyrazole, imidazole, oxazole, isoxazole, thiazole and isothiazole. Examples of bicyclic fully aromatic heteroaryl groups include quinoline, isoquinoline, indole, benzofuran, benzimidazole and benzothiazole. Examples of bicyclic heteroaryl groups in which one ring is not fully aromatic in character include dihydroquinolines, tetrahydroquinoline, tetrahydroisoquinoline, dihydro-1,4-benzoxazine, chromene, chromane, benzimidazoline, benzomorpholine, isoindoline and indoline.

Other terms are to be construed in a similar manner, for example, the term "5- to 6-membered heteroaryl" refers to a monocyclic heteroaryl group having 5 or 6 ring atoms.

In the present specification, "halo" refers to fluoro, chloro, bromo or iodo.

The term "oxo" refers to an oxygen atom attached via a double bond to a ring carbon atom of a fully or partially unsaturated carbocyclic or heterocyclic ring. Oxo is also represented herein as "=O" or "(O)".

Salts of the compounds of general formula (I) may be pharmaceutically or veterinarily acceptable salts. Such salts include basic addition salts such as sodium, potassium, calcium, aluminium, zinc, magnesium and other metal salts as well as choline, diethanolamine, ethanolamine, ethyl diamine, meglumine and other well-known basic addition salts as summarised in Paulekuhn et al., (2007) *J. Med. Chem.* 50: 6665-6672 and/or known to those skilled in the art.

Where appropriate, pharmaceutically or veterinarily acceptable salts may also include salts of organic acids, especially carboxylic acids, including but not limited to acetate, trifluoroacetate, lactate, gluconate, citrate, tartrate, maleate, malate, pantothenate, adipate, alginate, aspartate, benzoate, butyrate, digluconate, cyclopentanate, glucoheptanate, glycerophosphate, oxalate, heptanoate, hexanoate, fumarate, nicotinate, pamoate, pectinate, 3-phenylpropionate, picrate, pivalate, proprionate, tartrate, lactobionate, pivolate, camphorate, undecanoate and succinate, organic sulfonic acids such as methanesulfonate, ethanesulfonate, 2-hydroxyethane sulfonate, camphorsulfonate, 2-naphthalenesulfonate, benzenesulfonate, p-chlorobenzenesulfonate and p-toluenesulfonate; and inorganic acids such as hydrochloride, hydrobromide, hydroiodide, sulfate, bisulfate, hemisulfate, thiocyanate, persulfate, phosphoric and sulfonic acids.

Salts are suitably those which are pharmaceutically or veterinarily acceptable. However, salts which are not pharmaceutically or veterinarily acceptable may still be valuable as intermediates.

In certain embodiments, compounds in which $R^1$ is methyl are excluded from the scope of general formula (I).

In certain embodiments, compounds in which $R^1$ is $C_{1-6}$ alkyl are excluded from the scope of general formula (I).

In certain embodiments, the following compounds are excluded from the scope of general formula (I):
5-{[(4-chlorophenyl)methyl]sulfonamido}-2-methyl-1,3-thiazole-4-carboxylic acid;
2-methyl-5-(quinoline-8-sulfonamido)-1,3-thiazole-4-carboxylic acid;
5-benzenesulfonamido-2-methyl-1,3-thiazole-4-carboxylic acid;
5-{[(3,5-dichlorophenyl)methyl]sulfonamido}-2-methyl-1,3-thiazole-4-carboxylic acid;
5-{[(2-chlorophenyl)methyl]sulfonamido}-2-methyl-1,3-thiazole-4-carboxylic acid; and
2-methyl-5-[(2,4,6-trimethylphenyl)sulfonamido]-1,3-thiazole-4-carboxylic acid.

In certain embodiments, compounds in which $R^1$ is phenyl or 5- to 6-membered heteroaryl are excluded from the scope of general formula (I).

In certain compounds of general formula (I):
Y is a single bond, —$C_{1-4}$ alkylene, —$C_{1-4}$ alkylene-O—, —$C_{1-4}$ alkylene-N($R^8$)—, —N($R^8$)—, —$C_{1-4}$ alkylene-C(O)N($R^8$)—, —$C_{1-4}$ alkylene-N($R^8$)C(O)— or —N($R^8$)$C_{1-4}$ alkylene-;
wherein $R^8$ is hydrogen or $C_{1-6}$ alkyl optionally substituted by one or more substituent $R^d$; and C$_{1-4}$ alkylene chains may optionally be substituted with one or more substituents R$^e$;
each R$^2$ is independently selected from R$^3$; or
C$_{1-4}$ alkyl, C$_{2-4}$ alkenyl, O(C$_{1-4}$ alkyl), S(C$_{1-4}$ alkyl), SO(C$_{1-4}$ alkyl) or SO$_2$(C$_{1-4}$ alkyl), any of which may optionally be substituted with one or more substituent R$^3$; or
C(O)OR$^6$; C(O)R$^6$; NR$^4$R$^5$ or NR$^4$C(O)R$^6$;
when R$^2$ is C(O)OR$^6$, R$^6$ may be hydrogen or C$_{1-6}$ alkyl optionally substituted with halo, CN, OH, or OC$_{1-4}$ alkyl which may optionally substituted by one or more substituent selected from halo and OH;
when R$^2$ is C(O)R$^6$, R$^6$ may be phenyl or 5-6-membered heteroaryl or C$_{1-6}$ alkyl optionally substituted with phenyl, wherein phenyl and heteroaryl groups may optionally be substituted with one or more substituent selected from halo, CN, OH or C$_{1-4}$ alkyl or OC$_{1-4}$ alkyl either of which may optionally be substituted by one or more substituent selected from halo and OH;
when R$^2$ is NR$^4$R$^5$ or NR$^4$C(O)R$^6$; R$^4$ may be hydrogen or C$_{1-6}$ alkyl optionally substituted with halo, CN, OH, or OC$_{1-4}$ alkyl which may optionally substituted by one or more substituent selected from halo and OH; and R$^6$ may be C$_{1-6}$ alkyl optionally substituted with one or more substituent selected from halo, CN, OH or OC$_{1-4}$ alkyl optionally substituted by one or more substituent selected from halo and OH; or R$^6$ may be or phenyl or 5- to 6-membered heteroaryl either of which is optionally substituted with one or more substituent selected from halo, CN, OH or OC$_{1-4}$ alkyl optionally substituted by one or more substituent selected from halo and OH; when R$^3$ is a cyclic group optionally substituted with one or more substituent R$^7$, each R$^7$ may be independently halo, CN, OH; or C$_{1-4}$ alkyl or OC$_{1-4}$ alkyl either of which may optionally substituted by one or more substituent selected from halo and OH.

In some suitable compounds of general formula (I), R$^1$ is hydrogen, halo, CN, R$^{12}$, OR$^{12}$, SR$^{12}$ or NR$^{12}$R$^{13}$;
wherein R$^{12}$ is C$_{1-6}$ alkyl optionally substituted with one or more substituent R$^a$; or phenyl optionally substituted with one or more substituent R$^b$ and
wherein R$^a$, R$^b$ and R$^{13}$ are as defined above.

More suitably, R$^1$ is hydrogen or R$^{12}$, wherein R$^{12}$ is C$_{1-6}$ alkyl optionally substituted with one or more substituent R$^a$; or phenyl optionally substituted with one or more substituent R$^b$ and
wherein R$^a$ and R$^b$ are as defined above.

In particularly suitable compounds, R$^1$ is hydrogen, C$_{1-4}$ alkyl optionally substituted with one or more halo substituent or phenyl.

In further embodiments, in the compounds of general formula (I), independently or in combination:
R$^1$ is hydrogen; and
R$^{11}$ is hydrogen.

In some suitable compounds of general formula (I), the linker group Y is a single bond, —C$_{1-4}$ alkylene, —C$_{1-4}$ alkylene-O—, —C$_{1-4}$ alkylene-NR$^8$—, —NR$^8$— or —NR$^8$(C$_{1-4}$ alkylene)-; wherein R$^8$ is hydrogen or methyl, but especially hydrogen and wherein alkylene chains are optionally substituted with one or more substituents R$^e$ as defined above.

Suitably, R$^e$ is halo;
More usually, Y is a single bond, C$_{1-4}$ alkylene optionally substituted with one or more halo substituents, —NR$^8$— or —N(R$^8$)C$_{1-4}$ alkylene-, where R$^8$ is H or methyl and alkylene is optionally substituted with one or more halo substituents.

In particularly suitable compounds, Y is a single bond, —CH$_2$—, —(CH$_2$)$_2$—, —(CH$_2$)$_3$—, —CH(CH$_3$)—, —CH(CH$_2$CH$_3$)—, —NH—, —N(CH$_3$)—NHCH$_2$— or —N(CH$_3$)CH$_2$—.

In some suitable compounds of general formula (I) A represents 6- to 10-membered aryl, 3- to 8-membered cycloalkyl, 5- to 10-membered heteroaryl or 3- to 8-membered heterocyclyl, any of which may be substituted as defined above.

More suitably, A represents a phenyl, naphthyl, indanyl, tetrahydronaphthyl, cyclopropyl, cyclobutyl, cyclopentyl, cyclohexyl, thiophenyl, pyrrolyl, pyrazolyl, pyridyl, pyrimidinyl, pyrazinyl, pyridazinyl, benzothiophenyl, benzofuranyl, indolyl, isoindolyl, quinolinyl, isoquinolinyl, benzimidazolyl, tetrahyroquinolinyl, tetrahydroisoquinolinyl, isoindolinyl, benzomorpholinyl, piperidyl, morpholinyl, azetidinyl; any of which may be substituted as defined above.

For example, A may be selected from:
phenyl, pyridyl, pyrazole, thiophenyl, benzothiophenyl, quinolinyl or isoquinolinyl, any of which may be unsubstituted or substituted with one to four R$^2$ groups as defined above; or
a 5- or 6-membered carbocyclic or heterocyclic ring which may be unsubstituted or substituted with one to four R$^2$ groups as defined above, for example by one or two oxo groups; or
a 9- to 10-membered bicyclic aromatic ring which may be unsubstituted or substituted with one to four R$^2$ groups as defined above for example with one to four substitutents selected from halo or, when the ring is partially saturated, with oxo.

In particularly suitable compounds, A represents phenyl, cyclopropyl, cyclobutyl, cyclopentyl, cyclohexyl, thiophen-2-yl, thiophen-3-yl, 3-pyridyl, 4-pyridyl, pyrimidin-4-yl, benzothiophen-2-yl, benzothiophen-3-yl, benzimidazole-6-yl, tetrahydroquinoline-6-yl, tetrahydroisoquinoline-6-yl, pyrazol-3-yl, pyrazol-4-yl, pyrazol-5-yl, benzomorpholin-6-yl, isoindolin-1-yl, piperidine-4-yl, azetidin-3-yl, any of which may be substituted as defined above.

In more still more suitable compounds of general formula (I), A represents phenyl, pyridyl, pyrazolyl, thiophenyl or benzothiophenyl; especially phenyl, 3-pyridyl, 4-pyridyl, thiophen-2-yl, thiophen-3-yl, pyrazol-3-yl, pyrazol-4-yl, pyrazol-5-yl, benzothiophen-2-yl or benzothiophen-3-yl, any of which may be substituted as defined above.

Suitably, n is 0 to 3 and in some cases n is 1 to 3.

In suitable compounds of general formula (I), each R$^2$ is independently selected from: halo, nitro, cyano, OH or when A is saturated or partially saturated, oxo;
C$_{1-4}$ alkyl, C$_{2-4}$ alkenyl, O(C$_{1-4}$ alkyl) any of which may optionally be substituted with one or more substituent R$^3$ as defined above; or
OR$^5$, wherein R$^5$ is as defined above; or
NR$^4$R$^5$, where R$^4$ and R$^5$ are as defined above; or
NR$^4$C(O)R$^6$, where R$^4$ and R$^6$ are as defined above; or
NR$^4$C(O)NR$^5$R$^6$, where R$^4$, R$^5$ and R$^6$ are as defined above; or
C(O)R$^6$ or C(O)OR$^6$, where R$^6$ is as defined above; or
SO$_2$(C$_{1-4}$ alkyl); or
SO$_2$NR$^{21}$R$^{22}$, wherein each of R$^{21}$ and R$^{22}$ is hydrogen or where R$^{21}$ and R$^{22}$ together with the nitrogen atom to which they are attached form a piperidine, pyrrolidine or morpholine ring or a piperazine ring optionally substituted on the other nitrogen atom with methyl or ethyl; or a cyclic group selected from phenyl, naphthyl, 5- to 10-membered heteroaryl or 3- to 8-membered heterocyclyl, any of which is optionally substituted with one or more substituent $R^7$ as defined above.

When $R^2$ is $C_{1-4}$ alkyl, $C_{2-4}$ alkenyl, $O(C_{1-4}$ alkyl), it is suitably unsubstituted or is substituted by an $R^3$ group selected from halo, phenyl, amino, methylamino or dimethylamino.

When $R^2$ is $OR^5$, suitable $R^5$ groups include 5- or membered heterocyclic groups, for example pyrrolidine.

When $R^2$ is $NR^4R^5$, suitable $R^4$ groups include hydrogen, and $C_{1-4}$ alkyl and suitable $R^5$ groups include hydrogen, and 5- or 6-membered heterocyclic groups such as oxazolyl, isoxazolyl and pyrrolyl and piperidinyl.

When $R^2$ is $NR^4C(O)R^6$, $R^4$ is suitably hydrogen or methyl, especially hydrogen, and $R^6$ is $C_{1-4}$ alkyl optionally substituted with one or more $R^h$, where each $R^h$ is independently, OH, $NH_2$, phenyl, or $OC_{1-4}$ alkyl; or $R^6$ is phenyl.

When $R^2$ is $NR^4C(O)NR^5R^6$, $R^4$ is suitably hydrogen or methyl, especially hydrogen, $R^5$ is suitably hydrogen and $R^6$ is suitably $C_{1-4}$ alkyl, for example methyl.

When $R^2$ is $C(O)R^6$ or $C(O)OR^6$, $R^6$ may be $C_{1-4}$ alkyl substituted with phenyl and/or $NH_2$.

When $R^2$ is a cyclic group, it may be, for example phenyl, pyridyl, pyrazolyl, oxazolyl, isoxazolyl, pyrrolidinyl, piperidinyl, piperazinyl, morpholinyl, diazepanyl or azetidinyl, any of which may be substituted by one or more substituents $R^7$, where $R^7$ is as defined above but is especially halo, $C_{1-4}$ haloalkyl or $NH_2$; and wherein pyrazolyl, oxazolyl, isoxazolyl, pyrrolidinyl, piperidinyl, piperazinyl, morpholinyl, diazepanyl or azetidinyl may be substituted by one or more oxo groups in addition to or instead of an $R^7$ group.

In some suitable compounds of general formula (I):
A is phenyl or pyridyl;
n is 0 to 3; and
$R^2$ is halo, $CF_3$; nitro, methoxy, phenyl, $SO_2$—$C_{1-4}$ alkyl; or $C_{1-2}$ alkyl or ethenyl optionally substituted with phenyl or —$C(O)NR^{14}R^{15}$, where $R^{14}$ and $R^{15}$ are each independently H or methyl; or
a 4- to 7-membered carbocyclic or heterocyclic ring optionally substituted with one or more $R^7$ groups, where $R^7$ is as defined above; $NHR^4$, $NHR^5$, $NHC(O)R^6$ or $NR^4C(O)NR^5R^6$ where $R^4$, $R^5$ and $R^6$ are defined above.

In these compounds, more suitably, $R^2$ is halo, trifluoromethyl, nitro, methoxy, phenyl; or
oxazoline, morpholine, pyrrolidine, piperidine, tetrahydropyridine, piperazine diazepan or aziridine any of which may optionally be substituted with an oxo group or with $NH_2$ or $C_{1-2}$ alkyl or haloalkyl; or
oxazole, pyrazole, either of which may optionally be substituted with methyl; or $NHC(O)C_{1-2}$ alkyl, either of which may optionally be substituted by OH or methoxy; or NHC(O)NHCH$_3$, $NH_2$, $NH(CH_3)$, $CH_2N(CH_3)_2$, $SO_2CH_3$; or Ethenyl substituted with phenyl or $C(O)N(CH_3)_2$.

In a particularly suitable group of compounds where A is phenyl or pyridyl, n is 1 to 3 and each $R^2$ is independently selected from halo, trifluoromethyl, nitro and methoxy.

Compounds in which A is phenyl are often more suitable than compounds in which A is pyridyl.

In some compounds of general formula (I), the cyclic group A is phenyl.

In such compounds, in one embodiment, the phenyl group is substituted with one to three halo substituents $R^2$. Suitably, one of the halo substituents is at the 2-position.

In one embodiment, the phenyl group has a halo substituent at the 2-position.

In an alternative embodiment, the phenyl group has a halo substituent at the 3-position.

In an alternative embodiment the phenyl group has a halo substituent at the 4-position.

Optionally in these embodiments the phenyl group may also have one or two other substituents $R^2$.

In yet another embodiment, the phenyl group has two halo substituents at the 2- and 5-positions.

In yet another embodiment, the phenyl group has two halo substituents at the 2- and 3-positions.

In yet another embodiment, the phenyl group has two halo substituents at the 3- and 5-positions.

In yet another embodiment, the phenyl group has two halo substituents at the 3- and 4-positions.

In yet another embodiment, the phenyl group has one or two halo substituents and an additional substituent selected form trifluoromethyl and nitro. Suitably, a halo substituent is at the 2-position.

In an alternative embodiment, the cyclic group is phenyl and is substituted with at least one trifluoromethyl group.

In one embodiment, the trifluoromethyl group is at the 2-position.

In an alternative embodiment, the trifluoromethyl group is at the 3-position.

In a further alternative embodiment, the trifluoromethyl group is at the 4-position.

Optionally in these embodiments the phenyl group may also have one or two other substituents $R^2$.

In yet another embodiment, the cyclic group is phenyl and has an amino substituent.

In one embodiment, the amino group is at the 2-position.

In an alternative embodiment, the amino group is at the 3-position.

In a further alternative embodiment, the amino group is at the 4-position.

In other compounds of general formula (I), the cyclic group A is a 3- to 6-membered carbocyclic or heterocyclic ring optionally fused to a phenyl group.

Typically, in such compounds, independently or in any combination:
n is 0-2;
at least one $R^2$ is oxo, or when attached to a ring nitrogen atom is $C(O)OR^6$, wherein $R^6$ is benzyl.

Alternatively, A may be pyrazolyl or thiophenyl, especially pyrazol-4-yl, pyrazol-5-yl, thiophen-2-yl or thiophen-3-yl.

Typically in such compounds, independently or in any combination:
n is 1 to 3;
$R^2$ is halo, methyl, trifluoromethyl or phenyl or pyridyl, either of which may optionally be substituted with halo or trifluoromethyl, especially trifluoromethyl.

Alternatively, A may be quinolinyl, isoquinolinyl or benzothiophenyl especially quinolin-6-yl or benzothiophen-2-yl. Typically in such compounds n is 0.

Particularly suitable compounds of the present invention are as follows (where the numbers refer to the compound numbers in Tables 1 and 2 below):
1. 5-benzenesulfonamido-1,3-thiazole-4-carboxylic acid;
2. 5-{[(3,5-dichlorophenyl)methyl]sulfonamido}-1,3-thiazole-4-carboxylic acid;
3. 5-(2,4,6-trimethylphenylsulfonamido)thiazole-4-carboxylic acid;
4. 5-{[3-(trifluoromethyl)phenyl]sulfonamido}-1,3-thiazole-4-carboxylic acid;
5. 5-(phenylmethylsulfonamido)thiazole-4-carboxylic acid;
6. 5-(3-methoxyphenylsulfonamido)thiazole-4-carboxylic acid;
7. 5-(2-phenylethylsulfonamido)thiazole-4-carboxylic acid;

8. 5-(thiophene-2-sulfonamido)thiazole-4-carboxylic acid;
9. 5-(4,5-dichlorothiophene-2-sulfonamido)thiazole-4-carboxylic acid;
10. 5-(2,5-dichlorothiophene-3-sulfonamido)thiazole-4-carboxylic acid;
11. 5-(2-(trifluoromethyl)phenylsulfonamido)thiazole-4-carboxylic acid;
12. 5-(4-(trifluoromethyl)phenylsulfonamido)thiazole-4-carboxylic acid;
13. 5-(2-chloro-5-(trifluoromethyl)phenylsulfonamido)thiazole-4-carboxylic acid;
14. 5-(3,5-bis(trifluoromethyl)phenylsulfonamido)thiazole-4-carboxylic acid;
15. 5-({[2-(trifluoromethyl)phenyl]methyl}sulfonamido)-1,3-thiazole-4-carboxylic acid;
16. 5-{[(2-methylphenyl)methyl]sulfonamido}-1,3-thiazole-4-carboxylic acid;
17. 5-((2-nitrophenyl)methylsulfonamido)thiazole-4-carboxylic acid;
18. 5-{[(2-bromophenyl)methyl]sulfonamido}-1,3-thiazole-4-carboxylic acid;
19. 5-(5-chlorothiophene-2-sulfonamido)thiazole-4-carboxylic acid;
20. 5-(5-phenylthiophene-2-sulfonamido)thiazole-4-carboxylic acid;
21. 5-(thiophene-3-sulfonamido)thiazole-4-carboxylic acid;
22. 5-(2,5-dimethylthiophene-3-sulfonamido)thiazole-4-carboxylic acid;
23. 5-([1,1'-biphenyl]-2-ylsulfonamido)thiazole-4-carboxylic acid;
24. 5-((2-aminophenyl)methylsulfonamido)thiazole-4-carboxylic acid;
25. 5-((2-acetamidophenyl)methylsulfonamido)thiazole-4-carboxylic acid;
26. 5-((2-benzamidophenyl)methylsulfonamido)thiazole-4-carboxylic acid;
27. (E)-5-((2-styrylphenyl)methylsulfonamido)thiazole-4-carboxylic acid;
28. (E)-5-((2-(3-(dimethylamino)-3-oxoprop-1-en-1-yl)phenyl)methylsulfonamido)thiazole-4-carboxylic acid;
29. 5-([1,1'-biphenyl]-2-ylmethylsulfonamido)thiazole-4-carboxylic acid;
30. 5-((2-(trifluoromethoxy)phenyl)methylsulfonamido)thiazole-4-carboxylic acid;
31. 5-((3-(trifluoromethyl)phenyl)methylsulfonamido)thiazole-4-carboxylic acid;
32. 5-((3-bromophenyl)methylsulfonamido)thiazole-4-carboxylic acid;
33. 5-((3-cyanophenyl)methylsulfonamido)thiazole-4-carboxylic acid;
34. 5-((2-chlorophenyl)methylsulfonamido)thiazole-4-carboxylic acid;
35. 5-(4-nitrophenylsulfonamido)thiazole-4-carboxylic acid;
37. 5-({5-[5-(trifluoromethyl)-1,2-oxazol-3-yl]thiophen-2-yl}sulfonamido)-1,3-thiazole-4-carboxylic acid;
38. 5-(1-benzothiophene-2-sulfonamido)-1,3-thiazole-4-carboxylic acid;
39. 5-[(5-methylthiophen-2-yl)sulfonamido]-1,3-thiazole-4-carboxylic acid;
40. 5-[(5-bromothiophen-2-yl)sulfonamido]-1,3-thiazole-4-carboxylic acid;
41. 5-(1-benzothiophene-3-sulfonamido)-1,3-thiazole-4-carboxylic acid;
42. 5-[(4-bromo-2,5-dichlorothiophen-3-yl)sulfonamido]-1,3-thiazole-4-carboxylic acid;
43. 5-({[(2-chlorophenyl)methyl]sulfamoyl}amino)-1,3-thiazole-4-carboxylic acid;
44. 5-[({[3-(trifluoromethyl)phenyl]methyl}sulfamoyl)amino]-1,3-thiazole-4-carboxylic acid;
45. 5-[(3-bromothiophen-2-yl)sulfonamido]-1,3-thiazole-4-carboxylic acid;
46. 5-{[(2-iodophenyl)methyl]sulfonamido}-1,3-thiazole-4-carboxylic acid;
47. 5-{[4-phenyl-5-(trifluoromethyl)thiophen-3-yl]sulfonamido}-1,3-thiazole-4-carboxylic acid;
48. 5-{[(2,3-dichlorophenyl)methyl]sulfonamido}-1,3-thiazole-4-carboxylic acid;
49. 5-{[(3,4-dichlorophenyl)methyl]sulfonamido}-1,3-thiazole-4-carboxylic acid;
50. 5-benzylsulfonamido-2-methyl-1,3-thiazole-4-carboxylic acid;
51. 2-methyl-5-(quinoline-8-sulfonamido)-1,3-thiazole-4-carboxylic acid;
52. 5-benzenesulfonamido-2-methyl-1,3-thiazole-4-carboxylic acid;
53. 5-{[(3,5-dichlorophenyl)methyl]sulfonamido}-2-methyl-1,3-thiazole-4-carboxylic acid;
54. 5-[(2-chlorophenyl)sulfonamido]-2-methyl-1,3-thiazole-4-carboxylic acid;
55. 2-methyl-5-[(2,4,6-trimethylphenyl)sulfonamido]-1,3-thiazole-4-carboxylic acid;
56. 5-[(2,5-dichlorothiophen-3-yl)sulfonamido]-2-methyl-1,3-thiazole-4-carboxylic acid;
57. 5-{[(2-bromophenyl)methyl]sulfonamido}-2-methyl-1,3-thiazole-4-carboxylic acid;
58. 5-benzenesulfonamido-2-phenyl-1,3-thiazole-4-carboxylic acid;
59. 5-benzenesulfonamido-2-ethyl-1,3-thiazole-4-carboxylic acid;
60. 5-[(1-phenylethyl)sulfonamido]-1,3-thiazole-4-carboxylic acid;
61. 5-{[6-(trifluoromethyl)pyridin-3-yl]sulfonamido}-1,3-thiazole-4-carboxylic acid;
62. 5-[(2-phenoxyethyl)sulfonamido]-1,3-thiazole-4-carboxylic acid;
63. 5-{[2-(1,3-dioxo-2,3-dihydro-1H-isoindol-2-yl)ethyl]sulfonamido}-1,3-thiazole-4-carboxylic acid;
64. 5-{[2-(2-chlorophenyl)ethyl]sulfonamido}-1,3-thiazole-4-carboxylic acid;
65. 5-({1-[5-(trifluoromethyl)pyridin-2-yl]-1H-pyrazol-4-yl}sulfonamido)-1,3-thiazole-4-carboxylic acid;
66. 5-[(2-chlorophenyl)sulfonamido]-1,3-thiazole-4-carboxylic acid;
67. 5-(pyridine-3-sulfonamido)-1,3-thiazole-4-carboxylic acid;
68. 5-[(2,6-dichlorophenyl)sulfonamido]-1,3-thiazole-4-carboxylic acid;
69. 5-(cyclohexylmethyl)sulfonamido-1,3-thiazole-4-carboxylic acid;
70. 5-[(4-methyl-3,4-dihydro-2H-1,4-benzoxazin-7-yl)sulfonamido]-1,3-thiazole-4-carboxylic acid;
71. 5-[(1-phenylpropyl)sulfonamido]-1,3-thiazole-4-carboxylic acid;
72. 5-{[2-(4-methoxyphenyl)ethyl]sulfonamido}-1,3-thiazole-4-carboxylic acid;
73. 5-({2-[3-(trifluoromethyl)phenyl]ethyl}sulfonamido)-1,3-thiazole-4-carboxylic acid;
74. 5-{[2-(4-chlorophenyl)ethyl]sulfonamido}-1,3-thiazole-4-carboxylic acid;
75. 5-[(piperidine-1-sulfonyl)amino]-1,3-thiazole-4-carboxylic acid;

76. 5-[(phenylsulfamoyl)amino]-1,3-thiazole-4-carboxylic acid;
77. 5-{[benzyl(methyl)sulfamoyl]amino}-1,3-thiazole-4-carboxylic acid;
78. 5-[(4-acetamidophenyl)sulfonamido]-1,3-thiazole-4-carboxylic acid;
79. 5-[(2-methoxyphenyl)sulfonamido]-1,3-thiazole-4-carboxylic acid;
80. 5-(1,2,3,4-tetrahydronaphthalene-1-sulfonamido)-1,3-thiazole-4-carboxylic acid;
81. 5-[(5-methyl-1-phenyl-1H-pyrazol-4-yl)sulfonamido]-1,3-thiazole-4-carboxylic acid;
82. 5-(cyclopropylmethyl)sulfonamido-1,3-thiazole-4-carboxylic acid;
83. 5-{[(2-methoxyphenyl)methyl]sulfonamido}-1,3-thiazole-4-carboxylic acid;
84. 5-{[2-(2-methoxyphenyl)ethyl]sulfonamido}-1,3-thiazole-4-carboxylic acid;
85. 5-{[2-(3-methoxyphenyl)ethyl]sulfonamido}-1,3-thiazole-4-carboxylic acid;
86. 5-{[2-(3-chlorophenyl)ethyl]sulfonamido}-1,3-thiazole-4-carboxylic acid;
87. 5-[(2-methanesulfonylphenyl)sulfonamido]-1,3-thiazole-4-carboxylic acid;
88. 5-{[methyl(phenyl) sulfamoyl]amino}-1,3-thiazole-4-carboxylic acid;
89. 5-{[4-(morpholin-4-yl)phenyl]sulfonamido}-1,3-thiazole-4-carboxylic acid;
90. 5-[(4-cyanophenyl)sulfonamido]-1,3-thiazole-4-carboxylic acid;
91. 5-(pyridine-2-sulfonamido)-1,3-thiazole-4-carboxylic acid;
92. 5-[(1-methyl-1H-imidazol-2-yl)sulfonamido]-1,3-thiazole-4-carboxylic acid;
93. 5-[(6-methoxypyridin-3-yl)sulfonamido]-1,3-thiazole-4-carboxylic acid;
94. 5-{[4-(1H-pyrazol-1-yl)phenyl]sulfonamido}-1,3-thiazole-4-carboxylic acid;
95. 5-[(1-ethyl-5-methyl-1H-pyrazol-4-yl)sulfonamido]-1,3-thiazole-4-carboxylic acid;
96. 5-{[(2-chlorophenyl)methyl]sulfonamido}-2-(trifluoromethyl)-1,3-thiazole-4-carboxylic acid;
97. 5-{[(2-cyanophenyl)methyl]sulfonamido}-1,3-thiazole-4-carboxylic acid;
98. 5-[(1-methyl-H-pyrazol-3-yl)sulfonamido]-1,3-thiazole-4-carboxylic acid;
99. 5-[(1-methyl-H-pyrazol-5-yl)sulfonamido]-1,3-thiazole-4-carboxylic acid;
100. 5-({1-[(benzyloxy)carbonyl]piperidin-4-yl}sulfonamido)-1,3-thiazole-4-carboxylic acid;
101. 5-[(3-phenylpropyl)sulfonamido]-1,3-thiazole-4-carboxylic acid;
102. 5-{[(2-chlorophenyl)methyl]sulfonamido}-2-methyl-1,3-thiazole-4-carboxylic acid;
104. 5-(2,3-dihydro-1H-indene-1-sulfonamido)-1,3-thiazole-4-carboxylic acid;
105. 5-{[4-(1-methyl-1H-pyrazol-5-yl)phenyl]sulfonamido}-1,3-thiazole-4-carboxylic acid;
106. 5-{[2-(1,2,3,4-tetrahydroquinolin-1-yl)ethyl]sulfonamido}-1,3-thiazole-4-carboxylic acid;
107. 5-{[2-(N-phenylacetamido)ethyl]sulfonamido}-1,3-thiazole-4-carboxylic acid;
108. 5-{[4-(3-oxomorpholin-4-yl)phenyl]sulfonamido}-1,3-thiazole-4-carboxylic acid;
109. 5-{[4-(2-oxo-1,3-oxazolidin-3-yl)phenyl]sulfonamido}-1,3-thiazole-4-carboxylic acid;
110. 5-[(1,2-dimethyl-1H-imidazol-4-yl)sulfonamido]-1,3-thiazole-4-carboxylic acid;
111. 5-[(oxan-4-ylmethyl)sulfonamido]-1,3-thiazole-4-carboxylic acid;
112. 5-[({1-[(benzyloxy)carbonyl]piperidin-4-yl}methyl)sulfonamido]-1,3-thiazole-4-carboxylic acid;
113. 5-{[4-(2-oxopyrrolidin-1-yl)phenyl]sulfonamido}-1,3-thiazole-4-carboxylic acid;
114. 5-({1-[6-(trifluoromethyl)pyridin-3-yl]-1H-pyrazol-4-yl}sulfonamido)-1,3-thiazole-4-carboxylic acid;
115. 5-{[4-(1,3-oxazol-5-yl)phenyl]sulfonamido}-1,3-thiazole-4-carboxylic acid;
116. 5-{[4-(1H-pyrazol-4-yl)phenyl]sulfonamido}-1,3-thiazole-4-carboxylic acid;
117. 5-[(1-phenyl-1H-pyrazol-4-yl)sulfonamido]-1,3-thiazole-4-carboxylic acid;
118. 5-{[4-(piperidin-4-yl)phenyl]sulfonamido}-1,3-thiazole-4-carboxylic acid;
119. 5-[(4-propanamidophenyl)sulfonamido]-1,3-thiazole-4-carboxylic acid;
120. 5-{[4-(2-hydroxyacetamido)phenyl]sulfonamido}-1,3-thiazole-4-carboxylic acid;
121. 5-({4-[(methylcarbamoyl)amino]phenyl}sulfonamido)-1,3-thiazole-4-carboxylic acid;
122. 5-{[(2,4-dichlorophenyl)methyl]sulfonamido}-1,3-thiazole-4-carboxylic acid;
123. 5-{[(2-fluorophenyl)methyl]sulfonamido}-1,3-thiazole-4-carboxylic acid;
124. 5-{[(2,3-difluorophenyl)methyl]sulfonamido}-1,3-thiazole-4-carboxylic acid;
125. 5-{[4-(2-methoxyacetamido)phenyl]sulfonamido}-1,3-thiazole-4-carboxylic acid;
126. 5-{[(2,5-dichlorophenyl)methyl]sulfonamido}-1,3-thiazole-4-carboxylic acid;
127. 5-{[(2,6-dichlorophenyl)methyl]sulfonamido}-1,3-thiazole-4-carboxylic acid;
128. 5-{[(2-chloro-6-fluorophenyl)methyl]sulfonamido}-1,3-thiazole-4-carboxylic acid;
129. 5-{[(2-chloro-4-fluorophenyl)methyl]sulfonamido}-1,3-thiazole-4-carboxylic acid;
130. 5-({[2-chloro-5-(trifluoromethyl)phenyl]methyl}sulfonamido)-1,3-thiazole-4-carboxylic acid;
131. 5-({4-[(dimethylamino)methyl]phenyl}sulfonamido)-1,3-thiazole-4-carboxylic acid;
132. 5-{[(2,3,5-trichlorophenyl)methyl]sulfonamido}-1,3-thiazole-4-carboxylic acid;
133. 5-{[(2,3-dichloro-6-fluorophenyl)methyl]sulfonamido}-1,3-thiazole-4-carboxylic acid;
134. 5-({[2,3-dichloro-6-(trifluoromethyl)phenyl]methyl}sulfonamido)-1,3-thiazole-4-carboxylic acid;
135. 5-{[(4-bromo-2-chlorophenyl)methyl]sulfonamido}-1,3-thiazole-4-carboxylic acid;
136. 5-({2-[methyl(phenyl)amino]ethyl}sulfonamido)-1,3-thiazole-4-carboxylic acid;
137. 5-{[(4-nitrophenyl)methyl]sulfonamido}-1,3-thiazole-4-carboxylic acid;
138. 5-[6-(piperidin-1-yl)pyridin-3-ylsulfonamido]-1,3-thiazole-4-carboxylic acid;
139. 5-[6-(methylamino)pyridin-3-ylsulfonamido]-1,3-thiazole-4-carboxylic acid;
140. 5-[6-(4-methylpiperazin-1-yl)pyridin-3-ylsulfonamido]-1,3-thiazole-4-carboxylic acid;
141. 5-(6-acetamidopyridin-3-ylsulfonamido)-1,3-thiazole-4-carboxylic acid;
142. 5-{4-[(5-methyl-1,2-oxazol-3-yl)amino]phenylsulfonamido}-1,3-thiazole-4-carboxylic acid;

143. 5-(6-aminopyridin-3-ylsulfonamido)-1,3-thiazole-4-carboxylic acid;
144. 5-[(6-chloro-2H-1,3-benzodioxol-5-yl)methylsulfonamido]-1,3-thiazole-4-carboxylic acid;
145. 5-{[(2-chloro-6-nitrophenyl)methyl]sulfonamido}-1,3-thiazole-4-carboxylic acid;
146. 5-(quinoline-6-sulfonamido)-1,3-thiazole-4-carboxylic acid;
147. 5-[(2,3-dihydroindole-1-sulfonyl)amino]-1,3-thiazole-4-carboxylic acid;
148. 5-(4-methanesulfonylphenylsulfonamido)-1,3-thiazole-4-carboxylic acid;
149. 5-[3-(2-oxo-1,3-oxazolidin-3-yl)phenylsulfonamido]-1,3-thiazole-4-carboxylic acid;
150. 5-[3-(2H-pyrazol-3-yl)phenylsulfonamido]-1,3-thiazole-4-carboxylic acid;
151. 5-[2-(pyridin-3-yl)ethylsulfonamido]-1,3-thiazole-4-carboxylic acid;
152. 5-[3-(3-oxomorpholin-4-yl)phenylsulfonamido]-1,3-thiazole-4-carboxylic acid;
153. 5-[3-(2-oxopyrrolidin-1-yl)phenylsulfonamido]-1,3-thiazole-4-carboxylic acid;
154. 5-[6-(piperidin-4-ylamino)pyridin-3-ylsulfonamido]-1,3-thiazole-4-carboxylic acid;
155. 5-(6-{[2-(dimethylamino)ethyl]amino}pyridin-3-ylsulfonamido)-1,3-thiazole-4-carboxylic acid;
156. 5-[(4-acetamidophenyl)methylsulfonamido]-1,3-thiazole-4-carboxylic acid;
157. 5-[6-(piperazin-1-yl)pyridin-3-ylsulfonamido]-1,3-thiazole-4-carboxylic acid;
158. 5-[6-(4-aminopiperidin-1-yl)pyridin-3-ylsulfonamido]-1,3-thiazole-4-carboxylic acid;
159. 5-[6-(3-aminopyrrolidin-1-yl)pyridin-3-ylsulfonamido]-1,3-thiazole-4-carboxylic acid;
160. 5-[6-(pyrrolidin-1-yl)pyridin-3-ylsulfonamido]-1,3-thiazole-4-carboxylic acid;
161. 5-[6-(3-aminopiperidin-1-yl)pyridin-3-ylsulfonamido]-1,3-thiazole-4-carboxylic acid;
162. 5-[6-(1,4-diazepan-1-yl)pyridin-3-ylsulfonamido]-1,3-thiazole-4-carboxylic acid;
163. 5-[4-(pyrrolidin-3-yloxy)phenylsulfonamido]-1,3-thiazole-4-carboxylic acid;
164. 5-[6-(3-aminoazetidin-1-yl)pyridin-3-ylsulfonamido]-1,3-thiazole-4-carboxylic acid;
165. 5-[6-(piperidin-4-yl)pyridin-3-ylsulfonamido]-1,3-thiazole-4-carboxylic acid;
166. 5-[6-(1,2,3,6-tetrahydropyridin-4-yl)pyridin-3-ylsulfonamido]-1,3-thiazole-4-carboxylic acid;
167. 5-{6-[4-(2,2,2-trifluoroethyl)piperazin-1-yl]pyridin-3-ylsulfonamido}-1,3-thiazole-4-carboxylic acid;
168. 5-[1-(2-chlorophenyl)ethylsulfonylamino]thiazole-4-carboxylic acid (entantiomer 1);
169. 5-[1-(2-chlorophenyl)ethylsulfonylamino]thiazole-4-carboxylic acid (enantiomer 2);
170. 5-(3-pyridylmethylsulfonylamino)thiazole-4-carboxylic acid;
171. 5-(isoindolin-5-ylmethylsulfonylamino)thiazole-4-carboxylic acid;
172. S-5-[[4-[1-(2-amino-2-phenyl-acetyl)-4-piperidyl]phenyl]sulfonylamino]thiazole-4-carboxylic acid;
173. R-5-[[4-[1-(2-amino-2-phenyl-acetyl)-4-piperidyl]phenyl]sulfonylamino]thiazole-4-carboxylic acid;
174. 5-[[4-[(2-aminoacetyl)amino]phenyl]sulfonylamino]thiazole-4-carboxylic acid;
175. 5-[(4-acetamido-3-fluoro-phenyl)sulfonylamino]thiazole-4-carboxylic acid;
176. 5-[[4-[(2-hydroxy-2-methyl-propanoyl)amino]phenyl]sulfonylamino]thiazole-4-carboxylic acid;
177. 5-[[4-[(2-hydroxy-2-phenyl-acetyl)amino]phenyl]sulfonylamino]thiazole-4-carboxylic acid;
178. 5-[[4-[(2-hydroxy-3-phenyl-propanoyl)amino]phenyl]sulfonylamino]thiazole-4-carboxylic acid;
179. 5-[[2-(2-hydroxyethylamino)pyrimidin-5-yl]sulfonylamino]thiazole-4-carboxylic acid (X12);
180. 5-[(2-methylpyrimidin-5-yl)sulfonylamino]thiazole-4-carboxylic acid;
181. 5-[[2-(4-pyridyl)pyrimidin-5-yl]sulfonylamino]thiazole-4-carboxylic acid;
182. 5-[(6-methyl-3-pyridyl)sulfonylamino]thiazole-4-carboxylic acid;
183. 5-[(2-chloro-3-nitro-phenyl)methylsulfonylamino]thiazole-4-carboxylic acid;

or a salt thereof.

In the compounds above, where separate enantiomers are mentioned, the invention also encompasses racemic mixtures thereof. This applies in particular to Compounds 168 and 169 and to Compounds 172 and 173 above.

Suitably, the salt is a pharmaceutically or veterinarily acceptable salt.

Compounds of general formula (I) may be prepared according to the routes set out in Scheme 1.

Scheme 1

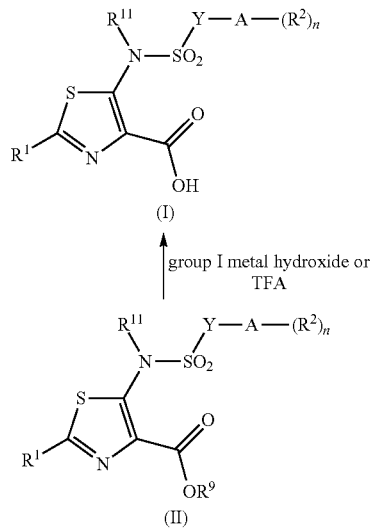

-continued

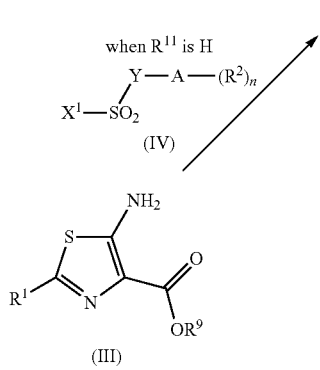
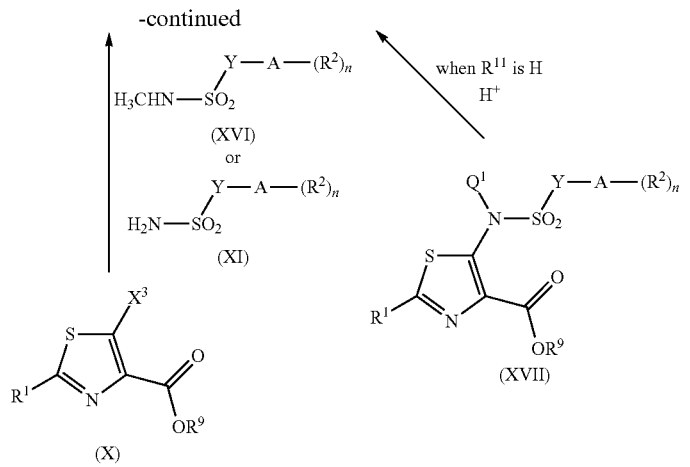
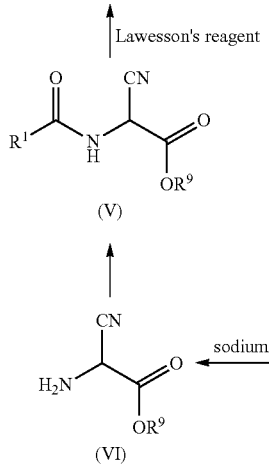
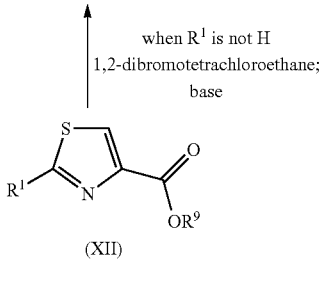
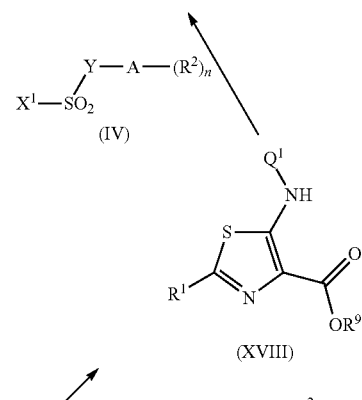
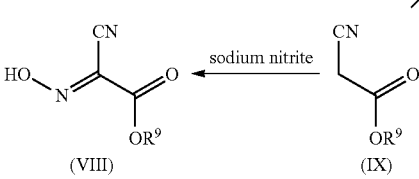
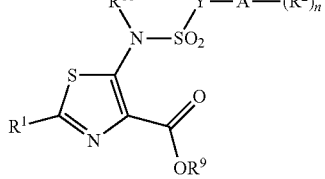

Thus, compounds of general formula (I) may be prepared from esters of general formula (II):

(II)

wherein $R^1$, $R^{11}$, Y, A, n, and $R^2$ are as defined for general formula (I); and
$R^9$ is $C_{1-6}$ alkyl or benzyl optionally substituted with methyl, methoxy, fluoro or trifluoromethyl, and especially benzyl substituted by one or two methoxy groups;
either by hydrolysis with a suitable base, for example a group (I) metal hydroxide such as potassium hydroxide, sodium hydroxide or lithium hydroxide, with lithium hydroxide being particularly suitable; or
by hydrolysis with a strong acid such as trifluoroacetic acid (TFA); or.
by hydrogenation if $R^9$ is benzyl or substituted benzyl.

Therefore a further aspect of the invention provides compounds of general formula (II) as defined above. In addition to their use as precursors of the compounds of general formula (I), the compounds of general formula (II) may also be of use as prodrugs since they are metabolised in vivo to compounds of general formula (I).

Base hydrolysis may be conducted in a suitable solvent, for example a polar solvent such a mixture of tetrahydrofuran and water at a temperature of 10-50° C., especially 15-25° C., for example room temperature.

Acid hydrolysis is typically carried out using aqueous TFA, for example 95% TFA. The reaction may be conducted at a temperature of 10-50° C., especially 15-25° C., for example room temperature.

Thus, in a further aspect of the invention there is provided a process for the preparation of a compound of general formula (I), the process comprising reacting a compound of general formula (II) with a base or an acid.

Compounds of general formula (II) in which $R^{11}$ is hydrogen may be synthesised by reacting a compound of general formula (III):

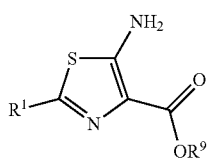 (III)

wherein $R^1$ is as defined for general formula (I) and $R^9$ is as defined for general formula (II); with a compound of general formula (IV):

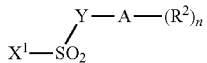 (IV)

wherein Y, n, $R^2$ and A are as defined for general formula (I); and $X^1$ is a leaving group, for example a halide, especially chloride.

The reaction may be conducted in a polar organic solvent, typically a chlorinated solvent such as dichloromethane, and in the presence of a mild base, for example pyridine. Typically the reaction is conducted at a temperature of about 15 to 30° C., usually at room temperature.

Alternatively, in cases where it is necessary to use less mild conditions, a stronger base, for example sodium hydride may be used. Tetrahydrofuran is a suitable solvent in such cases.

In some cases, preparation of a compound of general formula (II) from compounds of general formulae (III) and (IV) followed by hydrolysis to give a compound of general formula (I) may be carried out in one pot without purification of the ester of general formula (II).

Compounds of general formula (II) in which $R^{11}$ is other than hydrogen may be prepared by reductive amination of the compound of general formula (III) prior to reaction with the compound of general formula (IV). For example, the primary amine of general formula (III) can be alkylated using a reductive alkylation process. For example, the amine can be treated with an aldehyde (such as formaldehyde or p-methoxy-benzaldehyde) and a borohydride (such as sodium triacetoxyborohydride, or sodium cyanoborohydride in a solvent (such as a halogenated hydrocarbon, for example dichloromethane, or an alcohol, for example ethanol) and, where necessary, in the presence of an acid (such as acetic acid). The products of such a reaction could be sulfonylated using a moiety of the general formula (IV) to give compounds of general formula (II).

Alternatively, compounds of general formula (II) in which $R^{11}$ is H may be treated with a base (such as sodium hydride or potassium t-butoxide) in an appropriate solvent (such as THF) in the presence of an alkylating agent of the general formula $R^{11}$—X, where X is a suitable leaving group (such as methyl iodide or benzyl bromide) to give compounds of the general formula (II) in which $R^{11}$ is $C_{1-4}$ alkyl optionally substituted by halo or benzyl optionally substituted by halo. (see Smith, March, *March's Advanced Organic Chemistry*, 5th Edition, Wiley: New York, 2001).

Many compounds of general formula (IV) are readily available or may be synthesised by known methods. Other compounds of general formula (IV) may be synthesised by the reaction of a compound of general formula (XXI):

 (XXI)

wherein Y, n, $R^2$ and A are as defined for general formula (I); and

Y is a bond or $NH_2$;

by reaction with chlorosulfonic acid.

A mixture of the compound of formula (XXI) and chlorosulfonic acid may be heated to a temperature of 70-110° C., suitably 85-95° C. for a prolonged period, suitably 12-24 hours.

Compounds of general formula (XXI) are well known and are readily available or may be synthesised by known methods.

The synthesis of compounds of general formula (III) is based on well-known literature procedures and is illustrated in Scheme I, where $R^9$ is shown as ethyl.

Thus, compounds of general formula (III) may be prepared from compounds of general formula (V):

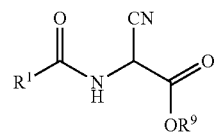 (V)

wherein $R^1$ is as defined for general formula (I) and $R^9$ is as defined for general formula (II); by reaction with Lawesson's reagent (2,4-bis(4-methoxyphenyl)-1,3,2,4-dithiadiphosphetane-2,4-disulfide). The reaction may be carried out in a non-polar organic solvent, for example toluene, under an inert atmosphere such as nitrogen and at elevated temperature, for example 50 to 90° C., usually about 60-80° C.

Compounds of general formula (V) in which $R^1$ is other than hydrogen may be prepared by reaction of a compound of general formula (VI):

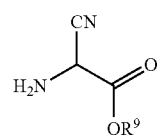 (VI)

wherein $R^9$ is as defined for general formula (II);
with a compound of general formula (VIIa): or (VIIb)

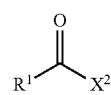 (VIIa)

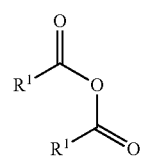 (VIIb)

wherein $R^1$ is as defined for general formula (I) and $X^2$ is a leaving group, for example a halide, particularly a chloride.

The reaction may be carried out in the presence of an organic base such as pyridine or triethylamine and at a temperature of about 15 to 30° C., typically at room temperature.

When $R^1$ is H, it is not possible to use this method because the compounds of formula (VIIa)—formyl chloride, and (VIIb)—formyl anhydride, are insufficiently stable. Therefore, when $R^1$ is H, the compounds of formula (V) may be prepared by reaction of a compound of general formula (VI) with a mixture of formic acid and a carboxlic acid halide or anhydride, for example acetyl chloride or acetic anhydride.

Compounds of general formula (VIIa) and (VIIb) are well known and are readily available or may be prepared by methods familiar to those of skill in the art.

Compounds of general formula (VI) may be prepared from compounds of general formula (VIII):

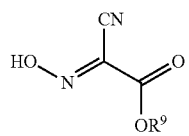
(VIII)

wherein $R^9$ is as defined for general formula (II);

by reaction with a base followed by sodium dithionate in aqueous solution. Suitable bases include alkali metal bases, for example sodium, potassium or lithium hydroxide, with sodium hydroxide being particularly suitable. The reaction may be carried out at a temperature of about 15 to 30° C., typically at room temperature.

Compounds of general formula (VIII) may be prepared from compounds of general formula (IX):

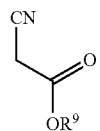
(IX)

wherein $R^9$ is as defined for general formula (II);

by reaction with sodium nitrite. Typically the reaction is conducted in acidic solution and at reduced temperature, for example −5 to 5° C.

An alternative method for the synthesis of compounds of general formula (II) in which $R^{11}$ is hydrogen is by the reaction of a compound of general formula (X):

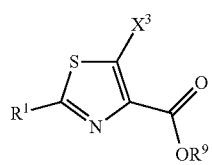
(X)

wherein $R^1$ is as defined for general formula (I), $R^9$ is as defined for general formula (II) and $X^3$ is a leaving group, typically a halide such as bromide;

with a compound of general formula (XI):

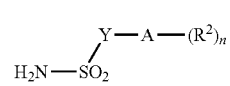
(XI)

wherein Y, n, $R^2$ and A are as defined for general formula (I).

Typically the reaction may be carried out in the presence of a palladium or copper catalyst, for example Tris(dibenzylideneacetone)dipalladium(0) ($Pd_2dba_3$) or cuprous iodide (CuI) at elevated temperature, typically 70 to 110° C., more usually 75 to 95° C., under an inert atmosphere, for example nitrogen or argon.

When $Pd_2dba_3$ is used as the catalyst, the reaction is suitably carried out in the presence of a ligand for palladium, for example 4,5-bis(diphenylphosphino)-9,9-dimethylxanthene (xantphos) and a base, for example caesium carbonate.

Instead of the compound (XI) as shown above, the compound of general formula (X) may be reacted with a compound of general formula (XVI):

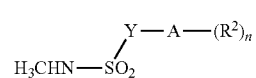
(XVI)

wherein Y, n, $R^2$ and A are as defined for general formula (I).

The reaction conditions used are similar to those described above for the reaction with the compound of general formula (XI).

Many compounds of general formula (X) are readily available. However, compounds of general formula (X) may also be synthesised from compounds of general formula (XII):

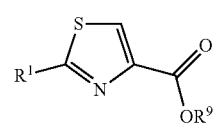
(XII)

wherein $R^1$ is as defined in general formula (I) and $R^9$ is as defined in general formula (II) by reaction with a base followed by 1,2-dibromotetrachloroethane.

The base is suitably a strong non-nucleophilic base such as lithium diisopropylamide, which may be formed in situ from diisopropylamine and n-butyllithium at a temperature of −78° C. and in a solvent such as dry tetrahydrofuran.

When the base is lithium diisopropylamide, the reaction between the base and the compound of general formula (XII) may also be carried out at temperature of about −78° C., following which the 1,2-dibromotetrachloroethane may be added and the reaction mixture allowed to warm to about 10-30° C., typically 15-25° C., or room temperature.

In some cases, compounds of general formula (XI) and (XVI) may be prepared from compounds of general formula (IV) by an aminolysis reaction. Aminolysis reactions are well known and, for example, the preparation of primary sulfonamides by the reaction of sulfonyl chlorides with ammonia is described by Li et al, Synlett, (2006), 725. In this case the reaction was carried out in tetrahydrofuran. An alternative procedure using dichloromethane as solvent is described by Hu et al, J.A.C.S., (2008), 130, 13820 and Yuriev et al (European Journal of Medicinal Chemistry 39, 385) carried out the reaction in water.

Alternatively, however, compounds of general formula (XI) may be prepared from compounds of general formula (XIII):

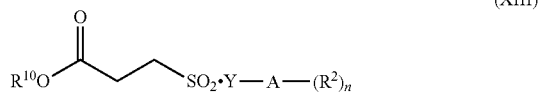
(XIII)

wherein Y, n, $R^2$ and A are as defined for general formula (I) and $R^{10}$ is $C_{1-6}$ alkyl; by reaction with a stoichiometric amount of sodium methoxide in an alcoholic solvent followed by excess hydroxylamine-O-sulfonic acid and sodium acetate. Typically the reaction with sodium methoxide will be carried out at a temperature of 15 to 30° C., usually room temperature, following which the reaction mixture is cooled to about −5 to 5° C., typically about 0° C. before the addition of the other reagents. Following the addition, the reaction mixture may again be allowed to warm to a temperature of 15 to 30° C., usually room temperature.

This method is particularly suitable for the synthesis of compounds of general formula (XI) in which A is an aryl or heteroaryl group and Y is a straight or branched hydrocarbon chain.

Compounds of general formula (XIII) may be prepared from compounds of general formula (XIV):

$X^4$—Y-A-$(R^2)_n$ (XIV)

wherein Y, n, $R^2$ and A are as defined for general formula (I); $X^4$ is a leaving group for example a halo group such as Cl, Br or I or a sulfonate, for example phenyl sulfonate, toluene sulfonate or methylsulfonate;
by reaction with sodium 3-alkoxy-3-oxopropane-1-sulfinate of formula (XV):

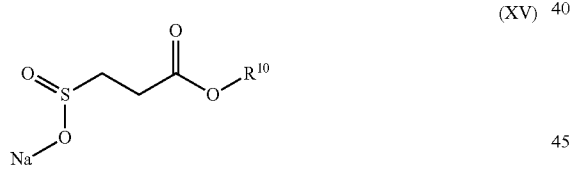
(XV)

where $R^{10}$ is as defined for general formula (XIII).

The reaction may be carried out in an organic solvent such as dimethylsulfoxide at a temperature of 15 to 30° C., typically at room temperature.

The synthesis of sodium 3-alkoxy-3-oxopropane-1-sulfinates of formula (XV) and their conversion to sulfonamides of general formula (XI) is described by Baskin & Wang, Tet. Lett., 43, 8479-8483 (2002). Compounds of general formulae (XIV) are well known and are either readily available or may be prepared by methods well known to those of skill in the art.

Compounds of general formula (XI) may also be prepared from compounds of general formula (IV) as defined above by reaction with aqueous ammonium hydroxide. The compound of general formula (IV) may be dissolved in a water-miscible solvent such as acetone and added to the aqueous ammonium hydroxide with cooling (for example to about 0° C.). The reaction may then be completed at a temperature of about 15 to 30° C., typically room temperature.

This method is particularly suitable for the synthesis of compounds of general formula (XI) in which Y is a bond and A is an aryl or heteroaryl group.

Compounds of general formula (IV) can also be converted to compounds of general formula (XI) by reaction with sulfamide. The reaction is typically carried out in a cyclic ether solvent such as dioxin at raised temperature, for example at the reflux temperature of the solvent. This method is particularly suitable for the synthesis of compounds of general formula (XI) in which Y is a bond and A is a carbocyclic or heterocyclic group.

A further method for the synthesis of compounds of general formula (XI) in which Y is $CH_2$ is by the reaction of a compound of general formula (XXII):

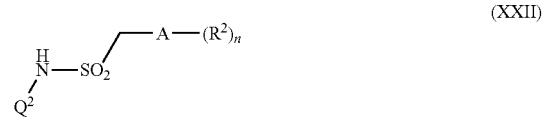
(XXII)

wherein A, $R^2$ and n are as defined for general formula (I) and $Q^2$ is an amine protecting group.

Suitable protecting groups for amines are described T. W. Greene & P. G. M. Wuts, "Greene's Protective Groups in Organic Synthesis", Wiley-Interscience; 4th edition, 2006. Suitable examples of protecting groups $Q^2$ include benzyl and substituted benzyl groups, for example benzyl and especially 4-methoxybenzyl.

Compounds of general formula (XXII) may be prepared from compounds of general formula (XXIII):

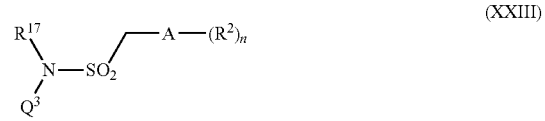
(XXIII)

wherein A, $R^2$ and n are as defined for general formula (I); $R^{17}$ is $C_{1-4}$ alkyl and $Q^3$ is phenyl or substituted phenyl;
by reaction with a compound of general formula (XXIV):

$Q^2$-$NH_2$ (XXIV)

wherein $Q^2$ is as defined above for general formula (XXII).

The reaction may be conducted in a basic solvent such as N-methylpyrrolidinone at elevated temperature, for example about 100-150° C.

Compounds of general formula (XXIV) are either readily available or may be prepared by methods well known to those of skill in the art.

Compounds of general formula (XXIII) may be prepared from compounds of general formula (XXV):

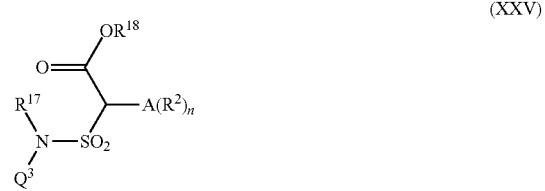
(XXV)

wherein A, $R^2$ and n are as defined for general formula (I); $R^{17}$ and $Q^3$ are as defined for general formula (XXIII); and $R^{18}$ is $C_{1-6}$ alkyl;

by reaction with a base, for example sodium hydroxide. The reaction may take place in a water miscible solvent such as methanol and at a temperature of 40-60° C., typically 50° C.

A compound of general formula (XXV) may be prepared from a compound of general formula (XXVI):

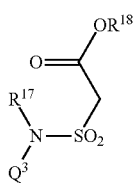
(XXVI)

wherein $Q^3$ and $R^{17}$ are as defined for general formula (XXIII) and $R^{18}$ is as defined for general formula (XXV);

by reaction with a compound of general formula (XXVII)

(XXVII)

wherein A, $R^2$ and n are as defined for general formula (I) and $X^4$ is a leaving group, especially a halogen such as bromine;

under basic conditions.

The basic conditions may be catalysed by a palladium catalyst such as $Pd(PPh_3)_4$ and the basic conditions may be provided by the use of a metal hydride, for example sodium hydride and the reaction may be conducted under an inert atmosphere, for example nitrogen, at elevated temperature, typically abut 6-80° C.

A compound of general formula (XXVI) may be prepared by the reaction of a compound of general formula (XXVIII):

(XXVIII)

wherein $Q^3$ and $R^{17}$ are as defined for general formula (XXIII);

with a compound of general formula (XXIX):

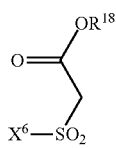
(XXIX)

wherein $R^{18}$ is as defined for general formula (XXV); and $X^5$ is a leaving group, especially a halogen such as chlorine.

The reaction may take place in an organic solvent such as dichloromethane at a temperature of 15-30° C., typically room temperature.

Compounds of general formulae (XXVIII) and (XXIX) are readily available or may be prepared by methods familiar to those of skill in the art.

As shown in Scheme 1, compounds of general formula (II) in which $R^{11}$ is hydrogen may also be prepared from compounds of general formula (XVII):

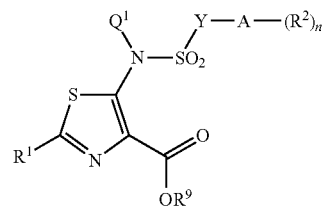
(XVII)

wherein $R^1$, Y, n, $R^2$ and A are as defined for general formula (I); $R^9$ is as defined for general formula (II) and $Q^1$ is an amine protecting group;

with a strong acid.

Suitable protecting groups for amines are described T. W. Greene & P. G. M. Wuts, "Greene's Protective Groups in Organic Synthesis", Wiley-Interscience; 4th edition, 2006. Suitable examples of protecting groups $Q^1$ include benzyl and substituted benzyl groups, for example benzyl and 4-methoxybenzyl.

The acid may be sulphuric acid and the reaction may be carried out in an organic solvent such as dichloromethane. Typically, the reaction mixture will be cooled to about 0° C. while the acid is added but then allowed to warm to 15 to 30° C., suitably room temperature.

Compounds of general formula (XVII) may be prepared from compounds of general formula (XVIII):

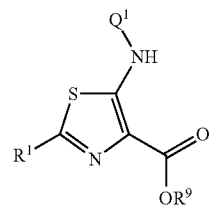
(XVIII)

wherein $R^1$ is as defined for general formula (I), $R^9$ is as defined for general formula (II) and $Q^1$ is as defined for general formula (XVII);

by reaction with a compound of general formula (IV) as defined above.

The compound of general formula (XVIII) may first be treated with a strong base such as an alkali metal hydride, typically sodium hydride, under anhydrous conditions, for example in a dry organic solvent, for example a cyclic ether such as tetrahydrofuran and following this, the compound of general formula (IV) may be added to the reaction mixture.

A compound of general formula (XVIII) may be prepared from a compound of general formula (IX) by reaction with an isothiocyanate compound of general formula (XIX):

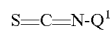
S=C=N-$Q^1$ (XIX)

wherein $Q^1$ is as defined for general formula (XVII);
under basic conditions.

The reaction may be carried out at a temperature of about 15-30° C., typically room temperature under anhydrous conditions, for example in a dry organic solvent such as tetrahydrofuran. The base may be an alkali metal alkoxide, for example sodium or potassium tert-butoxide. Typically, the compound of general formula (IX) is mixed with the base in the solvent, following which the compound of general formula (XIX) is added and the mixture stirred until the reaction is complete.

Compounds of general formulae (IX) and (XIX) are well known and are either readily available or may be prepared by methods well known to those of skill in the art.

Compounds of general formula (I) may also be prepared by the methods shown in Scheme 2.

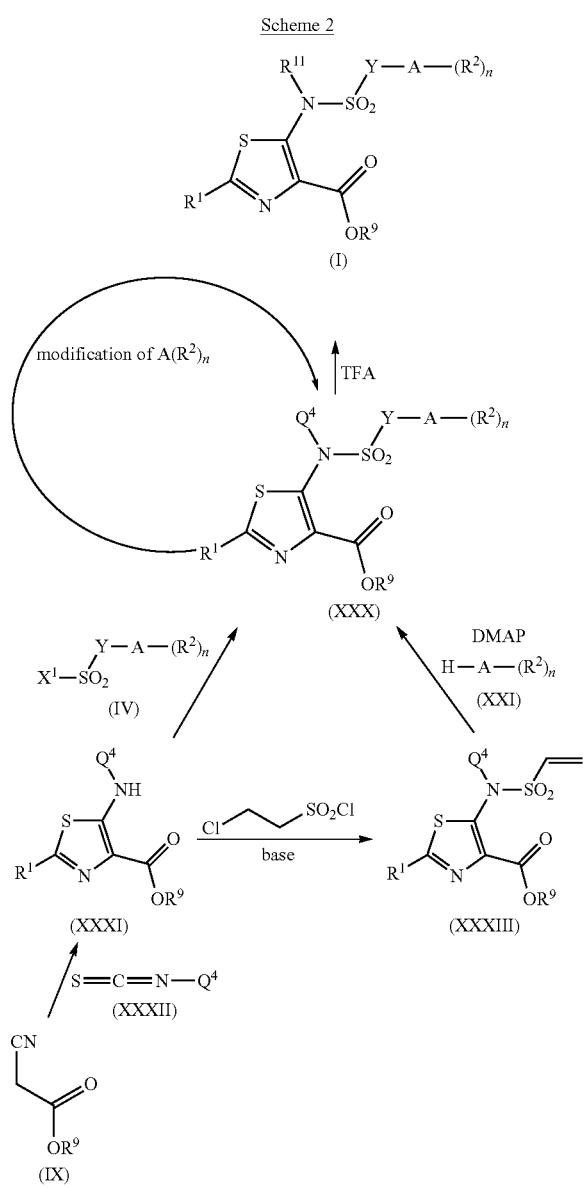

Compounds of general formula (I) may be prepared by deprotection of a compound of general formula (XXX):

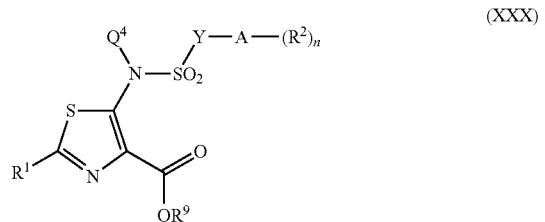

wherein $R^1$, Y, A, $R^2$ and n are as defined for general formula (I); $R^9$ is as defined for general formula (II) and $Q^4$ is an amine protecting group;
under acid conditions, for example using trifluoroacetic acid (TFA).

Suitable protecting groups for amines are described T. W. Greene & P. G. M. Wuts, "Greene's Protective Groups in Organic Synthesis", Wiley-Interscience; 4th edition, 2006. Suitable examples of protecting groups $Q^4$ include benzyl and substituted benzyl groups, for example benzyl and especially 4-methoxybenzyl.

The protecting group is removed under acidic conditions, for example using TFA, which may be aqueous TFA, for example 95% TFA(aq). The deprotection reaction may be carried out at a temperature of about 15-30° C., typically room temperature.

As shown in Scheme 2, compounds of general formula (XXX) may be converted into other compounds of general formula (XXX) by modification of the moiety Y-A-$(R^2)_n$. For example a cyclic group A-$(R^2)$, may be modified or replaced with an alternative group A-$(R^2)_n$. A number of such processes are illustrated in the examples below.

A compound of general formula (XXX) may be prepared by the reaction of a compound of general formula (XXXI):

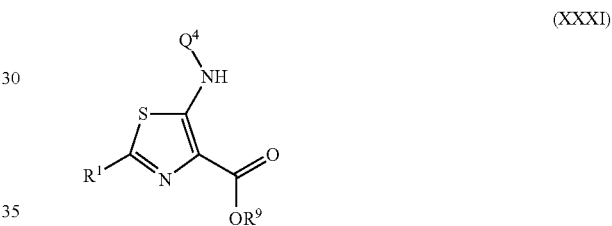

wherein $R^1$ is as defined for general formula (I); $R^9$ is as defined for general formula (II); and $Q^4$ is as defined for general formula (XXX);
with a compound of general formula (IV) as defined above; and a base.

The reaction is typically conducted under anhydrous conditions in a cyclic ether solvent such as tetrahydrofuran or a mixture of tetrahydrofuran and a crown ether such as 15-crown-5. Suitable bases include strong bases such as alkali metal hydrides, typically sodium hydride and the reaction may be carried out at 15-30° C., suitably at room temperature.

A compound of general formula (XXXI) may be prepared from a compound of general formula (IX) as defined above by reaction with an isocyanate compound of general formula (XXXII):

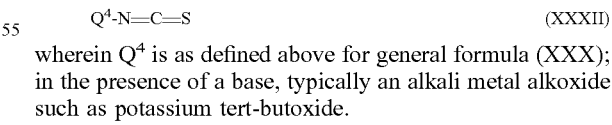

wherein $Q^4$ is as defined above for general formula (XXX); in the presence of a base, typically an alkali metal alkoxide such as potassium tert-butoxide.

The reaction may be carried out under anhydrous conditions and in an organic solvent such as a cyclic ether, typically tetrahydrofuran.

Compounds of general formula (XXXII) are readily available or may be prepared by methods well known to those of skill in the art.

An alternative method for the synthesis of a compound of general formula (XXX) in which Y is —$CH_2CH_2$— is by the reaction of a compound of general formula (XXXIII):

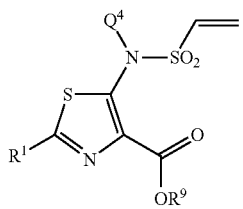

(XXXIII)

wherein $R^1$ is as defined in general formula (I); $R^9$ is as defined in general formula (II) and $Q^4$ is as defined in general formula (XXX);
with a compound of general formula (XXI) as defined above in the presence of a 4-dimethylaminopyridine (DMAP).

Suitably the reaction is conducted in an alcoholic solvent such as n-propanol and at elevated temperature, for example 80-100° C., suitably 90° C.

A compound of general formula (XXXII) may be prepared from a compound of general formula (XXXI) as defined above by reaction with a base followed by 2-chloroethanesulfonyl chloride. Suitable bases include alkali metal hydrides such as sodium hydride and the reaction may be conducted at a temperature of about 15-30° C., or room temperature. The reaction is typically conducted under anhydrous conditions in a cyclic ether solvent such as tetrahydrofuran or a mixture of tetrahydrofuran and a crown ether such as 15-crown-5.

As already discussed, the compound of general formula (I) are inhibitors or metallo-β-lactamase (MBL) enzymes and are therefore useful for removing or reducing resistance of Gram-negative bacteria to antibiotics.

Therefore, in a further aspect of the invention there is provided a compound of general formula (I) or 5-(4-aminophenylsulfonamido)thiazole-4-carboxylic acid for use in medicine, particularly in the removal or reduction of antibiotic resistance in Gram-negative bacteria.

In addition there is provided the use of a compound of general formula (I) or 5-(4-aminophenylsulfonamido)thiazole-4-carboxylic acid in the preparation of an agent for removing or reducing resistance of Gram-negative bacteria to antibiotics.

There is also provided a method for reducing or removing resistance of Gram-negative bacteria to antibiotics, the method comprising administering to a patient in need of such treatment an effective amount of a compound of general formula (I) or 5-(4-aminophenylsulfonamido)thiazole-4-carboxylic acid.

The Gram-negative bacteria of which antibiotic resistance can be removed using the compounds of general formula (I) are bacteria which produce metallo-β-lactamases, which may be metallo-β-lactamases of subclasses B1, B2 or B3, for example IMP-type (including IMP-1), VIM-type (including VIM-1 and VIM-2) and NDM-type (including NDM-1) enzymes.

Typical examples of such bacteria include Enterobacteriaceae (such as *Klebsiella pneumonia* and *Escherichia coli*), Pseudomonadaceae (such as *Pseudomonas aeruginosa* and *Burkholderia cepacia*) and *Acinetobacter baumannii*.

In another aspect of the invention there is provided a product comprising a compound of general formula (I) or 5-(4-aminophenylsulfonamido)thiazole-4-carboxylic acid in combination with an antibiotic agent.

In a further aspect of the invention, there is provided a product comprising a compound of general formula (I) or 5-(4-aminophenylsulfonamido)thiazole-4-carboxylic acid in combination with an antibiotic agent for the treatment of a bacterial infection, particularly a bacterial infection which is resistant to treatment with the antibiotic when used alone.

In using the product, the compound of general formula (I) or 5-(4-aminophenylsulfonamido)thiazole-4-carboxylic acid may be administered simultaneously with the antibiotic or the two agents may be administered separately, either immediately after one another or at different times.

The antibiotic agent may be a β-lactam antibiotic, for example an antibiotic selected from carbapenems, penicillins, cephalosporins and penems.

Examples of carbapenem antibiotics include Imipenem, Meropenem, Ertapenem, Doripenem and Biapenem.

Examples of penicillins include Amoxicillin, Ampicillin, Ticarcillin, Piperacillin and Cloxacillin Examples of cephalosporins include Cefazolin, Ceftriaxone, Ceftazidine and Ceftobiprole.

Examples of penems include Faropenem.

In a further aspect of the invention there is provided the use of a compound of general formula (I) or 5-(4-aminophenylsulfonamido)thiazole-4-carboxylic acid in the preparation of an agent for the treatment of a bacterial infection, particularly a bacterial infection which is resistant to treatment with the antibiotic when used alone.

The invention also provides a method for the treatment of a bacterial infection, the method comprising administering to a patient in need of such treatment an effective amount of a compound of general formula (I) or 5-(4-aminophenylsulfonamido)thiazole-4-carboxylic acid.

The bacterial infection is typically a bacterial infection which is resistant to treatment with the antibiotic when used alone.

Suitable antibiotics are as set out above.

The compound of general formula (I) will generally be formulated for administration by a desired route.

In a further aspect of the invention, there is provided a pharmaceutical or veterinary composition comprising a compound of general formula (I) or 5-(4-aminophenylsulfonamido)thiazole-4-carboxylic acid and a pharmaceutically or veterinarily acceptable excipient or carrier.

In some embodiments, the composition may also comprise an antibiotic agent, especially an antibiotic agent as discussed above.

The excipient and/or the carrier, or, if more than one be present, each of the excipients and carriers, must be acceptable in the sense of being compatible with the other ingredients of the formulation and not deleterious to the recipient.

The formulations include those suitable for oral, rectal, nasal, topical (including eye drops, buccal and sublingual), vaginal or parenteral (including subcutaneous, intramuscular, intravenous and intradermal) administration and may be prepared by any methods well known in the art of pharmacy.

The route of administration will depend upon the condition to be treated but preferred compositions are formulated for oral, parenteral or topical administration, especially oral or parenteral administration and more especially parenteral administration, especially intravenous administration.

The composition may be prepared by bringing into association the above defined active agent with the carrier. In general, the formulations are prepared by uniformly and intimately bringing into association the active agent with liquid carriers or finely divided solid carriers or both, and then if necessary shaping the product. The invention extends to methods for preparing a pharmaceutical composition comprising bringing a compound of general formula (I) or 5-(4-aminophenylsulfonamido)thiazole-4-carboxylic acid in conjunction or association with a pharmaceutically or veterinarily acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the active agent in a free flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the active agent in a flavoured base, usually sucrose and acacia or tragacanth; pastilles comprising the active agent in an inert base such as gelatin and glycerin, or sucrose and acacia; and mouthwashes comprising the active agent in a suitable liquid carrier.

For topical application to the skin, compounds of general formula (I) or 5-(4-aminophenylsulfonamido)thiazole-4-carboxylic acid may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Parenteral formulations will generally be sterile.

In a further aspect of the invention there is provided a process for the preparation of a pharmaceutical or veterinary composition, the process comprising admixing a compound of general formula (I) or 5-(4-aminophenylsulfonamido) thiazole-4-carboxylic acid, a pharmaceutically acceptable excipient or carrier and optionally an antibiotic agent.

Typically, the dose of the compound will be about 0.01 to 100 mg/kg; so as to maintain the concentration of drug in the plasma at a concentration effective to inhibit MBL enzymes. The precise amount of a compound of general formula (I) or 5-(4-aminophenylsulfonamido)thiazole-4-carboxylic acid which is therapeutically effective, and the route by which such compound is best administered, is readily determined by one of ordinary skill in the art by comparing the blood level of the agent to the concentration required to have a therapeutic effect.

Since the compounds of general formula (I) are inhibitors of MBL enzymes, they can also be used in a method for the detection of bacteria which express MBL enzymes, i.e. which are wholly or partially resistant to β lactam antibiotics.

Therefore in a further aspect of the invention there is provided a method of determining whether bacteria express MBL enzymes, the method comprising
i. contacting a test sample suspected of containing an MBL enzyme with a compound of general formula (I);
ii. detecting MBL enzyme activity in the test sample.

MBL enzyme activity may be detected by adding to the test sample a detection solution comprising a detector compound containing a β lactam ring, for example a β lactam antibiotic, including any of the compounds discussed above. If the test sample comprises bacteria which express an MBL enzyme, this enzyme will hydrolyse the β lactam ring of the detector compound.

The hydrolysis can be detected in a number of ways including spectrophotometric methods. One simple way of detecting the hydrolysis reaction is to include in the detection solution a pH indicator which changes colour according to the acidity of its environment. Since the hydrolysis of the β lactam ring leads to the production of a carboxylic acid, the pH of the detection solution will change on contact with bacteria which produce MBL enzymes and this can be visualised using a pH indicator.

As just described, suitable detector compounds include antibiotics, for example any of the compounds mentioned above as being suitable for use in combination with the compounds of general formula (I).

The test sample may comprise bacteria suspected of expressing an MBL enzyme, for example a liquid sample comprising a suspension of such bacteria.

The bacteria may express any MBL enzyme, for example an enzyme of subclass B1, B2 or B3. However, in many cases the enzyme expressed is of subclass B1, for example an IMP-type, VIM-type or NDM-type enzyme.

Suitably, a compound of general formula (I) is added to the test sample, typically at a concentration of between 10 nM and 10 µM.

Typically a control sample is also provided which is identical to the test sample; no compound of general formula (I) is added to the control sample.

The presence and amount of MBL enzyme in the sample can be determined by adding the detector compound to the test sample and to the control sample and detecting any difference in the degree of hydrolysis seen in the test and control samples.

For example, when a pH indicator is used as a means of detecting hydrolysis, the presence of MBL enzyme can be determined by a difference in the colour of the test and control samples.

In a further aspect of the invention, there is provided a kit for carrying out the method of determining whether bacteria express MBL enzymes, the kit comprising:
i. a compound of general formula (I) as defined above;
ii. a detector compound containing a β lactam ring; and
iii. means for detecting hydrolysis of the β lactam ring of the detector compound.

Suitably these agents will be provided in suitable containers. The compound of general formula (I) may be any of the compounds described above; and the detector compound and the means for detecting hydrolysis are suitably the agents described above for the method of determining whether bacteria express MBL enzymes.

EXAMPLES

The invention will now be described in greater detail with reference to the following examples.

Compounds Synthesised

Tables 1 and 2 set out the compounds synthesised in the examples.

TABLE 1

Compounds of formula (IA), i.e. compounds of formula (I) in which R1 is H.

(IA)

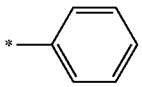

| No | Z | Name |
|---|---|---|
| 1 | 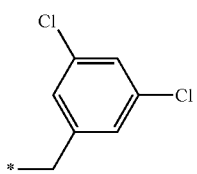 | 5-benzenesulfonamido-1,3-thiazole-4-carboxylic acid; |
| 2 | 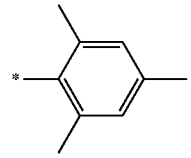 | 5-{[(3,5-dichlorophenyl)methyl]sulfonamido}-1,3-thiazole-4-carboxylic acid; |
| 3 | 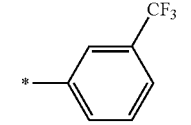 | 5-(2,4,6-trimethylphenylsulfonamido)thiazole-4-carboxylic acid; |
| 4 | 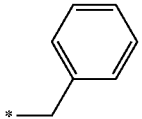 | 5-{[3-(trifluoromethyl)phenyl]sulfonamido}-1,3-thiazole-4-carboxylic acid; |
| 5 | 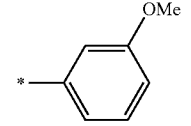 | 5-(phenylmethylsulfonamido)thiazole-4-carboxylic acid; |
| 6 | 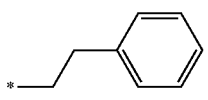 | 5-(3-methoxyphenylsulfonamido)thiazole-4-carboxylic acid; |
| 7 | 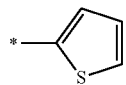 | 5-(2-phenylethylsulfonamido)thiazole-4-carboxylic acid; |
| 8 | | 5-(thiophene-2-sulfonamido)thiazole-4-carboxylic acid; |

TABLE 1-continued

Compounds of formula (IA), i.e. compounds of formula (I) in which R1 is H.

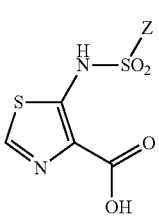
(IA)

| No | Z | Name |
|---|---|---|
| 9 | 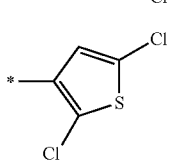 | 5-(4,5-dichlorothiophene-2-sulfonamido)thiazole-4-carboxylic acid; |
| 10 | 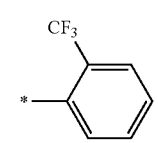 | 5-(2,5-dichlorothiophene-3-sulfonamido)thiazole-4-carboxylic acid; |
| 11 |  | 5-(2-(trifluoromethyl)phenylsulfonamido)thiazole-4-carboxylic acid; |
| 12 | 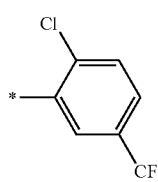 | 5-(4-(trifluoromethyl)phenylsulfonamido)thiazole-4-carboxylic acid; |
| 13 | 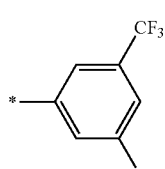 | 5-(2-chloro-5-(trifluoromethyl)phenylsulfonamido)thiazole-4-carboxylic acid; |
| 14 | 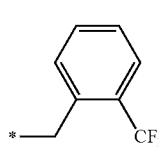 | 5-(3,5-bis(trifluoromethyl)phenylsulfonamido)thiazole-4-carboxylic acid; |
| 15 | 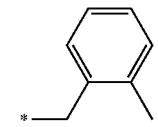 | 5-({[2-(trifluoromethyl)phenyl]methyl}sulfonamido)-1,3-thiazole-4-carboxylic acid; |
| 16 | 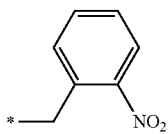 | 5-{[(2-methylphenyl)methyl]sulfonamido}-1,3-thiazole-4-carboxylic acid; |
| 17 |  | 5-((2-nitrophenyl)methylsulfonamido)thiazole-4-carboxylic acid; |

TABLE 1-continued

Compounds of formula (IA), i.e. compounds of formula (I) in which R1 is H.

(IA)

| No | Z | Name |
|---|---|---|
| 18 | 2-bromobenzyl | 5-{[(2-bromophenyl)methyl]sulfonamido}-1,3-thiazole-4-carboxylic acid; |
| 19 | 5-chlorothiophen-2-yl | 5-(5-chlorothiophene-2-sulfonamido)thiazole-4-carboxylic acid; |
| 20 | 5-phenylthiophen-2-yl | 5-(5-phenylthiophene-2-sulfonamido)thiazole-4-carboxylic acid; |
| 21 | thiophen-3-yl | 5-(thiophene-3-sulfonamido)thiazole-4-carboxylic acid; |
| 22 | 2,5-dimethylthiophen-3-yl | 5-(2,5-dimethylthiophene-3-sulfonamido)thiazole-4-carboxylic acid; |
| 23 | biphenyl-2-yl | 5-([1,1'-biphenyl]-2-ylsulfonamido)thiazole-4-carboxylic acid; |
| 24 | 2-aminobenzyl | 5-((2-aminophenyl)methylsulfonamido)thiazole-4-carboxylic acid; |
| 25 | 2-acetamidobenzyl | 5-((2-acetamidophenyl)methylsulfonamido)thiazole-4-carboxylic acid; |
| 26 | 2-benzamidobenzyl | 5-((2-benzamidophenyl)methylsulfonamido)thiazole-4-carboxylic acid; |

TABLE 1-continued

Compounds of formula (IA), i.e. compounds of formula (I) in which R1 is H.

(IA)

| No | Z | Name |
|---|---|---|
| 27 | (2-styryl benzyl, E) | (E)-5-((2-styrylphenyl)methylsulfonamido)thiazole-4-carboxylic acid; |
| 28 | (2-(3-(dimethylamino)-3-oxoprop-1-en-1-yl)benzyl, E) | (E)-5-((2-(3-(dimethylamino)-3-oxoprop-1-en-1-yl)phenyl)methylsulfonamido)thiazole-4-carboxylic acid; |
| 29 | (2-phenylbenzyl) | 5-([1,1'-biphenyl]-2-ylmethylsulfonamido)thiazole-4-carboxylic acid; |
| 30 | (2-(trifluoromethoxy)benzyl) | 5-((2-(trifluoromethoxy)phenyl)methylsulfonamido)thiazole-4-carboxylic acid; |
| 31 | (3-(trifluoromethyl)benzyl) | 5-((3-(trifluoromethyl)phenyl)methylsulfonamido)thiazole-4-carboxylic acid; |
| 32 | (3-bromobenzyl) | 5-((3-bromophenyl)methylsulfonamido)thiazole-4-carboxylic acid; |
| 33 | (3-cyanobenzyl) | 5-((3-cyanophenyl)methylsulfonamido)thiazole-4-carboxylic acid; |
| 34 | (2-chlorobenzyl) | 5-((2-chlorophenyl)methylsulfonamido)thiazole-4-carboxylic acid; |

TABLE 1-continued

Compounds of formula (IA), i.e. compounds of formula (I) in which R1 is H.

(IA)

| No | Z | Name |
|---|---|---|
| 35 | 4-nitrophenyl | 5-(4-nitrophenylsulfonamido)thiazole-4-carboxylic acid; |
| 36 | 4-aminophenyl | 5-(4-aminophenylsulfonamido)thiazole-4-carboxylic acid; |
| 37 | 5-[5-(trifluoromethyl)-1,2-oxazol-3-yl]thiophen-2-yl | 5-({5-[5-(trifluoromethyl)-1,2-oxazol-3-yl]thiophen-2-yl}sulfonamido)-1,3-thiazole-4-carboxylic acid; |
| 38 | 1-benzothiophene-2-yl | 5-(1-benzothiophene-2-sulfonamido)-1,3-thiazole-4-carboxylic acid; |
| 39 | 5-methylthiophen-2-yl | 5-[(5-methylthiophen-2-yl)sulfonamido]-1,3-thiazole-4-carboxylic acid; |
| 40 | 5-bromothiophen-2-yl | 5-[(5-bromothiophen-2-yl)sulfonamido]-1,3-thiazole-4-carboxylic acid; |
| 41 | 1-benzothiophene-3-yl | 5-(1-benzothiophene-3-sulfonamido)-1,3-thiazole-4-carboxylic acid; |
| 42 | 4-bromo-2,5-dichlorothiophen-3-yl | 5-[(4-bromo-2,5-dichlorothiophen-3-yl)sulfonamido]-1,3-thiazole-4-carboxylic acid; |
| 43 | -NH-CH2-(2-chlorophenyl) | 5-({[(2-chlorophenyl)methyl]sulfamoyl}amino)-1,3-thiazole-4-carboxylic acid; |
| 44 | -NH-CH2-(3-trifluoromethylphenyl) | 5-[({[3-(trifluoromethyl)phenyl]methyl}sulfamoyl)amino]-1,3-thiazole-4-carboxylic acid; |

TABLE 1-continued

Compounds of formula (IA), i.e. compounds of formula (I) in which R1 is H.

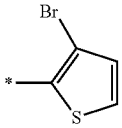

(IA)

| No | Z | Name |
|---|---|---|
| 45 | 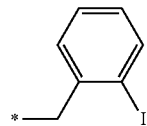 | 5-[(3-bromothiophen-2-yl)sulfonamido]-1,3-thiazole-4-carboxylic acid; |
| 46 | 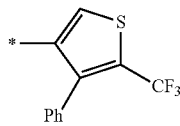 | 5-{[(2-iodophenyl)methyl]sulfonamido}-1,3-thiazole-4-carboxylic acid; |
| 47 | 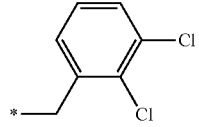 | 5-{[4-phenyl-5-(trifluoromethyl)thiophen-3-yl]sulfonamido}-1,3-thiazole-4-carboxylic acid; |
| 48 | 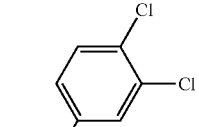 | 5-{[(2,3-dichlorophenyl)methyl]sulfonamido}-1,3-thiazole-4-carboxylic acid; |
| 49 | 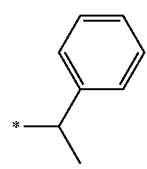 | 5-{[(3,4-dichlorophenyl)methyl]sulfonamido}-1,3-thiazole-4-carboxylic acid; |
| 60 | 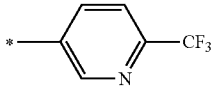 | 5-[(1-phenylethyl)sulfonamido]-1,3-thiazole-4-carboxylic acid; |
| 61 | 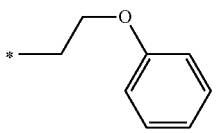 | 5-{[6-(trifluoromethyl)pyridin-3-yl]sulfonamido}-1,3-thiazole-4-carboxylic acid; |
| 62 | 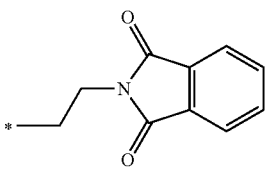 | 5-[(2-phenoxyethyl)sulfonamido]-1,3-thiazole-4-carboxylic acid; |
| 63 | | 5-{[2-(1,3-dioxo-2,3-dihydro-1H-isoindol-2-yl)ethyl]sulfonamido}-1,3-thiazole-4-carboxylic acid; |

TABLE 1-continued

Compounds of formula (IA), i.e. compounds of formula (I) in which R1 is H.

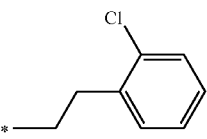

(IA)

| No | Z | Name |
|---|---|---|
| 64 | 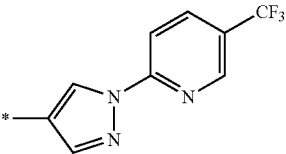 | 5-{[2-(2-chlorophenyl)ethyl]sulfonamido}-1,3-thiazole-4-carboxylic acid; |
| 65 | 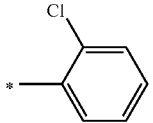 | 5-({1-[5-(trifluoromethyl)pyridin-2-yl]-1H-pyrazol-4-yl}sulfonamido)-1,3-thiazole-4-carboxylic acid; |
| 66 | 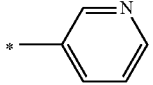 | 5-[(2-chlorophenyl)sulfonamido]-1,3-thiazole-4-carboxylic acid; |
| 67 | 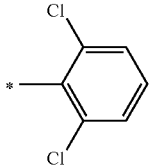 | 5-(pyridine-3-sulfonamido)-1,3-thiazole-4-carboxylic acid; |
| 68 | 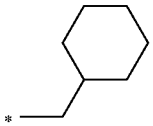 | 5-[(2,6-dichlorophenyl)sulfonamido]-1,3-thiazole-4-carboxylic acid; |
| 69 | 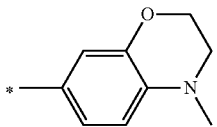 | 5-(cyclohexylmethyl)sulfonamido-1,3-thiazole-4-carboxylic acid; |
| 70 | 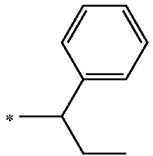 | 5-[(4-methyl-3,4-dihydro-2H-1,4-benzoxazin-7-yl)sulfonamido]-1,3-thiazole-4-carboxylic acid; |
| 71 | | 5-[(1-phenylpropyl)sulfonamido]-1,3-thiazole-4-carboxylic acid; |

TABLE 1-continued

Compounds of formula (IA), i.e. compounds of formula (I) in which R1 is H.

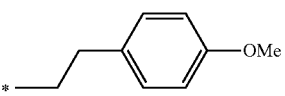

(IA)

| No | Z | Name |
|---|---|---|
| 72 | 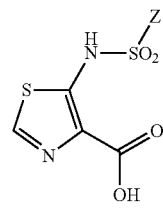 | 5-{[2-(4-methoxyphenyl)ethyl]sulfonamido}-1,3-thiazole-4-carboxylic acid; |
| 73 | 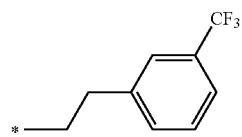 | 5-({2-[3-(trifluoromethyl)phenyl]ethyl}sulfonamido)-1,3-thiazole-4-carboxylic acid; |
| 74 | 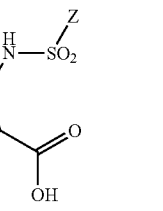 | 5-{[2-(4-chlorophenyl)ethyl]sulfonamido}-1,3-thiazole-4-carboxylic acid; |
| 75 | 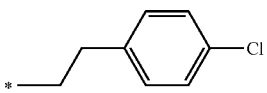 | 5-[(piperidine-1-sulfonyl)amino]-1,3-thiazole-4-carboxylic acid; |
| 76 |  | 5-[(phenylsulfamoyl)amino]-1,3-thiazole-4-carboxylic acid; |
| 77 | 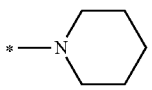 | 5-{[benzyl(methyl)sulfamoyl]amino}-1,3-thiazole-4-carboxylic acid; |
| 78 |  | 5-[(4-acetamidophenyl)sulfonamido]-1,3-thiazole-4-carboxylic acid; |
| 79 | 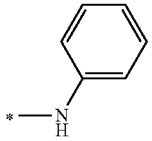 | 5-[(2-methoxyphenyl)sulfonamido]-1,3-thiazole-4-carboxylic acid; |
| 80 |  | 5-(1,2,3,4-tetrahydronaphthalene-1-sulfonamido)-1,3-thiazole-4-carboxylic acid; |

TABLE 1-continued

Compounds of formula (IA), i.e. compounds of formula (I) in which R1 is H.

(IA)

| No | Z | Name |
|---|---|---|
| 81 | (5-methyl-1-phenyl-1H-pyrazol-4-yl, attached at 4-position) | 5-[(5-methyl-1-phenyl-1H-pyrazol-4-yl)sulfonamido]-1,3-thiazole-4-carboxylic acid; |
| 82 | cyclopropylmethyl | 5-(cyclopropylmethyl)sulfonamido-1,3-thiazole-4-carboxylic acid; |
| 83 | (2-methoxyphenyl)methyl | 5-{[(2-methoxyphenyl)methyl]sulfonamido}-1,3-thiazole-4-carboxylic acid; |
| 84 | 2-(2-methoxyphenyl)ethyl | 5-{[2-(2-methoxyphenyl)ethyl]sulfonamido}-1,3-thiazole-4-carboxylic acid; |
| 85 | 2-(3-methoxyphenyl)ethyl | 5-{[2-(3-methoxyphenyl)ethyl]sulfonamido}-1,3-thiazole-4-carboxylic acid; |
| 86 | 2-(3-chlorophenyl)ethyl | 5-{[2-(3-chlorophenyl)ethyl]sulfonamido}-1,3-thiazole-4-carboxylic acid; |
| 87 | 2-methanesulfonylphenyl | 5-[(2-methanesulfonylphenyl)sulfonamido]-1,3-thiazole-4-carboxylic acid; |
| 88 | N-methyl-N-phenylamino | 5-{[methyl(phenyl)sulfamoyl]amino}-1,3-thiazole-4-carboxylic acid; |
| 89 | 4-(morpholin-4-yl)phenyl | 5-{[4-(morpholin-4-yl)phenyl]sulfonamido}-1,3-thiazole-4-carboxylic acid; |

TABLE 1-continued

Compounds of formula (IA), i.e. compounds of formula (I) in which R1 is H.

(IA)

| No | Z | Name |
|---|---|---|
| 90 | 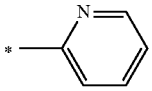 | 5-[(4-cyanophenyl)sulfonamido]-1,3-thiazole-4-carboxylic acid; |
| 91 | 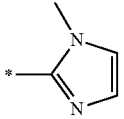 | 5-(pyridine-2-sulfonamido)-1,3-thiazole-4-carboxylic acid; |
| 92 | 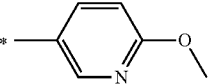 | 5-[(1-methyl-1H-imidazol-2-yl)sulfonamido]-1,3-thiazole-4-carboxylic acid; |
| 93 | 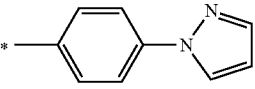 | 5-[(6-methoxypyridin-3-yl)sulfonamido]-1,3-thiazole-4-carboxylic acid; |
| 94 | 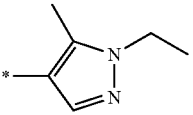 | 5-{[4-(1H-pyrazol-1-yl)phenyl]sulfonamido}-1,3-thiazole-4-carboxylic acid; |
| 95 | 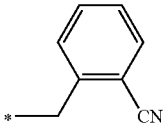 | 5-[(1-ethyl-5-methyl-1H-pyrazol-4-yl)sulfonamido]-1,3-thiazole-4-carboxylic acid; |
| 97 | 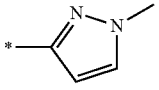 | 5-{[(2-cyanophenyl)methyl]sulfonamido}-1,3-thiazole-4-carboxylic acid; |
| 98 | 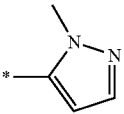 | 5-[(1-methyl-1H-pyrazol-3-yl)sulfonamido]-1,3-thiazole-4-carboxylic acid; |
| 99 | 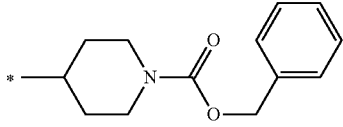 | 5-[(1-methyl-1H-pyrazol-5-yl)sulfonamido]-1,3-thiazole-4-carboxylic acid; |
| 100 | 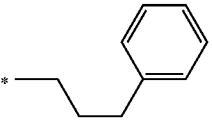 | 5-({1-[(benzyloxy)carbonyl]piperidin-4-yl}sulfonamido)-1,3-thiazole-4-carboxylic acid; |
| 101 |  | 5-[(3-phenylpropyl)sulfonamido]-1,3-thiazole-4-carboxylic acid; |

TABLE 1-continued

Compounds of formula (IA), i.e. compounds of formula (I) in which R1 is H.

(IA)

| No | Z | Name |
|---|---|---|
| 104 | (2,3-dihydro-1H-inden-1-yl) | 5-(2,3-dihydro-1H-indene-1-sulfonamido)-1,3-thiazole-4-carboxylic acid; |
| 105 | [4-(1-methyl-1H-pyrazol-5-yl)phenyl] | 5-{[4-(1-methyl-1H-pyrazol-5-yl)phenyl]sulfonamido}-1,3-thiazole-4-carboxylic acid; |
| 106 | 2-(1,2,3,4-tetrahydroquinolin-1-yl)ethyl | 5-{[2-(1,2,3,4-tetrahydroquinolin-1-yl)ethyl]sulfonamido}-1,3-thiazole-4-carboxylic acid; |
| 107 | 2-(N-phenylacetamido)ethyl | 5-{[2-(N-phenylacetamido)ethyl]sulfonamido}-1,3-thiazole-4-carboxylic acid; |
| 108 | [4-(3-oxomorpholin-4-yl)phenyl] | 5-{[4-(3-oxomorpholin-4-yl)phenyl]sulfonamido}-1,3-thiazole-4-carboxylic acid; |
| 109 | [4-(2-oxo-1,3-oxazolidin-3-yl)phenyl] | 5-{[4-(2-oxo-1,3-oxazolidin-3-yl)phenyl]sulfonamido}-1,3-thiazole-4-carboxylic acid; |
| 110 | (1,2-dimethyl-1H-imidazol-4-yl) | 5-[(1,2-dimethyl-1H-imidazol-4-yl)sulfonamido]-1,3-thiazole-4-carboxylic acid; |
| 111 | (oxan-4-ylmethyl) | 5-[(oxan-4-ylmethyl)sulfonamido]-1,3-thiazole-4-carboxylic acid; |

TABLE 1-continued

Compounds of formula (IA), i.e. compounds of formula (I) in which R1 is H.

(IA)

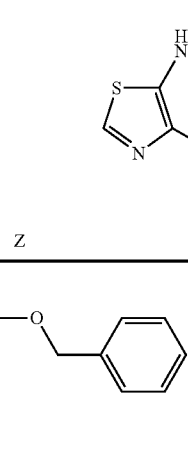

| No | Z | Name |
|---|---|---|
| 112 | 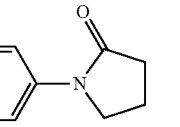 | 5-[({1-[(benzyloxy)carbonyl]piperidin-4-yl}methyl)sulfonamido]-1,3-thiazole-4-carboxylic acid; |
| 113 | 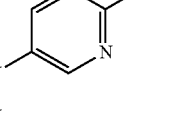 | 5-{[4-(2-oxopyrrolidin-1-yl)phenyl]sulfonamido}-1,3-thiazole-4-carboxylic acid; |
| 114 | 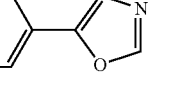 | 5-({1-[6-(trifluoromethyl)pyridin-3-yl]-1H-pyrazol-4-yl}sulfonamido)-1,3-thiazole-4-carboxylic acid; |
| 115 | 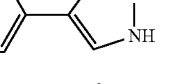 | 5-{[4-(1,3-oxazol-5-yl)phenyl]sulfonamido}-1,3-thiazole-4-carboxylic acid; |
| 116 | 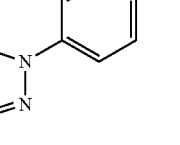 | 5-{[4-(1H-pyrazol-4-yl)phenyl]sulfonamido}-1,3-thiazole-4-carboxylic acid; |
| 117 | 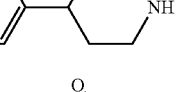 | 5-[(1-phenyl-1H-pyrazol-4-yl)sulfonamido]-1,3-thiazole-4-carboxylic acid; |
| 118 | 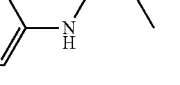 | 5-{[4-(piperidin-4-yl)phenyl]sulfonamido}-1,3-thiazole-4-carboxylic acid; |
| 119 | 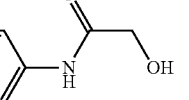 | 5-[(4-propanamidophenyl)sulfonamide]-1,3-thiazole-4-carboxylic acid; |
| 120 |  | 5-{[4-(2-hydroxyacetamido)phenyl]sulfonamido}-1,3-thiazole-4-carboxylic acid; |

TABLE 1-continued

Compounds of formula (IA), i.e. compounds of formula (I) in which R1 is H.

(IA)

| No | Z | Name |
|----|---|------|
| 121 | *-C₆H₄-NH-C(O)-NH-Me (para) | 5-({4-[(methylcarbamoyl)amino]phenyl}sulfonamido)-1,3-thiazole-4-carboxylic acid; |
| 122 | *-CH₂-(2,4-dichlorophenyl) | 5-{[(2,4-dichlorophenyl)methyl]sulfonamido}-1,3-thiazole-4-carboxylic acid; |
| 123 | *-CH₂-(2-fluorophenyl) | 5-{[(2-fluorophenyl)methyl]sulfonamido}-1,3-thiazole-4-carboxylic acid; |
| 124 | *-CH₂-(2,3-difluorophenyl) | 5-{[(2,3-difluorophenyl)methyl]sulfonamido}-1,3-thiazole-4-carboxylic acid; |
| 125 | *-C₆H₄-NH-C(O)-CH₂-OMe (para) | 5-{[4-(2-methoxyacetamido)phenyl]sulfonamido}-1,3-thiazole-4-carboxylic acid; |
| 126 | *-CH₂-(2,5-dichlorophenyl) | 5-{[(2,5-dichlorophenyl)methyl]sulfonamido}- 1,3-thiazole-4-carboxylic acid; |
| 127 | *-CH₂-(2,6-dichlorophenyl) | 5-{[(2,6-dichlorophenyl)methyl]sulfonamido}-1,3-thiazole-4-carboxylic acid; |
| 128 | *-CH₂-(2-chloro-6-fluorophenyl) | 5-{[(2-chloro-6-fluorophenyl)methyl]sulfonamido}-1,3-thiazole-4-carboxylic acid; |

TABLE 1-continued

Compounds of formula (IA), i.e. compounds of formula (I) in which R1 is H.

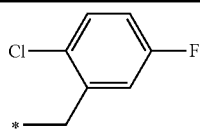

(IA)

| No | Z | Name |
|----|---|------|
| 129 | 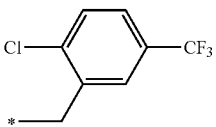 | 5-{[(2-chloro-4-fluorophenyl)methyl]sulfonamido}-1,3-thiazole-4-carboxylic acid; |
| 130 | 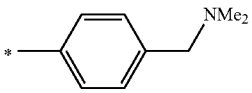 | 5-({[2-chloro-5-(trifluoromethyl)phenyl]methyl}sulfonamido)-1,3-thiazole-4-carboxylic acid; |
| 131 | 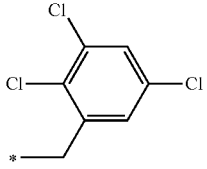 | 5-({4-[(dimethylamino)methyl]phenyl}sulfonamido)-1,3-thiazole-4-carboxylic acid; |
| 132 | 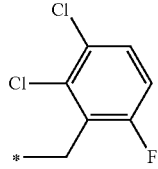 | 5-{[(2,3,5-trichlorophenyl)methyl]sulfonamido}-1,3-thiazole-4-carboxylic acid; |
| 133 | 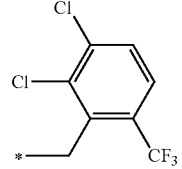 | 5-{[(2,3-dichloro-6-fluorophenyl)methyl]sulfonamido}-1,3-thiazole-4-carboxylic acid; |
| 134 | 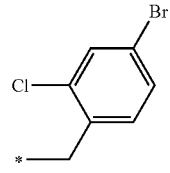 | 5-({[2,3-dichloro-6-(trifluoromethyl)phenyl]methyl}sulfonamido)-1,3-thiazole-4-carboxylic acid; |
| 135 | 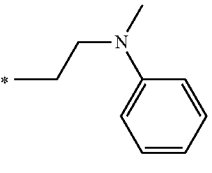 | 5-{[(4-bromo-2-chlorophenyl)methyl]sulfonamido}-1,3-thiazole-4-carboxylic acid; |
| 136 |  | 5-({2-[methyl(phenyl)amino]ethyl}sulfonamido)-1,3-thiazole-4-carboxylic acid; |

TABLE 1-continued

Compounds of formula (IA), i.e. compounds of formula (I) in which R1 is H.

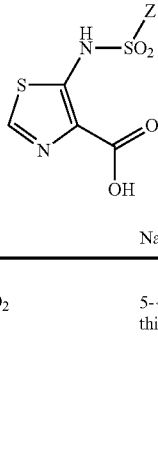

(IA)

| No | Z | Name |
|---|---|---|
| 137 | 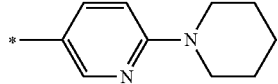 | 5-{[(4-nitrophenyl)methyl]sulfonamido}-1,3-thiazole-4-carboxylic acid; |
| 138 | 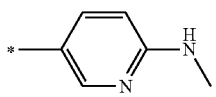 | 5-[6-(piperidin-1-yl)pyridin-3-ylsulfonamido]-1,3-thiazole-4-carboxylic acid; |
| 139 | 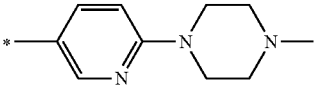 | 5-[6-(methylamino)pyridin-3-ylsulfonamido]-1,3-thiazole-4-carboxylic acid; |
| 140 | 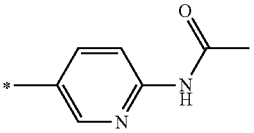 | 5-[6-(4-methylpiprazin-1-yl)piperidin-3-ylsulfonamido]-1,3-thiazole-4-carboxylic acid; |
| 141 | 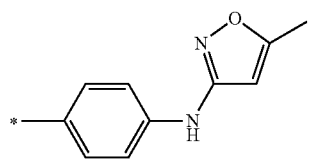 | 5-(6-acetamidopyridin-3-ylsulfonamido)-1,3-thiazole-4-carboxylic acid; |
| 142 | 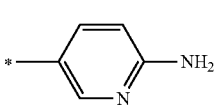 | 5-{4-[(5-methyl-1,2-oxazol-3-yl)amino]phenylsulfonamido}-1,3-thiazole-4-carboxylic acid; |
| 143 | 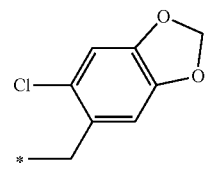 | 5-(6-aminopyridin-3-ylsulfonamido)-1,3-thiazole-4-carboxylic acid; |
| 144 | 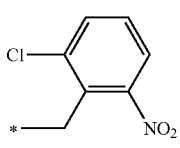 | 5-[(6-chloro-2H-1,3-benzodioxol-5-yl)methylsulfonamido]-1,3-thiazole-4-carboxylic acid; |
| 145 |  | 5-{[(2-chloro-6-nitrophenyl)methyl]sulfonamido}-1,3-thiazole-4-carboxylic acid; |

TABLE 1-continued

Compounds of formula (IA), i.e. compounds of formula (I) in which R1 is H.

(IA)

| No | Z | Name |
|---|---|---|
| 146 | 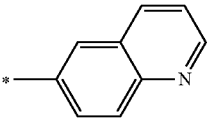 | 5-(quinoline-6-sulfonamido)-1,3-thiazole-4-carboxylic acid; |
| 147 | 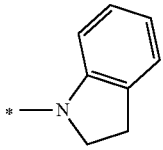 | 5-[(2,3-dihydroindole-1-sulfonyl)amino]-1,3-thiazole-4-carboxylic acid; |
| 148 | 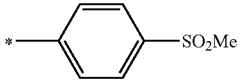 | 5-(4-methanesulfonylphenylsulfonamido)-1,3-thiazole-4-carboxylic acid; |
| 149 | 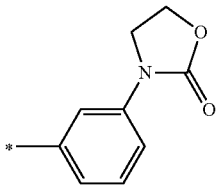 | 5-[3-(2-oxo-1,3-oxazolidin-3-yl)phenylsulfonamido]-1,3-thiazole-4-carboxylic acid; |
| 150 | 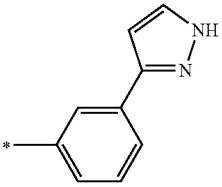 | 5-[3-(2H-pyrazol-3-yl)phenylsulfonamido]-1,3-thiazole-4-carboxylic acid; |
| 151 | 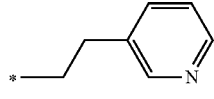 | 5-[2-(pyridin-3-yl)ethylsulfonamido]-1,3-thiazole-4-carboxylic acid; |
| 152 | 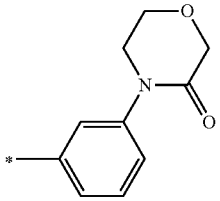 | 5-[3-(3-oxomorpholin-4-yl)phenylsulfonamido]-1,3-thiazole-4-carboxylic acid; |
| 153 | 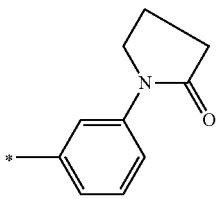 | 5-[3-(2-oxopyrrolidin-1-yl)phenylsulfonamido]-1,3-thiazole-4-carboxylic acid; |

TABLE 1-continued

Compounds of formula (IA), i.e. compounds of formula (I) in which R1 is H.

(IA)

| No | Z | Name |
|---|---|---|
| 154 | (5-pyridyl linked via * at 5-position; 2-position has NH to piperidin-4-yl) | 5-[6-(piperidin-4-ylamino)pyridin-3-ylsulfonamido]-1,3-thiazole-4-carboxylic acid; |
| 155 | (5-pyridyl linked via *; 2-NH-CH2CH2-N(CH3)2) | 5-(6-{[2-(dimethylamino)ethyl]amino}pyridin-3-ylsulfonamido)-1,3-thiazole-4-carboxylic acid; |
| 156 | (4-acetamidophenyl with CH2 linker at *) | 5-[(4-acetamidophenyl)methylsulfonamido]-1,3-thiazole-4-carboxylic acid; |
| 157 | (5-pyridyl linked via *; 2-piperazin-1-yl) | 5-[6-(piperazin-1-yl)pyridin-3-ylsulfonamido]-1,3-thiazole-4-carboxylic acid; |
| 158 | (5-pyridyl linked via *; 2-(4-aminopiperidin-1-yl)) | 5-[6-(4-aminopiperidin-1-yl)pyridin-3-ylsulfonamido]-1,3-thiazole-4-carboxylic acid; |
| 159 | (5-pyridyl linked via *; 2-(3-aminopyrrolidin-1-yl)) | 5-[6-(3-aminopyrrolidin-1-yl)pyridin-3-ylsulfonamido]-1,3-thiazole-4-carboxylic acid; |
| 160 | (5-pyridyl linked via *; 2-pyrrolidin-1-yl) | 5-[6-(pyrrolidin-1-yl)pyridin-3-ylsulfonamido]-1,3-thiazole-4-carboxylic acid; |
| 161 | (5-pyridyl linked via *; 2-(3-aminopiperidin-1-yl)) | 5-[6-(3-aminopiperidin-1-yl)pyridin-3-ylsulfonamido]-1,3-thiazole-4-carboxylic acid; |
| 162 | (5-pyridyl linked via *; 2-(1,4-diazepan-1-yl)) | 5-[6-(1,4-diazepan-1-yl)pyridin-3-ylsulfonamido]-1,3-thiazole-4-carboxylic acid; |

TABLE 1-continued

Compounds of formula (IA), i.e. compounds of formula (I) in which R1 is H.

(IA)

| No | Z | Name |
|---|---|---|
| 163 | (4-pyrrolidin-3-yloxyphenyl) | 5-[4-(pyrrolidin-3-yloxy)phenylsulfonamido]-1,3-thiazole-4-carboxylic acid; |
| 164 | (6-(3-aminoazetidin-1-yl)pyridin-3-yl) | 5-[6-(3-aminoazetidin-1-yl)pyridin-3-ylsulfonamido]-1,3-thiazole-4-carboxylic acid; |
| 165 | (6-(piperidin-4-yl)pyridin-3-yl) | 5-[6-(piperidin-4-yl)pyridin-3-ylsulfonamido]-1,3-thiazole-4-carboxylic acid; |
| 166 | (6-(1,2,3,6-tetrahydropyridin-4-yl)pyridin-3-yl) | 5-[6-(1,2,3,6-tetrahydropyridin-4-yl)pyridin-3-ylsulfonamido]-1,3-thiazole-4-carboxylic acid; |
| 167 | (6-[4-(2,2,2-trifluoroethyl)piperazin-1-yl]pyridin-3-yl) | 5-{6-[4-(2,2,2-trifluoroethyl)piperazin-1-yl]pyridin-3-ylsulfonamido}-1,3-thiazole-4-carboxylic acid |
| X1 168 | 1-(2-chlorophenyl)ethyl | 5-[1-(2-chlorophenyl)ethylsulfonylamino]thiazole-4-carboxylic acid Enantiomer 1 |
| X2 169 | 1-(2-chlorophenyl)ethyl | 5-[1-(2-chlorophenyl)ethylsulfonylamino]thiazole-4-carboxylic acid Enantiomer 2 |
| X3 170 | 3-pyridylmethyl | 5-(3-pyridylmethylsulfonylamino)thiazole-4-carboxylic acid |
| X4 171 | isoindolin-5-ylmethyl | 5-(isoindolin-5-ylmethylsulfonylamino)thiazole-4-carboxylic acid |

TABLE 1-continued

Compounds of formula (IA), i.e. compounds of formula (I) in which R1 is H.

(IA)

| No | Z | Name |
|---|---|---|
| X5 172 | | S-5-[[4-[1-(2-amino-2-phenyl-acetyl)-4-piperidyl]phenyl]sulfonylamino]thiazole-4-carboxylic acid |
| X6 173 | | R-5-[[4-[1-(2-amino-2-phenyl-acetyl)-4-piperidyl]phenyl]sulfonylamino]thiazole-4-carboxylic acid |
| X7 174 | | 5[[4(2-aminoacetyl)amino]phenyl]sulfonylamino]thiazole-4-carboxylic acid |
| X8 175 | | 5-[(4-acetamido-3-fluoro-phenyl)sulfonylamino]thiazole-4-carboxylic acid |
| X9 176 | | 5-[[4-[(2-hydroxy-2-methyl-propanoyl)amino]phenyl]sulfonylamino]thiazole-4-carboxylic acid |
| X10 177 | | 5-[[4-[(2-hydroxy-2-phenyl-acetyl)amino]phenyl]sulfonylamino]thiazole-4-carboxylic acid |
| X11 178 | | 5-[[4-[(2-hydroxy-3-phenyl-propanoyl)amino]phenyl]sulfonylamino]thiazole-4-carboxylic acid |
| X12 179 | | 5-[[2-(2-hydroxyethylamino)pyrimidin-5-yl]sulfonylamino]thiazole-4-carboxylic acid |
| X13 180 | | 5-[(2-methylpyrimidin-5-yl)sulfonylamino]thiazole-4-carboxylic acid |
| X14 181 | | 5-[[2-(4-pyridyl)pyrimidin-5-yl]sulfonylamino]thiazole-4-carboxylic acid |

TABLE 1-continued

Compounds of formula (IA), i.e. compounds of formula (I) in which R1 is H.

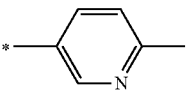

(IA)

| No | Z | Name |
|---|---|---|
| X15 182 | 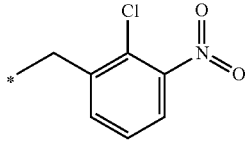 | 5-[(6-methyl-3-pyridyl)sulfonylamino]thiazole-4-carboxylic acid |
| 183 (ANT 753) | 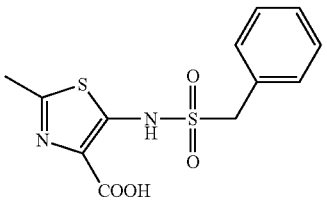 | 5-[(2-chloro-3-nitro-phenyl)methyl sulfonylamino]thiazole-4-carboxylic acid |

TABLE 2

Compounds of general formula (I) where $R^1$ is other than H

| No | Structure | Name |
|---|---|---|
| 50 | 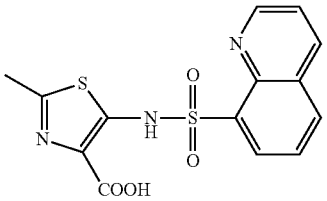 [SMILES: Cc1nc(C(=O)O)c(NS(=O)(=O)c2cccc3cccnc23)s1] | 5-benzylsulfonamido-2-methyl-1,3-thiazole-4-carboxylic acid; |
| 51 | 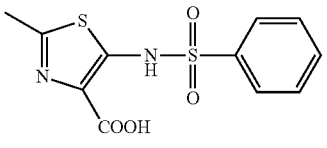 [SMILES: Cc1nc(C(=O)O)c(NS(=O)(=O)c2ccccc2)s1] | 2-methyl-5-(quinoline-8-sulfonamido)-1,3-thiazole-4-carboxylic acid; |
| 52 | 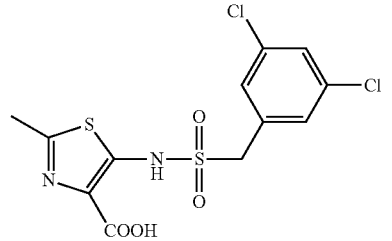 | 5-benzenesulfonamido-2-methyl-1,3-thiazole-4-carboxylic acid |
| 53 | 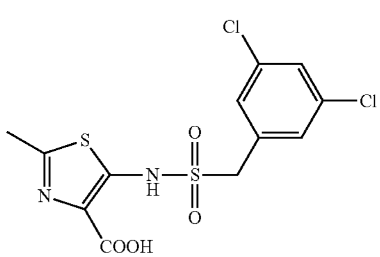 [SMILES: Cc1nc(C(=O)O)c(NS(=O)(=O)Cc2cc(Cl)cc(Cl)c2)s1] | 5-{[(3,5-dichlorophenyl)methyl]sulfonamido}-2-methyl-1,3-thiazole-4-carboxylic acid |

TABLE 2-continued

Compounds of general formula (I) where R¹ is other than H

| No | Structure | Name |
|---|---|---|
| 54 | 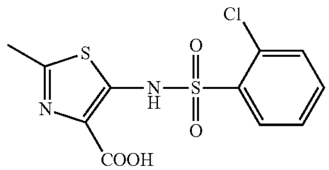 [SMILES: Cc1nc(C(=O)O)c(NS(=O)(=O)c2ccccc2Cl)s1] | 5-[(2-chlorophenyl)sulfonamido]-2-methyl-1,3-thiazole-4-carboxylic acid |
| 55 | 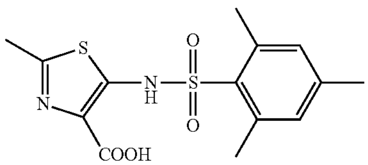 | 2-methyl-5-[(2,4,6-trimethylphenyl)sulfonamido]-1,3-thiazole-4-carboxylic acid |
| 56 | 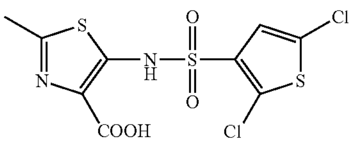 [SMILES: Cc1nc(C(=O)O)c(NS(=O)(=O)c2cc(Cl)sc2Cl)s1] | 5-[(2,5-dichlorothiophen-3-yl)sulfonamido]-2-methyl-1,3-thiazole-4-carboxylic acid |
| 57 | 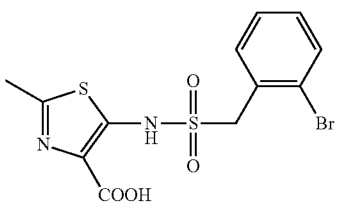 [SMILES: Cc1nc(C(=O)O)c(NS(=O)(=O)Cc2ccccc2Br)s1] | 5-{[(2-bromophenyl)methyl]sulfonamido}-2-methyl-1,3-thiazole-4-carboxylic acid |
| 58 | 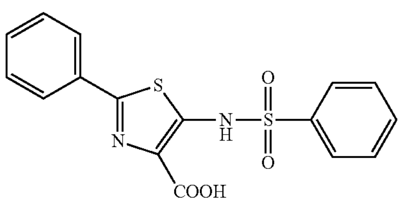 [SMILES: O=C(O)c1nc(-c2ccccc2)sc1NS(=O)(=O)c1ccccc1] | 5-benzenesulfonamido-2-phenyl-1,3-thiazole-4-carboxylic acid |
| 59 | 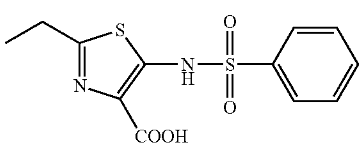 [SMILES: CCc1nc(C(=O)O)c(NS(=O)(=O)c2ccccc2)s1] | 5-benzenesulfonamido-2-ethyl-1,3-thiazole-4-carboxylic acid |
| 102 | 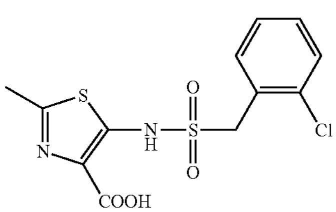 [SMILES: Cc1nc(C(=O)O)c(NS(=O)(=O)Cc2ccccc2Cl)s1] | 5-{[(2-chlorophenyl)methyl]sulfonamido}-2-methyl-1,3-thiazole-4-carboxylic acid |
| 96 | 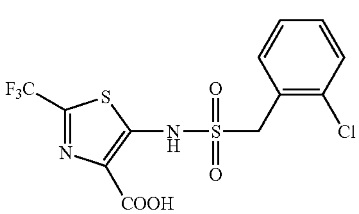 [SMILES: O=C(O)c1nc(C(F)(F)F)sc1NS(=O)(=O)Cc1ccccc1Cl] | 5-{[(2-chlorophenyl)methyl]sulfonamido}-2-(trifluoromethyl)-1,3-thiazole-4-carboxylic acid; |

Preparative HPLC Conditions:

Preparative HPLC was carried out using either a XSELECT CSH Prep C18 OBD [(30×150 mm), 5 μm)] column eluting with water/acetonitrile (+0.1% formic acid) at 60 mL/min or a XSELECT CSH Prep C6 Phenyl OBD [(19×250 mm), 5 μm] column eluting with water/acetonitrile (+0.1% formic acid) at 18 mL/min. Product detection was achieved using either a Agilent 6120 series Single Quadrupole Mass Spectrometer or a UV, diode array (190-450 nm).

Analytical LC-MS Conditions:

Method 1
Column: Acquity BEH C18, (2.1×100 mm), 1.7 μm; Flow 0.4 mL/min
Mobile Phase A: 0.1% formic acid (aq), B: 0.1% formic acid in acetonitrile
Gradient: T/% B 0.0/5, 0.4/5, 6.0/95, 6.8/95, 7.0/5

Method 2
Column: Phenomenex Luna C18(2), (4.6×30 mm), 3 μm; Flow 2.0 mL/min
Mobile Phase A: 0.1% formic acid (aq), B: 0.1% formic acid in acetonitrile
Gradient: T/% B 0.0/5, 0.5/5, 4.5/95, 5.5/95, 6.0/5

Method 3
Column: Phenomenex Luna C18(2), (4.6×30 mm), 3 μm; Flow 2.0 mL/min
Mobile Phase A: 0.1% formic acid (aq), B: 0.1% formic acid in acetonitrile
Gradient: T/% B 0.0/5, 0.3/5, 4.3/95, 5.3/95, 5.8/5, 6.0/5

Method 4
Column: X-Bridge C18, (4.6×100 mm), 3.5 μm; Flow
Mobile Phase A: 5 mM ammonium acetate (aq), B: acetonitrile
Gradient: T/% B0/5, 1/5, 2/15, 4.5/55, 6/95, 9.5/100, 10.5/5, 12/5

Method 5
Column: Acquity CSH-C18 (2.1×50 mm), 1.7 μm; Flow 0.4 mL/min
Mobile phase A: 0.1% formic acid (aq), B: 0.1% formic acid in acetonitrile
Gradient: T/% B0/2, 0.5/2, 1.2/45, 2.5/75, 3.2/100, 5.0/100, 5.01/2

Method 6
Column: XBridge BEH C18 (3.0×50 mm), 2.5 μm; Flow 0.7 mL/min
Mobile Phase A: 0.05% TFA (aq), B: 0.05% TFA in acetonitrile
Gradient: T/% B0/10, 0.6/10, 2/90, 5/90, 5.01/10

Method 7
Column: XBridge BEH C18 (2.1×50 mm), 1.7 μm; Flow 0.5 mL/min
Mobile Phase A: 0.05% TFA (aq), B: 0.05% TFA in acetonitrile
Gradient: T/% B0/10, 0.6/10, 2/90, 5/90, 5.01/10

Method 8
Column: XBridge C18 (4.6×100 mm), 54 μm; Flow 0.8 mL/min
Mobile phase A: 0.1% TFA (aq), B: acetonitrile
Gradient: T/% B0/10, 2/10, 4/80, 6/80, 7/98, 10.0/98, 10.1/10

Method 9
Column: Kinetex C18 (4.6×100 mm), 5 μm; Flow 0.8 mL/min
Mobile Phase A: 0.1% TFA (aq), B: acetonitrile
Gradient: T/% B0/2, 2/2, 5/80, 7/98, 12.0/98, 12.1/2

Method 10
Column: XBridge C18 (4.6×50 mm), 2.5 μm; Flow 1.3 mL/min
Mobile phase A: 0.1% formic acid (aq), B: 0.1% formic acid in acetonitrile
Gradient: T/% B: 0/5, 0.5/5, 1/15, 3.3/98, 5.2/98, 5.5/5, 6.0/5

Method 11
Column: XBridge C18 (4.6×50 mm), 2.5 μm; Flow 1.3 mL/min
Mobile phase A: 5 mM ammonium bicarbonate (aq), B: 100% acetonitrile
Gradient: T/% B: 0/5, 0.5/5, 1/15, 3.3/98, 5.2/98, 5.5/5, 6/5

Method 12
Column: Phenomenex Luna PFP(2) 100 A (4.6×150 mm), 5 μm; Flow 1 mL/min
Mobile phase A: 0.1% formic acid (aq), B: 0.075% formic acid in acetonitrile
Gradient: T/% B0/5, 0.5/5, 8/95, 10/95, 10.1/5, 11/5

Method 13
Column: Acquity BEH C18 (2.1×50 mm), 1.7 μm; Flow 0.6 mL/min
Mobile phase A: 0.1% formic acid (aq), B: 0.1% formic acid in acetonitrile
Gradient: T/% B: 0/3, 0.4/3, 3.2/98, 3.8/98, 4.2/3, 4.5/3

Method 14
Column: Acquity UPLC BEH C18 (2.1×50 mm), 1.7 μm; Flow 0.5 mL/min
Mobile Phase A: 5 mM ammonium acetate (aq), B: acetonitrile
Gradient: T/% B: 0/2, 1.5/2, 2/15, 3/55, 4/95, 6/95, 6.5/2, 7/2

Method 15
Column: Xbridge C18 (4.6×50 mm), 2.5 μm; Flow 1.0 mL/min
Mobile Phase A: 5 mM ammonium acetate (aq), B: acetonitrile
Gradient: T/% B: 0/5, 1.0/5, 3.5/85, 4.5/100, 7.5/100, 7.51/5

Method 16
Column: Xterra MS C18 (4.6×50 mm), 2.5 μm; Flow 1.0 mL/min
Mobile Phase A: 5 mM ammonium acetate (aq), B: acetonitrile
Gradient: T/% B: 0/5, 1.5/5, 4.6/85, 6.0/98, 8.0/98, 8.1/5.

Method 17
Column: Acquity BEH C18 (2.1×50 mm), 1.7 μm; Flow 0.3 mL/min
Mobile Phase A: 0.1% formic acid (aq), B: 0.1% formic acid in acetonitrile
Gradient: T %/B: 0/3, 2.5/98, 5/98, 5.1/3

Method 18:
Column: Acquity BEH C18 (2.1×50 mm), 1.8 μm; Flow 0.4 mL/min
Mobile Phase A: 0.025% TFA (aq), B: 0.025% TFA in acetonitrile
Gradient: T/% B: 0/2, 0.8/2, 2.0/45, 3.0/75, 3.5/100, 5.0/100, 5.1/2

Method 19
Column: Acquity BEH C18 (2.1×50 mm), 1.7 μm; Flow 0.6 mL/min
Mobile Phase A: 0.05% TFA (aq); B: acetonitrile
Gradient: T/% B: 0/3, 0.2/3, 1/35, 2/98, 3.8/98, 3.9/3, 4/3

Method 20
Column: Kinetexy C18 (2.1×50 mm), 1.7 μm; Flow 0.4 mL/min
Mobile Phase A: 0.1% formic acid (aq), B: 0.1% formic acid in acetonitrile
Gradient: T/% B: 0/2, 0.5/2, 1.5/45, 2.5/75, 3.2/100, 4.0/100, 5.0/100, 5.1/2

Method 21
Column: Phenomenex kinetex C18 (4.6×100 mm), 5 μm; Flow 0.8 mL/min
Mobile Phase A: 10 mM ammonium bicarbonate (aq), B: acetonitrile
Gradient: T/% B0/10, 0.5/10, 1.8/55, 3.5/100, 6.8/100, 8.0/10

Method 22
Column: X-Bridge C18 (4.6×50 mm), 3.5 μm; Flow
Mobile Phase A: 10 mM ammonium carbonate (aq), B: acetonitrile
Gradient: T/% B: 0/10, 0.5/10, 1.8/85, 4.2/100, 6.5/100, 6.51/10.

Method 23
Column: Xbridge C18 (3.0×50 mm), 3.5 μm; Flow 1.0 mL/min
Mobile Phase A: 5 mM ammonium acetate (aq), B: acetonitrile
Gradient: T/% B: 0/10, 3/50, 5/90, 9/90, 9.1/10

Method 24
Column: X-bridge C18 (4.6×75 mm), 3.5 μm; Flow 0.8 ml/min
Mobile Phase A: 5 mM ammonium acetate (aq), B: acetonitrile
Gradient: T/% B: 0/5, 2.5/98, 8.0/98, 8.1/5

Method 25
Column: Acquity HSS T3 C18 (2.1×50 mm), 1.8 μm; Flow 0.4 mL/min
Mobile Phase A: 0.05% formic acid (aq) containing 3.75 mM ammonium acetate, B: 0.04% formic acid in acetonitrile
Gradient: T %/B: 0/2, 0.5/2, 1.2/45, 2.2/75, 3.5/100, 5/100, 5.01/2.

Method 26
Column: BEH Phenyl (2.1×50 mm), 1.7 μm; Flow 0.3 mL/min
Mobile Phase A: 0.1% formic acid (aq), B: acetonitrile
Gradient: T/% B: 0/3, 3/98, 7/98, 5.1/3

Method 27
Column: X-Bridge C18 (4.6×75 mm), 3.5 μm; Flow 0.8 mL/min
Mobile Phase A: 0.05% formic acid (aq) containing 3.75 mM ammonium acetate, B: 0.04% formic acid in acetonitrile
Gradient: T/% B: 0/5, 1.5/5, 3.5/98, 8.0/98, 8.1/5

Method 28
Column: Acquity BEH C18 (2.1×50 mm), 1.7 μm; Flow 0.4 mL/min
Mobile Phase A: 0.1% formic acid (aq), B: 0.1% formic acid in acetonitrile
Gradient: T/% B: 0/2, 0.8/2, 2.0/45, 3.0/75, 3.5/100 5.0/100, 5.01/98.

Method 29
Column: X-Select CSH C18 (4.6×50 mm), 5 μm; Flow 0.4 mL/min
Mobile Phase A: 0.1% formic acid (aq), B: 0.1% formic acid in acetonitrile
Gradient: T/% B: 0/5, 1/5, 2/75, 4.5/100, 6/100, 6.51/5.

Method 30
Column: X-Select C-18 (4.6×50 mm), 3.5 μm; Flow 0.8 mL/min
Mobile phase A: 0.1% formic acid (aq), B: acetonitrile
Gradient: T/% B: 0/5, 1/5, 5/85, 5.5/100, 8.5/100, 9.0/5.

Method 31
Column: Acquity UPLC BEH (2.1×100 mm), 1.7 μm; Flow 0.4 mL/min
Mobile Phase A: 0.1% formic acid (aq), B: 0.1% formic acid in acetonitrile
Gradient: T/% B: 0/5, 0.8/5, 2/45, 3/75, 3.5/95, 4/100, 5.5/100, 6.01/5

Method: 32
Column: BEH C18 (2.1×50 mm), 1.7 μm; Flow 0.5 mL/min
Mobile Phase A: 0.1% formic acid (aq), B: 0.1% formic acid in acetonitrile
Gradient: T/% B: 0.0/3, 0.2/3, 1/35, 2/98, 3.85/98, 3.9/3, 4/3

Method 33
Column: X-Bridge C18 (4.6×50 mm), 2.5 μm; Flow
Mobile Phase A: 10 mM ammonium bicarbonate (aq), B: acetonitrile
Gradient: T/% B: 0/10, 0.5/10, 1.8/85, 4.2/100, 8/100, 8.1/10

Method 34
Column: X-Bridge C18 (4.6×50 mm), 3.5 μm; Flow
Mobile Phase A: 3.75 mM ammonium acetate (aq), B: 0.04% formic acid in acetonitrile
Gradient: T/% B: 0/10, 0.5/10, 1.8/85, 4.2/100, 8.0/100, 8.01/10

Method 35
Column: X-Bridge C18 (4.6×50 mm), 3.5 μm; Flow
Mobile Phase A: 0.05% formic acid (aq) containing 3.75 mM ammonium acetate, B: 0.04% formic acid in acetonitrile
Gradient: T/% B: 0/5, 1.5/5, 5.0/85, 5.5/100, 7.0/100, 7.01/5

Method 36
Column: XBridge C18 (4.6×100 mm), 3.5 μm; Flow 1.0 mL/min
Mobile Phase A: 5 mM ammonium acetate (aq), B: acetonitrile
Gradient: T/% B: 0/5, 1/5, 2/15, 4.5/55, 6/100, 9.5/100, 10.5/5, 12/5

Method 37
Column: Acquity BEH C18 (2.1×100 mm), 1.7 μm; Flow 0.5 mL/min
Mobile Phase A: 0.05% formic acid (aq) containing 3.75 mM ammonium acetate, B: 0.04% formic acid in acetonitrile
Gradient: T/% B: 0/3, 0.2/3, 1/35, 2/98, 3.85/98, 3.90/3, 4/3

Method 38
Column: Acquity UPLC BEH C18 (2.1×50 mm), 1.7 μm; Flow 0.6 mL/min
Mobile phase A: 0.1% formic acid (aq), B: 0.1% formic acid in acetonitrile
Gradient: T %/B: 0/5, 0.5/5, 1.7/35, 4.0/95, 5.2/95, 5.21/5

$^1$H NMR Spectra $^1$H NMR spectra were obtained at 300 or 400 MHz in deuterated CDCl$_3$ or DMSO-d$_6$ solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets), obs (obscured). Coupling constants, when given, are reported in hertz (Hz).

Abbreviations

The following abbreviations were used:
DMF: dimethyl formamide
DMSO: dimethyl sulfoxide
IMS: industrial methylated spirits
NMP: N-methylpyrrolidinone
DMA: dimethyl acetamide
Pd$_2$dba$_3$: tris(dibenzylidene-acetone)dipalladium(0)
TTBP: tri-tert-butylphosphonium tetra-fluoroborate
Pd(dppf)Cl$_2$.DCM: [1,1'-Bis(diphenylphosphino)ferrocene]dichloro palladium(II); complex with dichloromethane
Pd(PPh$_3$)$_4$: tetrakis(triphenylphosphine)palladium(0)
Pd(OAc)$_2$: palladium (II) acetate
PdCl$_2$(dcpf): [1,1'-Bis(di-cyclohexylphosphino)ferrocene]dichloro-palladium(II)

DMAP: 4-dimethylaminopyridine
NBS: N-bromosuccinimde
HATU: 1-[bis(dimethylamino)methylene]-1H-1,2,3-triazolo[4,5-b]-pyridinum-3-oxide hexafluorophosphate
TEA: triethylamine
DIPA: diisopropylamine
NMM: N-methylmorpholine
TFA: trifluoroacetic acid
TFAA: trifluoroacetic anhydride
Xantphos: 4,5-Bis(diphenylphosphino)-9,9-dimethylxanthene
Rt: retention time
min: minutes.

All sulfonyl chlorides whose synthesis is not described herein were commercially available or were prepared by literature methods.

Example 1: Compound 93

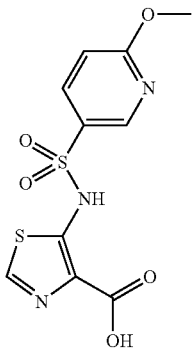 [SMILES: COc1ccc(S(=O)(=O)Nc2scnc2C(=O)O)cn1]

Intermediate 1 (107 mg, 0.218 mmol) was treated with 95% TFA(aq) (5 mL) at room temperature and the mixture stirred for 60 minutes. The solvent was removed in vacuo and the residue purified by reverse phase HPLC. The fractions containing the desired product were combined and lyophilised to give Compound 93 (24.7 mg) as an off-white solid.

1H NMR (DMSO-$d_6$) δ: 8.58 (1H, d), 8.55 (1H, br s), 8.05 (1H, dd), 6.98 (1H, d), 3.91 (3H, s)
LCMS (Method 1) Rt 2.89 min; m/z (M−H)⁻ 314

Intermediate 1

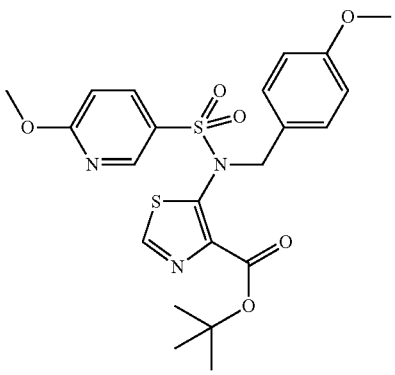

Intermediate 2 (100 mg, 0.312 mmol) and 15-crown-5 (0.1 mL) were dissolved in dry tetrahydrofuran (5 mL). To this, sodium hydride (60% disp. in oil; 32 mg, 0.78 mmol) was added at room temperature and the mixture was stirred for 30 minutes. To this, 6-methoxypyridine-3-sulfonyl chloride (97 mg, 0.468 mmol) was added and the mixture stirred at room temperature for 18 hours. The reaction mixture was diluted with water and extracted with ethyl acetate. The organic solution was washed with brine, dried with $Na_2SO_4$, filtered and concentrated in vacuo to dryness. The residue was purified by chromatography on silica eluting with 0-50% ethyl acetate/cyclohexane. The fractions containing the desired product were combined and the solvents removed by evaporation in vacuo to give Intermediate 1 (107 mg) as a yellow glass.

LCMS (Method 2) Rt 3.95 min; m/z (M+H)⁺ 492

Intermediate 2

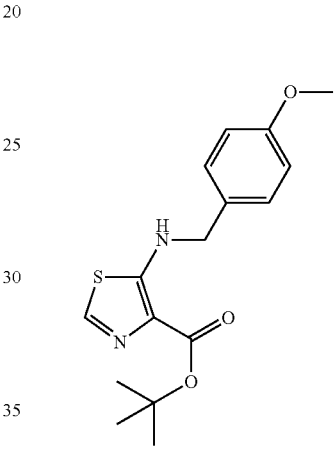

A suspension of potassium tert-butoxide (874 mg, 7.79 mmol) in dry tetrahydrofuran (10 mL) was stirred vigorously at room temperature. To this, a solution of tert-butyl isocyanoacetate (1.0 g, 7.08 mmol) in dry tetrahydrofuran (5 mL) was added drop wise and the mixture stirred at room temperature for 10 minutes. To this, a solution of 4-methoxybenzyl isothiocyanate (1.27 g, 7.08 mmol) in dry tetrahydrofuran (5 mL) was added drop wise at room temperature. After 2 hours the solution was poured into saturated $NaHCO_3$ solution and extracted with ethyl acetate. The organic layer was dried with $Na_2SO_4$, filtered and concentrated in vacuo to dryness. The residue was purified by chromatography on silica eluting with 0-50% ethyl acetate/cyclohexane. The fractions containing the desired product were combined and the solvent removed by evaporation in vacuo to give Intermediate 2 (852 mg) as a pale yellow solid.

1H NMR ($CDCl_3$) δ: 7.81 (1H, m), 7.73 (1H, br s), 7.31-7.23 (2H, m), 6.92-6.85 (2H, m), 4.35 (2H, d), 3.80 (3H, s), 1.61 (9H, s)
LCMS (Method 2) Rt 3.70 min; m/z (M+H)⁺ 321

The following compounds were prepared using a similar method as described in Example 1. In the synthesis of Compound 171, the dihydroisoindole nitrogen was protected by Boc.

| No | Structure | LCMS Method | Rt (min) | Mass [M − H]− |
|---|---|---|---|---|
| 101 | 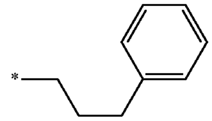 [SMILES: *CCCc1ccccc1] | Method 1 | 3.67 | 325 |
| 95 | 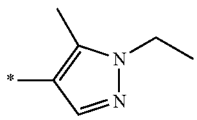 [SMILES: *c1cnn(CC)c1C] | Method 1 | 2.67 | 315 |
| 146 | 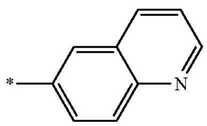 [SMILES: *c1ccc2ncccc2c1] | Method 1 | 2.48 | 334 |
| 94 | 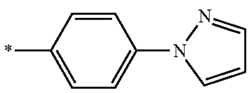 | Method 1 | 3.15 | 349 |
| 148 | 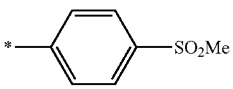 [SMILES: *c1ccc(S(C)(=O)=O)cc1] | Method 1 | 2.58 | 361 |
| 82 | 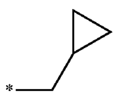 | Method 1 | 2.58 | 261 |
| 171 | 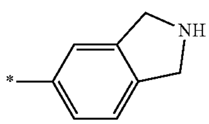 [SMILES: *c1ccc2c(c1)CNC2] | Method 1 | 1.73 | 324 |
| 182 | 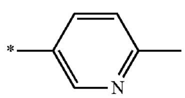 [SMILES: *c1ccc(C)nc1] | Method 1 | 2.66 | 298 |

Example 2: Compound 61

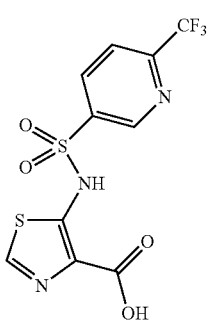 [SMILES: O=C(O)c1ncsc1NS(=O)(=O)c1ccc(C(F)(F)F)nc1]

Intermediate 3 (55 mg, 0.144 mmol) was suspended in methanol (1 mL) and tetrahydrofuran (1 mL). To this, a solution of lithium hydroxide monohydrate (30 mg, 0.714 mmol) in water (2 mL) was added and the mixture heated at 50° C. for 18 hours. The mixture was cooled to room temperature and the solvents were removed in vacuo. The residue was diluted with water and acidified with 1M hydrochloric acid. The product was collected by filtration, washed with water and dried under vacuum to give Compound 61 (39 mg) as an off white solid.

1H NMR (DMSO-$d_6$) δ: 9.07 (1H, d), 8.48 (1H, s), 8.39 (1H, dd), 8.07 (1H, d) LCMS (Method 1) Rt 3.30 min; m/z (M−H)− 352

Intermediate 3

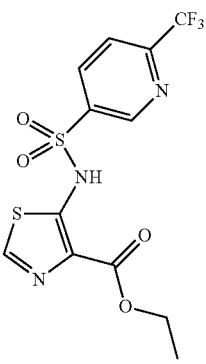 [SMILES: CCOC(=O)c1ncsc1NS(=O)(=O)c1ccc(C(F)(F)F)nc1]

5-Amino-thiazole-4-carboxylic acid ethyl ester (172 mg, 1.0 mmol) was suspended in pyridine (3 mL). To this, 6-(trifluoromethyl)pyridine-3-sulfonyl chloride (330 mg, 1.35 mmol) was added and the mixture heated at 50° C. for 3 hours. The mixture was diluted with water and extracted with ethyl acetate. The combined organic layers were dried with $Na_2SO_4$, filtered and concentrated in vacuo to dryness. The residue was purified by chromatography on silica eluting with 0-100% ethyl acetate/cyclohexane. The fractions containing the desired product were combined and the solvent removed by evaporation in vacuo. The solid was triturated with diethyl ether to give Intermediate 3 (59 mg) as an off white solid.

1H NMR (DMSO-$d_6$) δ: 9.20 (1H, m), 8.42-8.31 (2H, m), 7.84 (1H, m), 4.41 (2H, q), 1.40 (3H, t)

Example 3: Compound 13

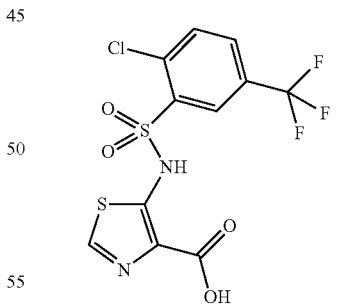

Intermediate 4 (340 mg, 0.821 mmol) was dissolved in tetrahydrofuran (1 mL) and water (0.5 mL). To this, lithium hydroxide monohydrate (86 mg, 2.053 mmol) was added at room temperature and stirred for 18 hours. To this, lithium hydroxide monohydrate (52 mg, 1.24 mmol) was added at room temperature and stirred for 16 hours. To this, lithium hydroxide monohydrate (52 mg, 1.24 mmol) was added at room temperature and stirred for 16 hours. The mixture was concentrated in vacuo, diluted with water and washed with diethyl ether. The aqueous layer was acidified with 1N hydrochloric acid solution. The product was collected by filtration, washed with diethyl ether and dried under vacuum to give Compound 13 (106 mg) as a brown solid.

1H NMR (DMSO-d$_6$) δ: 8.65-8.45 (3H, m), 8.15 (1H, t), 3.55-3.45 (2H, m), 3.40-3.30 (2H, m)

LCMS (Method 24) Rt 3.35 min; m/z (M−H)⁻ 385

Intermediate 4

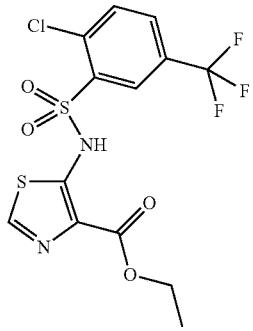 [SMILES: CCOC(=O)c1ncsc1NS(=O)(=O)c1cc(C(F)(F)F)ccc1Cl]

5-Amino-thiazole-4-carboxylic acid ethyl ester (250 mg, 1.453 mmol) and triethylamine (1.02 mL, 7.265 mmol) were dissolved in 1,4-dioxan (6 mL). To this, 2-chloro-5-(trifluoromethyl)benzene-1-sulfonyl chloride (0.3 mL, 1.744 mmol) was added at room temperature and stirred for 16 hours. The mixture was concentrated in vacuo and extracted with ethyl acetate. The organic layer was washed with 1N hydrochloric acid solution and water. The organic layer was dried with Na$_2$SO$_4$, filtered and concentrated in vacuo. The residue was triturated with n-pentane, the product collected by filtration and dried under vacuum to give Intermediate 4 (340 mg).

LCMS (Method 26) Rt 2.63 min; m/z (M+H)⁺ 415

The following compounds were prepared using a similar method as described in Example 2.

| No | Structure | LCMS Method | Rt (min) | Mass [M − 1]− |
|---|---|---|---|---|
| 66 | Cl-phenyl | Method 1 | 3.13 | 317 |
| 68 | 2,6-diCl-phenyl | Method 1 | 3.28 | 351 |
| 79 | 2-MeO-phenyl | Method 1 | 3.15 | 313 |
| 62 | phenoxyethyl | Method 1 | 3.26 | 327 |
| 63 | phthalimidoethyl | Method 1 | 2.81 | 380 |
| 67 | 3-pyridyl | Method 1 | 2.14 | 284 |
| 61 | 2-CF$_3$-pyridyl | Method 1 | 3.30 | 352 |
| 81 | 5-methyl-1-phenyl-pyrazolyl | Method 1 | 3.35 | 363 |
| 65 | 5-CF$_3$-2-pyridyl-pyrazole | Method 1 | 3.99 | 418 |
| 89 | 4-morpholinophenyl | Method 1 | 3.12 | 368 |
| 122 | 2,4-diCl-benzyl | Method 4 | 5.33 | 365 |
| 123 | 2-F-benzyl | Method 13 | 1.63 | 317 |
| 124 | 2,3-diF-benzyl | Method 13 | 1.67 | 335 |
| 126 | 2,5-diCl-benzyl | Method 13 | 2.02 | 365/367 |

-continued
| No | Structure | LCMS Method | Rt (min) | Mass [M − 1]− |
|---|---|---|---|---|
| 127 | 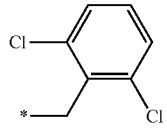 | Method 13 | 1.96 | 365/367 |
| 128 | 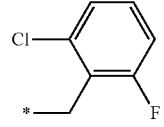 [SMILES: *Cc1c(F)cccc1Cl] | Method 13 | 1.86 | 349 |
| 129 | 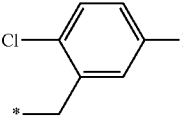 | Method 13 | 1.92 | 349 |
| 78 | 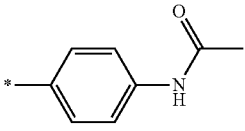 [SMILES: *c1ccc(NC(C)=O)cc1] | Method 1 | 2.59 | 340 |
| 87 | 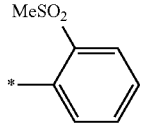 | Method 9 | 5.88 | 363 |
| 33 | 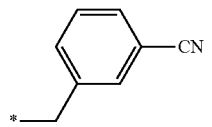 [SMILES: *Cc1cccc(C#N)c1] | Method 34 | ? | 322 |
| 34 | 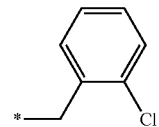 [SMILES: *Cc1ccccc1Cl] | Method 20 | 3.04 | 333 |
| 35 | 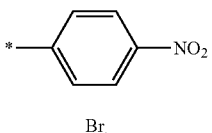 | Method 34 | 2.43 | 328 |
| 45 | 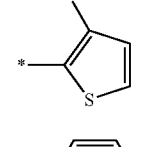 | Method 22 | 2.35 | 369 |
| 46 | 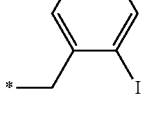 | Method 22 | 2.42 | 423 |
| 41 | 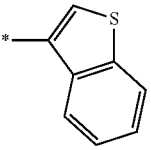 | Method 20 | 1.94 | 339 |
-continued
| No | Structure | LCMS Method | Rt (min) | Mass [M − 1]− |
|---|---|---|---|---|
| 18 | 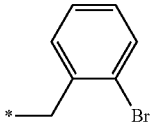 [SMILES: *Cc1ccccc1Br] | Method 36 | 4.84 | 375 |
| 22 | 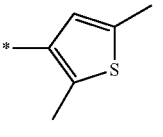 | Method 18 | 2.71 | 319 |
| 91 | 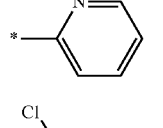 | Method 4 | 4.40 | 284 |
| 132 | 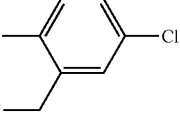 | Method 14 | 3.22 | 399/401 |
| 135 | 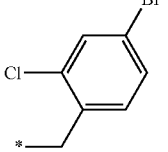 | Method 37 | 5.46 | 409/411 |
| 130 | 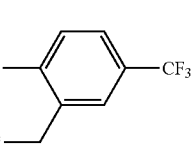 | Method 13 | 2.06 | 399 |
| 145 | 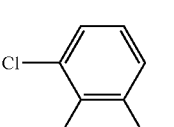 | Method 14 | 3.02 | 378 |
| 48 | 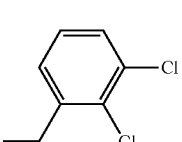 | Method 22 | 2.45 | 365 |
| 1 | 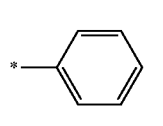 | Method 23 | 3.40 | 285 |
| 2 | 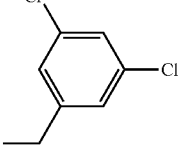 | Method 24 | 3.29 | 367 |
| 4 | 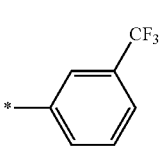 [SMILES: *c1cccc(C(F)(F)F)c1] | Method 23 | 4.28 | 351 |

-continued

| No | Structure | LCMS Method | Rt (min) | Mass [M − 1]− |
|---|---|---|---|---|
| 5 | benzyl | Method 24 | 3.19 | 297 |
| 8 | 3-thienyl | Method 27 | 2.70 | 289 |
| 16 | 2-methylbenzyl | Method 17 | 1.37 | 311 |
| 92 | 1-methylimidazol-2-yl | Method 5 | 1.72 | 287 |
| 110 | 1,2-dimethylimidazol-4-yl | Method 10 | 1.53 | 303 |
| 133 | 2,3-dichloro-6-fluorobenzyl | Method 36 | 5.30 | 383/385 |
| 134 | 2,3-dichloro-6-(trifluoromethyl)benzyl | Method 36 | 5.63 | 433/435 |
| 90 | 4-carboxyphenyl | | | |
| 7 | phenethyl | | | |
| 10 | 2,5-dichlorothien-3-yl | | | |
| 14 | 3,5-bis(trifluoromethyl)phenyl | | | |

Example 4: Compound 60

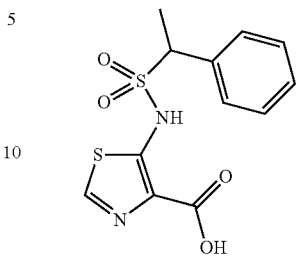

Intermediate 5 (137 mg, 0.42 mmol) was dissolved in methanol (2 mL) and tetrahydrofuran (8 mL). To this, lithium hydroxide monohydrate (176 mg, 4.2 mmol) was added and the mixture stirred at room temperature for 19 hours. The solvents were removed in vacuo and the residue partitioned between water and ethyl acetate. The aqueous layer was acidified to pH 3 with 10% citric acid solution and extracted with ethyl acetate. The organic layer was washed with brine, dried with $Na_2SO_4$, filtered and concentrated in vacuo to dryness. The residue was purified by reverse phase HPLC. The fractions containing the desired product were combined and lyophilised to give Compound 60 (44.1 mg) as an off white solid.

1H NMR (DMSO-$d_6$) δ: 8.43 (1H, s), 7.40-7.33 (2H, m), 7.32-7.25 (3H, m), 4.83 (1H, q), 1.69 (3H, d) LCMS (Method 1) Rt 3.30 min; m/z (M−H)− 311

Intermediate 5

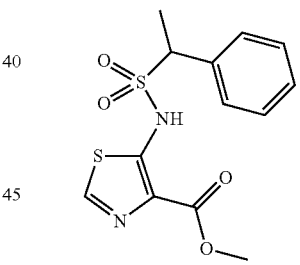

A mixture of methyl 5-bromo-1,3-thiazole-4-carboxylate (112 mg, 0.504 mmol), Intermediate 6 (112 mg, 0.605 mmol), $Pd_2dba_3$ (46 mg, 0.05 mmol), xantphos (88 mg, 0.151 mmol), $Cs_2CO_3$ (230 mg, 0.706 mmol) and dry dioxan (5 mL) was heated at 90° C. under nitrogen for 20 hours. After cooling to room temperature, the mixture was partitioned between ethyl acetate and 10% citric acid solution. The organic layer was washed with brine, dried with $Na_2SO_4$, filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 5 (137 mg) as a brown gum.

LCMS (Method 2) Rt 3.08 min; m/z (M+H)+ 327

Intermediate 6

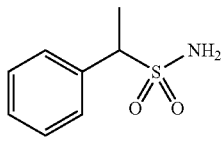

Intermediate 7 (309 mg, 1.2 mmol) was dissolved in DMSO (2 mL). To this, sodium methoxide (30% solution in methanol; 0.275 mL, 1.2 mmol) was added drop wise at room temperature and stirred for 15 minutes. To this, a solution of hydroxylamine-O-sulfonic acid (679 mg, 6.0 mmol) and sodium acetate (375 mg, 4.56 mmol) in water (5 mL) was added drop wise at 0° C. The mixture was allowed to warm to room temperature overnight. The mixture was partitioned between ethyl acetate and water, separated and the aqueous layer extracted with ethyl acetate. The combined organic layers were washed with water, brine, dried with $Na_2SO_4$, filtered through a pad of silica and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 6 (112 mg).

1H NMR (DMSO-$d_6$) δ: 7.47-7.23 (5H, m), 6.76 (2H, s), 4.22 (1H, q), 1.63 (3H, d)

Intermediate 7

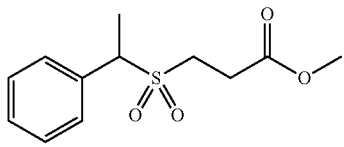 [SMILES: COC(=O)CCS(=O)(=O)C(C)c1ccccc1]

Sodium 1-methyl-3-sulfinopropanoate (282 mg, 1.62 mmol) was suspended in DMSO (2.5 mL). To this, (1-bromoethyl)benzene (0.185 mL, 1.35 mmol) was added and the mixture stirred at room temperature for 18 hours. The mixture was poured into water (25 mL) and extracted with diethyl ether. The organic layer was washed with brine, dried with $Na_2SO_4$, filtered and concentrated in vacuo to give Intermediate 7 (309 mg) as an oil.

1H NMR (CDCl$_3$) δ: 7.50-7.33 (5H, m), 4.23 (1H, q), 3.68 (3H, s), 3.18-2.94 (2H, m), 2.83-2.56 (2H, m), 1.80 (3H, d)

The following compounds were prepared using a similar method as described in Example 4.

Compounds 168 and 169 were prepared by first preparing the racemic material and then separating by chiral HPL. Compound 168 was the first eluting isomer and Compound 169 was the second eluting isomer.

| No | Structure | LCMS Method | Rt (min) | Mass [M − H]− |
|---|---|---|---|---|
| 80 | 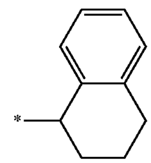 [SMILES: *C1CCCc2ccccc21] | Method 1 | 3.65 | 337 |
| 104 | 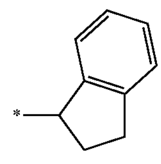 [SMILES: *C1CCc2ccccc21] | Method 1 | 3.41 | 323 |
| 60 | 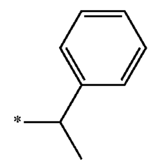 [SMILES: *C(C)c1ccccc1] | Method 1 | 3.30 | 311 |
| 64 | 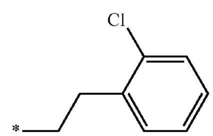 [SMILES: *CCc1ccccc1Cl] | Method 1 | 3.66 | 345 |
| 168 | 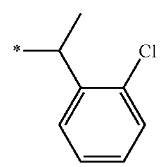 [SMILES: *C(C)c1ccccc1Cl] | Method 4 | 5.32 | 345 |
| 169 | 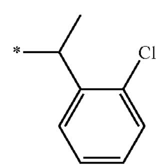 [SMILES: *C(C)c1ccccc1Cl] | Method 4 | 5.26 | 345 |
| 83 | 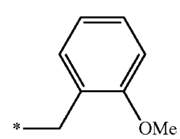 [SMILES: *Cc1ccccc1OC] | Method 17 | 2.01 | 327 |
| 86 | 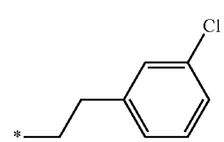 [SMILES: *CCc1cccc(Cl)c1] | Method 28 | 1.90 | 347 |
| 84 | 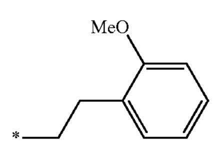 [SMILES: *CCc1ccccc1OC] | Method 28 | 2.25 | 345 |
| 85 | 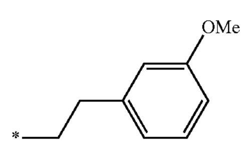 [SMILES: *CCc1cccc(OC)c1] | Method 28 | 2.10 | 341 |

-continued

| No | Structure | LCMS Method | Rt (min) | Mass [M − H]− |
|----|-----------|-------------|----------|----------------|
| 74 | *—CH₂CH₂—C₆H₄—Cl | Method 7 | 1.87 | 347 |
| 71 | *—CH(CH₂CH₃)—C₆H₅ | Method 6 | 1.82 | 327 |
| 144 | Cl-methylenedioxyphenyl-CH₂—* | Method 36 | 5.30 | 377 |

Example 5: Compound 70

Intermediate 8 (103 mg, 0.269 mmol) was suspended in dioxan (8 mL), IMS (2 mL) and water (2 mL). To this, lithium hydroxide monohydrate (113 mg, 2.69 mmol) was added at room temperature and stirred for 24 hours. To this, lithium hydroxide monohydrate (113 mg, 2.69 mmol) was added and the mixture stirred at 70° C. for 3 hours. The mixture was cooled to room temperature and the solvents removed in vacuo. The residue was diluted with water and made acid to pH 3 with 10% citric acid solution. The solid formed was collected by filtration, washed with water and dried under vacuum to give Compound 70 (71 mg).

1H NMR (DMSO-d₆) δ: 8.55 (1H, s), 7.09-7.02 (2H, m), 6.83-6.77 (1H, m), 4.27 (2H, t), 3.28 (2H, t), 2.83 (3H, s)
LCMS (Method 1) Rt: 3.35 min; m/z (M−H)⁻ 354

Intermediate 8

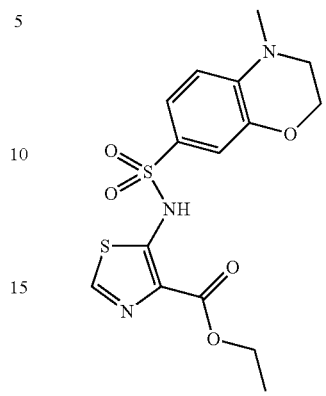

Intermediate 9 (192 mg, 0.405 mmol) was dissolved in dichloromethane (5 mL). To this, concentrated sulfuric acid (0.5 mL) was added at 0° C. and the mixture warmed to room temperature over 30 minutes. The mixture was diluted with dichloromethane and water (1:1) and neutralized with solid Na₂CO₃. The organic layer was washed with brine, dried with Na₂SO₄, filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 8 (103 mg).

LCMS (Method 2) Rt 3.35 min; m/z (M+H)⁺ 384

Intermediate 9

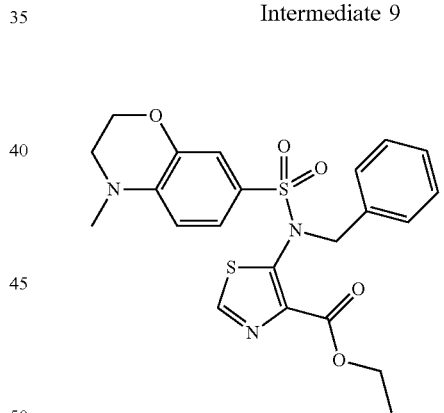

Intermediate 10 (200 mg, 0.762 mmol) and 15-crown-5 (0.02 mL) were dissolved in dry tetrahydrofuran (5 mL). To this, sodium hydride (60% disp. in mineral oil; 43 mg, 1.07 mmol) was added at 0° C. and the mixture was stirred for 5 minutes. To this, 4-methyl-3,4-dihydro-2H-1,4-benzoxazine-7-sulfonyl chloride (226 mg, 0.914 mmol) was added and the mixture stirred at room temperature for 18 hours. The mixture was diluted with saturated NaHCO₃ solution and extracted with ethyl acetate. The organic layer was washed with brine, dried with Na₂SO₄, filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 9 (137 mg).

LCMS (Method 2) Rt 3.76 min; m/z (M+H)⁺ 474

Intermediate 10

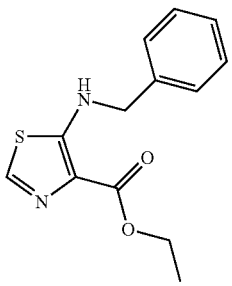 [SMILES: CCOC(=O)c1ncsc1NCc1ccccc1]

A suspension of potassium tert-butoxide (20.7 g, 184 mmol) in dry tetrahydrofuran (500 mL) was stirred vigorously at room temperature. To this, ethyl isocyanoacetate (19.0 g, 168 mmol) was added drop wise at room temperature and the mixture stirred for 10 minutes. To this, benzyl isothiocyanate [(25 g, 168 mmol) was added drop wise at room temperature and the mixture stirred for 2 hours. The mixture was neutralized with glacial acetic acid and concentrated in vacuo. The residue was suspended in ethyl acetate. The organic layer was washed with water, saturated NaHCO$_3$ and brine. The organic layer was dried with Na$_2$SO$_4$, filtered and concentrated in vacuo to dryness. The residue was purified by chromatography on silica eluting with 0-66% ethyl acetate/cyclohexane. The fractions containing the desired product were combined and the solvents removed by evaporation in vacuo to give Intermediate 10 (34.15 g) as a brown oil.

1H NMR (CDCl3) δ: 7.89-7.74 (2H, m), 7.41-7.27 (5H, m), 4.45 (2H, d), 4.38 (2H, q), 1.41 (3H, t)

The following compounds were prepared using a similar method as described in Example 5.

| No | Structure | LCMS Method | Rt (min) | Mass [M − H]− |
|---|---|---|---|---|
| 69 | 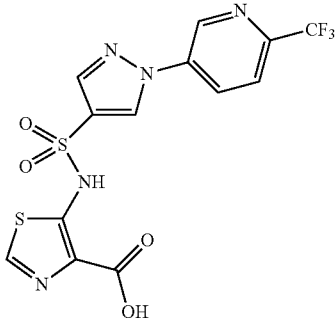 [SMILES: O=C(O)c1ncsc1NS(=O)(=O)c1cnn(-c2ccc(C(F)(F)F)nc2)c1] | Method 1 | 3.79 | 303 |

Example 6: Compound 114

Intermediate 11 (158 mg, 0.332 mmol) was treated with 95% TFA(aq) (5 mL) at room temperature and the mixture stirred for 3 hours. The solvent was removed in vacuo and the residue azeotroped with toluene to dryness. The residue was purified by reverse phase HPLC. The fractions containing the desired product were combined and lyophilised to give Compound 114 (44.8 mg) as an off-white solid.

1H NMR (DMSO-d$_6$) δ: 9.38 (1H, s), 9.33 (1H, d), 8.63-8.53 (2H, d), 8.22 (1H, s), 8.09 (1H, d)

LCMS (Method 1) Rt 3.64 min; m/z (M−H)− 418

Intermediate 11

A mixture of Intermediate 12 (113 mg, 0.428 mmol), Intermediate 13 (150 mg, 0.514 mmol), Pd$_2$dba$_3$ (39 mg, 0.043 mmol), xantphos (74 mg, 0.128 mmol), Cs$_2$CO$_3$ (195 mg, 0.6 mmol) and dry dioxan (5 mL) was heated at 90° C. under nitrogen for 20 hours. The mixture was cooled to room temperature and partitioned between ethyl acetate and 10% citric acid solution. The organic layer was washed with brine, dried with Na$_2$SO$_4$, filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 11 (158 mg).

LCMS (Method 2) Rt 3.86 min; m/z (M+H)+ 476

Intermediate 12

5-Bromothiazole-4-carboxylic acid (2.17 g, 10.4 mmol) was dissolved in dry dioxan (170 mL) and heated at 100° C. To this, N,N-dimethyl-formamide di-tert-butyl acetal (13.68 g, 67.28 mmol) was added drop wise and the mixture stirred at 100° C. for 1 hour. The mixture was cooled to room temperature and stirred for 18 hours. The volatile solvents were removed in vacuo and the residue partitioned between water and diethyl ether. The organic layer was washed with saturated NaHCO₃, dried with Na₂SO₄, filtered and concentrated in vacuo to dryness. The residue was purified by chromatography on silica eluting with 0-20% ethyl acetate/cyclohexane. The fractions containing the desired product were combined and the solvents removed by evaporation in vacuo to give Intermediate 12 (2.8 g) as a yellow solid.

1H NMR (CDCl₃) δ: 8.76 (1H, s), 1.63 (9H, s)

LCMS (Method 2) Rt 3.23 min; m/z (M+H)⁺ 265

Intermediate 13

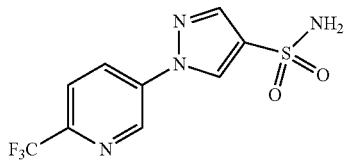 [SMILES: NS(=O)(=O)c1cnn(-c2ccc(C(F)(F)F)nc2)c1]

Ammonium hydroxide solution (33% in water; 10 mL) was cooled to 0° C. To this, a solution of Intermediate 14 (785 mg, 2.52 mmol) in acetone (5 mL) was added drop wise and the mixture stirred for 15 minutes. The mixture was allowed to warm to room temperature and stirred for 1 hour. The volatile solvents were removed in vacuo and the resulting solid partitioned between ethyl acetate and water. The organic layer was dried with Na₂SO₄, filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 13 (476 mg) as a white solid.

LCMS (Method 2) Rt 2.67 min; m/z (M+H)⁺ 293

Intermediate 14

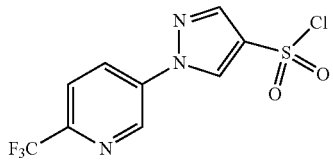

A mixture of Intermediate 15 (1.19 g, 5.58 mmol) and chlorosulfonic acid (10 mL) was heated at 90° C. for 18 hours. The mixture was cooled to room temperature and poured onto ice/water. The mixture was extracted with dichloromethane, dried with Na₂SO₄, filtered and concentrated in vacuo to dryness. The residue was purified by chromatography on silica eluting with 0-100% dichloromethane/cyclohexane. The fractions containing the desired product were combined and the solvents removed by evaporation in vacuo to give Intermediate 14 (1.2 g).

NMR (CDCl₃) δ: 9.15 (1H, d), 8.65 (1H, s), 8.34-8.24 (2H, m), 7.90 (1H, d)

Intermediate 15

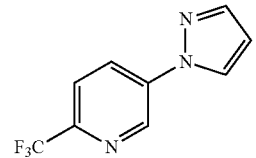 [SMILES: FC(F)(F)c1ccc(-n2cccn2)cn1]

A mixture of 5-bromo-2-(trifluoromethyl)pyridine (2.0 g, 8.85 mmol), pyrazole (904 mg, 13.28 mmol), copper (II) oxide (63 mg, 0.443 mmol), salicylaldoxime (243 mg, 1.77 mmol), Cs₂CO₃ (4.62 g, 14.16 mmol) and acetonitrile (15 mL) was heated at 82° C. under nitrogen for 24 hours. After cooling to room temperature, the mixture was diluted with dichloromethane, filtered and concentrated in vacuo to dryness. The residue was extracted with dichloromethane, washed with water, dried with Na₂SO₄, filtered and concentrated in vacuo to dryness. The residue was purified by chromatography on silica eluting with 0-35% ethyl acetate/cyclohexane. The fractions containing the desired product were combined and the solvents removed by evaporation in vacuo to give Intermediate 15 (1.19 g) as a white solid.

LCMS (Method 2) Rt 3.11 min; m/z (M+H)⁺ 214

The following compounds were prepared using a similar method as described in Example 6.

| No | Structure | LCMS Method | Rt (min) | Mass [M − H]− |
|---|---|---|---|---|
| 117 | ![structure] | Method 1 | 3.41 | 349 |
| 137 | ![structure] | Method 1 | 3.64 | 342 |

Example 7: Compound 108

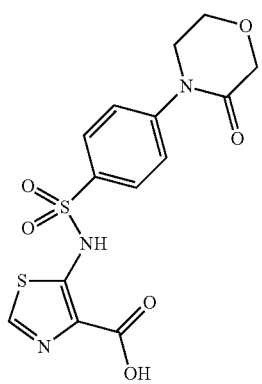 [SMILES: O=C(O)c1ncsc1NS(=O)(=O)c1ccc(N2CCOCC2=O)cc1]

Intermediate 16 (161 mg, 0.288 mmol) was stirred with 95% TFA(aq) (3 mL) at room temperature for 2 hours. The solvent was removed in vacuo and the residue azeotroped with toluene to dryness. The product was triturated with diethyl ether from methanol. The solid was collected by filtration, washed with diethyl ether and dried under vacuum to give Compound 108 (75.7 mg) as a white solid.

1H NMR (DMSO-d$_6$) δ: 8.55 (1H, s), 7.90-7.83 (2H, m), 7.70-7.63 (2H, m), 4.22 (2H, s), 3.99-3.94 (2H, m), 3.81-3.76 (2H, m) LCMS (Method 1) Rt 2.50 min; m/z (M−H)$^-$ 382

Intermediate 16

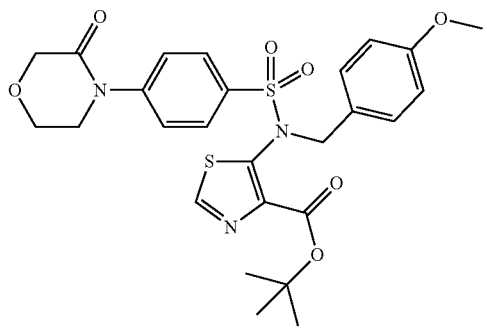 [SMILES: COc1ccc(CN(c2scnc2C(=O)OC(C)(C)C)S(=O)(=O)c2ccc(N3CCOCC3=O)cc2)cc1]

A mixture of Intermediate 17 (200 mg, 0.371 mmol), morpholin-3-one (45 mg, 0.445 mmol), Pd$_2$dba$_3$ (4 mg, 0.004 mmol), xantphos (7 mg, 0.011 mmol), Cs$_2$CO$_3$ (170 mg, 0.519 mmol) and dry dioxan (5 mL) was heated at 100° C. under nitrogen for 20 hours. After cooling to room temperature, the mixture was diluted with ethyl acetate, filtered to remove inorganic residues and concentrated in vacuo to dryness. The residue was purified by chromatography on silica eluting with 0-1% methanol/ethyl acetate. The fractions containing the desired product were combined and the solvents removed by evaporation in vacuo to give Intermediate 16 (161 mg) as a yellow glass.

LCMS (Method 2) Rt 3.49 min; m/z (M+H)$^+$ 560

Intermediate 17

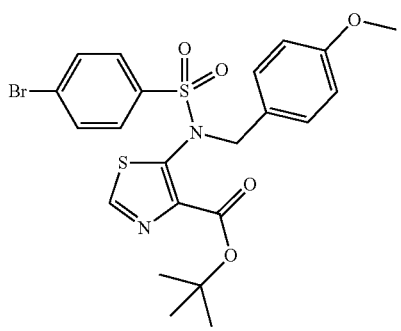

Intermediate 2 (2.0 g, 6.24 mmol) was dissolved in dry tetrahydrofuran (60 mL). To this, sodium hydride (60% disp. in oil; 325 mg, 8.11 mmol) was added at room temperature and the mixture was stirred for 30 minutes. To this, 4-bromobenzenesulfonyl chloride (2.4 g, 9.36 mmol) was added and the mixture stirred at room temperature for 20 hours. Water was added, and the reaction mixture extracted with ethyl acetate. The organic layer was washed with brine, dried with Na$_2$SO$_4$, filtered and concentrated in vacuo to dryness. The residue was purified by chromatography on silica eluting with 10-25% ethyl acetate/cyclohexane. The fractions containing the desired product were combined and the solvent removed by evaporation in vacuo to give Intermediate 17 (2.02 g).

LCMS (Method 2) Rt 3.95 min; m/z (M+H)$^+$ 492

The following compounds were prepared using a similar method as described in Example 7.

| No | Structure | LCMS Method | Rt (min) | Mass [M − H]− |
|---|---|---|---|---|
| 109 | 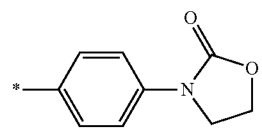 [SMILES: *c1ccc(N2CCOC2=O)cc1] | Method 1 | 2.76 | 368 |
| 113 | 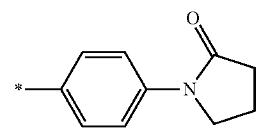 [SMILES: *c1ccc(N2CCCC2=O)cc1] | Method 1 | 2.88 | 366 |
| 149 | 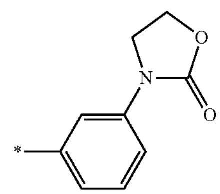 [SMILES: *c1cccc(N2CCOC2=O)c1] | Method 1 | 2.78 | 368 |
| 152 | 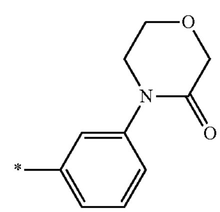 [SMILES: *c1cccc(N2CCOCC2=O)c1] | Method 1 | 2.52 | 382 |
| 153 | 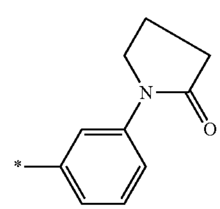 [SMILES: *c1cccc(N2CCCC2=O)c1] | Method 1 | 2.85 | 366 |
| 142 | 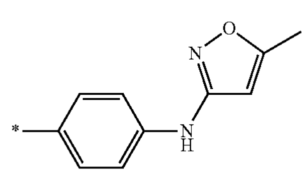 [SMILES: *c1ccc(Nc2cc(C)on2)cc1] | Method 1 | 3.41 | 379 |
| 175 | 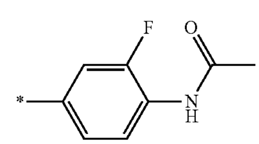 [SMILES: *c1ccc(NC(C)=O)c(F)c1] | Method 1 | 2.64 | 358 |

Example 8: Compound 116

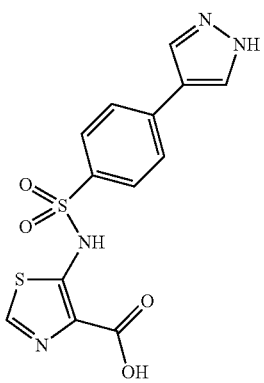 [SMILES: O=C(O)c1ncsc1NS(=O)(=O)c1ccc(-c2cn[nH]c2)cc1]

Intermediate 18 (132 mg, 0.251 mmol) was treated with 95% TFA(aq) (4 mL) and the mixture stirred at room temperature for 90 minutes. The solvent was removed in vacuo and the residue sonicated in methanol. The mixture was purified by reverse phase HPLC. The fractions containing the desired product were combined and lyophilised to give Compound 116 (6.5 mg).

1H NMR (DMSO-$d_6$) δ: 8.43 (1H, br s), 8.16 (2H, s), 7.81-7.73 (4H, m)

LCMS (Method 1) Rt 2.77 min; m/z (M−H)⁻ 349

Intermediate 18

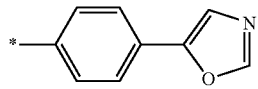

A mixture of Intermediate 17 (200 mg, 0.371 mmol), 1-Boc-pyrazole-4-boronic acid pinacol ester (132 mg, 0.45 mmol), Pd(dppf)Cl$_2$.DCM (15 mg, 0.019 mmol), Cs$_2$CO$_3$ (169 mg, 0.519 mmol), dioxan (4 mL) and water (1 mL) was heated at 90° C. for 18 hours. The mixture was diluted with ethyl acetate. The organic layer was washed with water, brine, dried with Na$_2$SO$_4$, filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 18 (1.19 g) as a white solid.

LCMS (Method 2) Rt 3.51 min; m/z (M+H)⁺ 527

The following compounds were prepared using a similar method as described in Example 8. Compound 118 was prepared using 1-N-Boc-4-(4,4,5,5-tetramethyl-[1,3,2]dioxaborolan-2-yl)-3,6-dihydro-2H-pyridine, followed by hydrogenation prior to TFA deprotection.

| No | Structure | LCMS Method | Rt (min) | Mass [M − H]− |
|---|---|---|---|---|
| 115 | 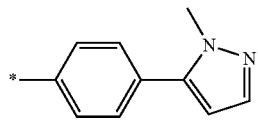 | Method 1 | 2.93 | 350 |
| 105 | 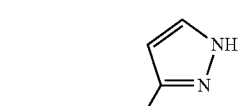 | Method 1 | 3.01 | 363 |
| 150 | 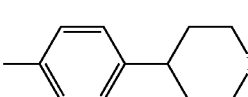 | Method 1 | 2.90 | 349 |
| 118 | 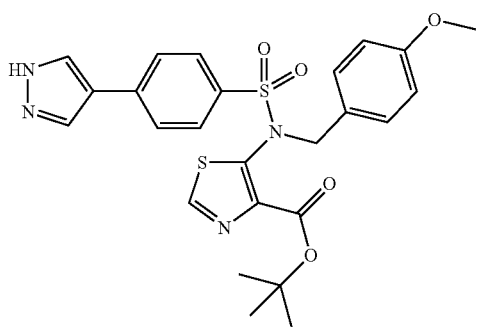 [SMILES: COc1ccc(CN(c2scnc2C(=O)OC(C)(C)C)S(=O)(=O)c2ccc(-c3cn[nH]c3)cc2)cc1] | Method 1 | 2.09 | 366 |

Example 9: Compound 138

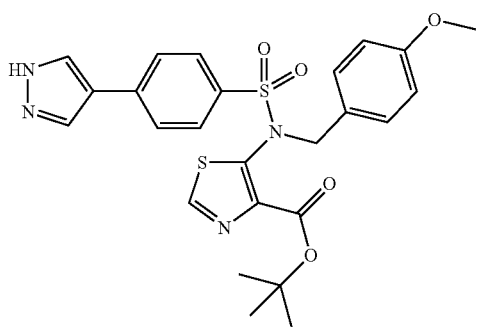 [SMILES: COc1ccc(CN(c2scnc2C(=O)OC(C)(C)C)S(=O)(=O)c2ccc(-c3cn[nH]c3)cc2)cc1]

Intermediate 19 (136 mg, 0.25 mmol) was treated with 95% TFA(aq) (2 mL) and the mixture stirred at room temperature for 2 hours. The solvent was removed in vacuo and the residue azeotroped with toluene to dryness. The residue was triturated with diethyl ether/pentane and the solid was purified by reverse phase HPLC. The fractions containing the desired product were combined and lyophilised to give Compound 138 (47.3 mg) as a white solid.

1H NMR (DMSO-$d_6$) δ: 8.53 (1H, s), 8.42 (1H, d), 7.76 (1H, dd), 6.88 (1H, d), 3.66-3.59 (4H, m), 1.66-1.57 (2H, m), 1.56-1.46 (4H, m) LCMS (Method 1) Rt 3.52 min; m/z (M−H)⁻ 367

Intermediate 19

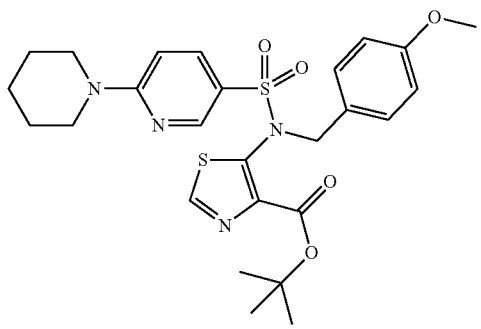 [SMILES: COc1ccc(CN(c2scnc2C(=O)OC(C)(C)C)S(=O)(=O)c2ccc(N3CCCCC3)nc2)cc1]

A mixture of Intermediate 20 (125 mg, 0.252 mmol), piperidine (0.289 mL, 2.92 mmol) and acetonitrile (2 mL) was heated by microwave irradiation for 10 minutes at 100° C. The solvent was removed in vacuo and the residue purified by chromatography on silica eluting with 5-50% ethyl acetate/cyclohexane. The fractions containing the desired product were combined and the solvents removed by evaporation in vacuo to give Intermediate 19 (136 mg) as a colourless oil.

LCMS (Method 4) Rt 4.23 min; m/z (M+H)$^+$ 545

Intermediate 20

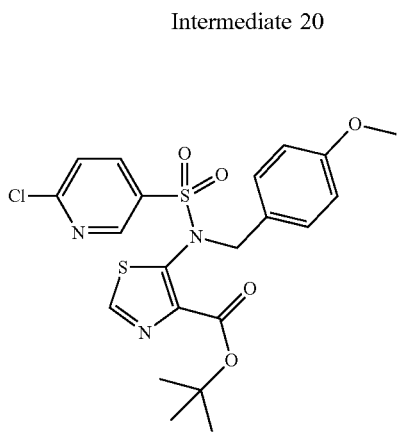

Intermediate 2 (1.2 g, 3.73 mmol) and 15-crown-5 (0.1 mL) were dissolved in dry tetrahydrofuran (50 mL). To this, sodium hydride (60% disp. in oil; 224 mg, 5.6 mmol) was added at room temperature and the mixture was stirred for 30 minutes. To this, 2-chloropyridine-5-sulfonyl chloride (950 mg, 4.48 mmol) was added and the mixture stirred at room temperature for 20 hours. The reaction mixture was diluted with water and extracted with ethyl acetate. The organic layer was washed with brine, dried with Na$_2$SO$_4$, filtered and concentrated in vacuo to dryness. The residue was purified by chromatography on silica eluting with 0-50% ethyl acetate/cyclohexane. The fractions containing the desired product were combined and the solvents removed by evaporation in vacuo to give Intermediate 20 (1.1 g) as an orange solid.

LCMS (Method 2) Rt 4.00 min; m/z (M+H)$^+$ 496

The following compounds were prepared using a similar method as described in Example 9. Compounds 157, 162, 164, 154, 161, 158 and 159 were prepared using the appropriate mono-Boc protected di amines.

| No | Structure | LCMS Method | Rt (min) | Mass [M−H]− |
|---|---|---|---|---|
| 160 | 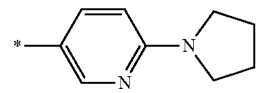 [SMILES: *c1ccc(N2CCCC2)nc1] | Method 1 | 2.59 | 353 |
| 157 | 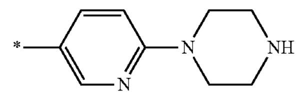 [SMILES: *c1ccc(N2CCNCC2)nc1] | Method 1 | 1.92 | 368 |
| 162 | 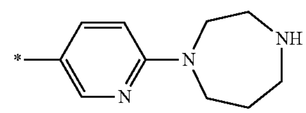 [SMILES: *c1ccc(N2CCCNCC2)nc1] | Method 1 | 1.98 | 382 |
| 164 | 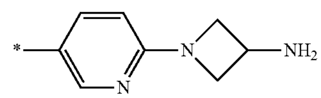 [SMILES: *c1ccc(N2CC(N)C2)nc1] | Method 1 | 1.74 | 354 |
| 167 | 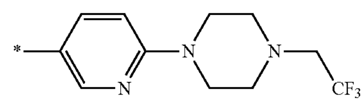 | Method 1 | 3.81 | 450 |
| 154 | 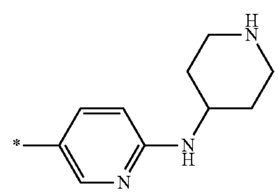 [SMILES: *c1ccc(NC2CCNCC2)nc1] | Method 1 | 1.87 | 382 |
| 140 | 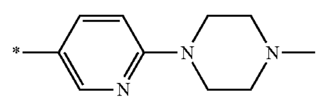 [SMILES: *c1ccc(N2CCN(C)CC2)nc1] | Method 1 | 1.93 | 382 |
| 139 | 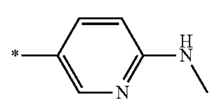 [SMILES: *c1ccc(NC)nc1] | Method 1 | 1.98 | 313 |
| 155 | 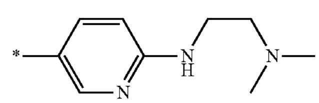 [SMILES: *c1ccc(NCCN(C)C)nc1] | Method 1 | 1.88 | 370 |
| 161 | 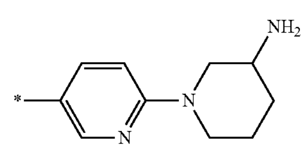 [SMILES: *c1ccc(N2CCCC(N)C2)nc1] | Method 1 | 2.06 | 382 |
| 158 | 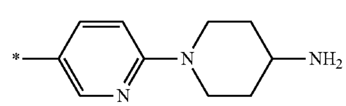 [SMILES: *c1ccc(N2CCC(N)CC2)nc1] | Method 1 | 2.01 | 382 |
| 159 | 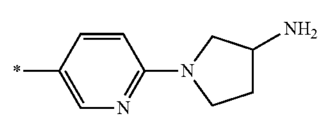 [SMILES: *c1ccc(N2CCC(N)C2)nc1] | Method 1 | 1.83 | 368 |

Example 10: Compound 141

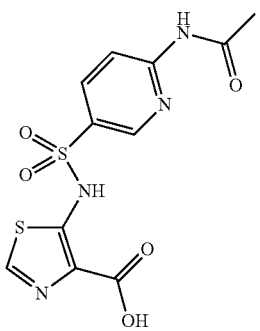 [SMILES: CC(=O)Nc1ccc(S(=O)(=O)Nc2scnc2C(=O)O)cn1]

Intermediate 21 (116 mg, 0.224 mmol) was treated with 95% TFA(aq) (2 mL) and the mixture stirred at room temperature for 1 hour. The solvent was removed in vacuo and the residue azeotroped with toluene to dryness. The residue was purified by reverse phase HPLC. The fractions containing the desired product were combined and the solvents removed by lyophilisation. The residue was then sonicated in methanol, filtered and dried under vacuum to give Compound 141 (19.1 mg) as an off white solid.

1H NMR (DMSO-$d_6$) δ: 10.96 (1H, s), 8.65 (1H, m), 8.57 (1H, br s), 8.22-8.11 (2H, m), 2.12 (3H, s) LCMS (Method 1) Rt 2.42 min; m/z (M−H)⁻ 341

Intermediate 21

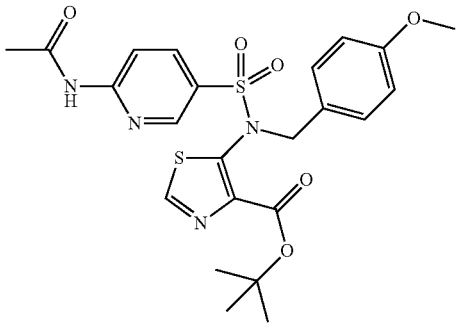 [SMILES: COc1ccc(CN(c2scnc2C(=O)OC(C)(C)C)S(=O)(=O)c2ccc(NC(C)=O)nc2)cc1]

A mixture of Intermediate 20 (125 mg, 0.252 mmol), acetamide (18 mg, 0.302 mmol), Pd₂dba₃ (2 mg, 0.0025 mmol), xantphos (5 mg, 0.0076 mmol), Cs₂CO₃ (115 mg, 0.353 mmol) and dry dioxan (5 mL) was heated at 100° C. under nitrogen for 20 hours. The mixture was diluted with ethyl acetate, washed with water, brine, dried with Na₂SO₄, filtered and concentrated in vacuo to dryness. The residue was purified by chromatography on silica eluting with 0-5% methanol/dichloromethane. The fractions containing the desired product were combined and the solvents removed by evaporation in vacuo to give Intermediate 21 (116 mg) as an orange glass.

LCMS (Method 2) Rt 3.49 min; m/z (M+H)⁺ 519

Example 11: Compound 106

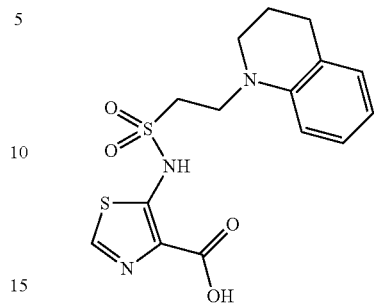

Intermediate 22 (66 mg, 0.121 mmol) was treated with 95% TFA(aq) (2 mL) and the mixture stirred at room temperature for 1 hour. The solvent was removed in vacuo and the residue soniciated with diethyl ether. After standing in diethyl ether for 18 hours the precipitate was isolated by filtration and dried under vacuum to give Compound 106 (20 mg) as an off white solid.

1H NMR (DMSO-$d_6$) δ: 8.56 (1H, s), 6.92-6.84 (2H, m), 6.52-6.42 (2H, m), 3.68-3.62 (2H, m), 3.53-3.48 (2H, m), 3.24-3.18 (2H, m), 2.65-2.59 (2H, m), 1.85-1.77 (2H, m) LCMS (Method 1) Rt 3.95 min; m/z (M−H)⁻ 366

Intermediate 22

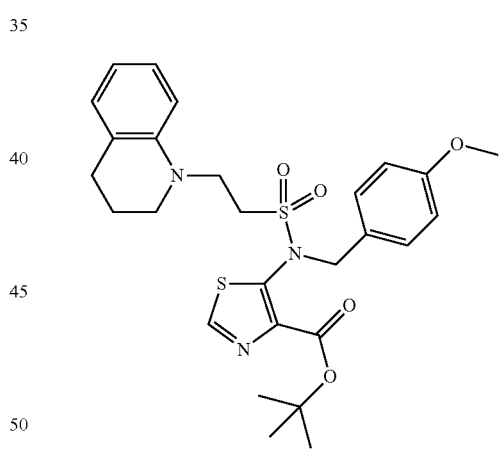

A mixture of Intermediate 23 (100 mg, 0.243 mmol), 1,2,3,4-tetrahydro-quinoline (65 mg, 0.488 mmol) and DMAP (32 mg, 0.243 mmol) in n-propanol was heated at 90° C. for 48 hours. The solvent was removed in vacuo to dryness. The residue was purified by chromatography on silica eluting with 0-50% ethyl acetate/cyclohexane. The fractions containing the desired product were combined and the solvents removed by evaporation in vacuo to give Intermediate 22 (66 mg) as a gum.

1H NMR (CDCl₃) δ: 8.57 (1H, s), 7.16-7.01 (3H, m), 6.98-6.92 (1H, m), 6.82-6.75 (2H, m), 6.66-6.57 (2H, m), 4.88 (2H, s), 3.92-3.83 (2H, m), 3.77 (3H, s), 3.46-3.38 (2H, m), 3.33-3.26 (2H, m), 2.78-2.69 (2H, m), 2.00-1.90 (2H, m), 1.65 (9H, s)

Intermediate 23

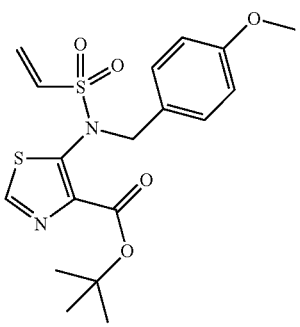 [SMILES: C=CS(=O)(=O)N(Cc1ccc(OC)cc1)c1scnc1C(=O)OC(C)(C)C]

Intermediate 2 (1.0 g, 3.12 mmol) and 15-crown-5 (690 mg, 3.12 mmol) were dissolved in dry tetrahydrofuran (30 mL). To this, sodium hydride (60% disp. in oil; 245 mg, 6.14 mmol) was added at room temperature and the mixture was stirred for 10 minutes. To this, 2-chloroethanesulfonyl chloride (760 mg, 4.69 mmol) was added at room temperature and the mixture stirred for 4 hours. The mixture was diluted with 10% citric acid solution and extracted with ethyl acetate. The organic layer was washed with brine, dried with $Na_2SO_4$, filtered and concentrated in vacuo to dryness. The residue was purified by chromatography on silica eluting with 0-50% ethyl acetate/cyclohexane. The fractions containing the desired product were combined and the solvents removed by evaporation in vacuo to give Intermediate 23 (360 mg) as a yellow glass.

1H NMR ($CDCl_3$) δ: 8.57 (1H, s), 7.19-7.11 (2H, m), 6.84-6.76 (2H, m), 6.70-6.57 (1H, m), 6.22 (1H, d), 5.98 (1H, d), 4.83 (2H, s), 3.78 (3H, s), 1.65 (9H, s)

The following compounds were prepared using a similar method as described in Example 11. Compound 107 was prepared by treating Intermediate 23 with aniline, following by treatment with acetyl chloride.

| No | Structure | LCMS Method | Rt (min) | Mass [M − H]− |
|----|-----------|-------------|----------|---------------|
| 136 | ![structure] | Method 1 | 3.46 | 340 |
| 107 | ![structure] | Method 1 | 2.94 | 368 |

Example 12: Compound 76

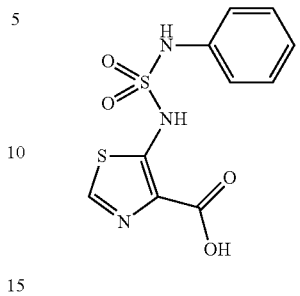

Intermediate 24 (183 mg, 0.56 mmol) was dissolved in tetrahydrofuran (6 mL) and methanol (3 mL). To this, lithium hydroxide (2M; 1.5 mL, 3.0 mmol) was added at room temperature and the mixture heated at 55° C. for 6 hours. The mixture was cooled to room temperature and stirred for 18 hours. The solvent was removed in vacuo. The residue was dissolved in water and extracted with ethyl acetate. The aqueous layer was acidified with 1M hydrochloric acid and extracted with ethyl acetate. The organic layer was washed with brine, dried with $Na_2SO_4$, filtered and concentrated in vacuo to dryness. The residue was purified by reverse phase HPLC. The fractions containing the desired product were combined and lyophilised to give Compound 106 (31.2 mg) as a white solid.

1H NMR (DMSO-$d_6$) δ: 10.53 (1H, s), 8.57 (1H, s), 7.30-7.23 (2H, m), 7.15-7.10 (2H, m), 7.09-7.03 (1H, m)
LCMS (Method 1) Rt 2.93 min; m/z (M−H)− 298

Intermediate 24

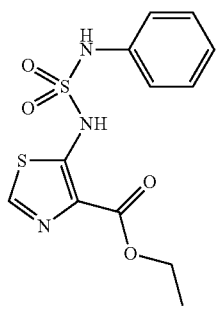 [SMILES: CCOC(=O)c1ncsc1NS(=O)(=O)Nc1ccccc1]

Intermediate 25 (1.12 g, 5.84 mmol) and 5-aminothiazole-4-carboxylic acid ethyl ester (0.9 g, 5.84 mmol) were combined in toluene (25 mL). The mixture was stirred under a nitrogen atmosphere at 60° C. for 1 hour and then at room temperature for 18 hours. The mixture was partitioned between 1M hydrochloric acid and ethyl acetate and the layers separated. The aqueous layer was extracted with ethyl acetate and the combined organic layers dried with $Na_2SO_4$, filtered and concentrated in vacuo to dryness. The residue was purified by chromatography on silica eluting with 0-70% ethyl acetate/cyclohexane. The fractions containing the desired product were combined and the solvents removed by evaporation in vacuo to give Intermediate 24 (298 mg) as a cream solid.

LCMS (Method 2) Rt 3.09 min; m/z (M+H)+ 328

Intermediate 25

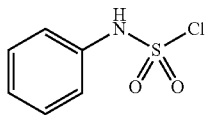 [SMILES: O=S(=O)(Cl)Nc1ccccc1]

Intermediate 26 (1.77 g, 9.1 mmol) and phosphorous pentachloride (1.70 g, 8.2 mmol) were combined in toluene (20 mL). The mixture was stirred under a nitrogen atmosphere at reflux for 4 hours. After cooling to room temperature, the solid was removed by filtration. The filtrate was concentrated in vacuo to dryness to give Intermediate 25 (1.12 g) as a yellow oil which was used without further purification.

Intermediate 26

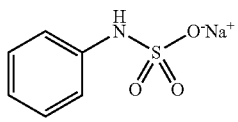

Aniline (2.28 mL, 25 mmol) and TEA (35 mL, 250 mmol) were dissolved in chloroform (50 mL). Chlorosulfonic acid (1.45 mL, 25 mmol) was added drop wise at −5° C. and the mixture stirred for 10 minutes. The mixture was concentrated in vacuo and the solid dissolved in sodium hydroxide solution (1M; 75 mL, 75 mmol). The mixture was concentrated in vacuo to dryness. The product was recrystallised from hot ethanol, collected by filtration and dried under vacuum to give Intermediate 26 (2.78 g) as a white solid.

1H NMR (DMSO-$d_6$) δ: 7.07-6.90 (4H, m), 6.61-6.50 (1H, m)

The following compounds were prepared using a similar method as described in Example 12.

| No | Structure | LCMS Method | Rt (min) | Mass [M − H]− |
|---|---|---|---|---|
| 43 | *—NH—(2-Cl-C6H4CH2) | Method 1 | 3.24 | 346 |
| 44 | *—NH—(3-CF3-C6H4CH2) | Method 1 | 3.62 | 380 |

Example 13: Compound 75

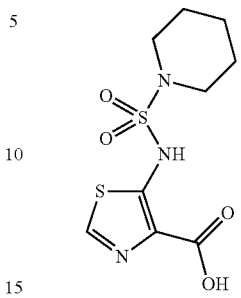

Intermediate 27 (0.195 mg, 0.61 mmol) was dissolved in tetrahydrofuran (3.6 mL) and methanol (1.8 mL). To this, lithium hydroxide (2M; 0.9 mL, 1.8 mmol) was added at room temperature and the mixture heated to 40° C. under nitrogen for 17 hours. The solvents were removed in vacuo. The residue was dissolved in water and extracted with ethyl acetate. The aqueous layer was acidified with 1M hydrochloric acid and extracted with ethyl acetate. The organic layer was dried with $Na_2SO_4$, filtered and concentrated in vacuo to dryness. The product was purified by reverse phase HPLC. The fractions containing the desired product were combined and concentrated in vacuo to a minimal volume of water. The product was collected by filtration and dried under vacuum to give Compound 75 (37.6 mg) as a white solid.

1H NMR (DMSO-$d_6$) δ: 8.60 (1H, s), 3.17-3.10 (4H, m), 1.55-1.39 (6H, m)

LCMS (Method 1) Rt 3.20 min; m/z (M−H)− 290

Intermediate 27

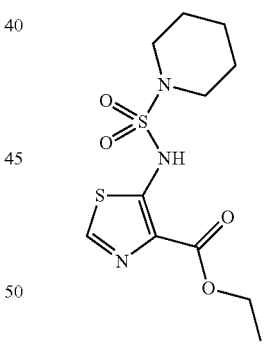

A mixture of Intermediate 28 (1.01 g, 6.15 mmol), ethyl 5-bromothiazole-4-carboxylate (0.48 g, 2.03 mmol), $Pd_2dba_3$ (186 mg, 0.2 mmol), xantphos (353 mg, 0.61 mmol), $Cs_2CO_3$ (3.31 g, 10.2 mmol) and dry dioxan (15 mL) was heated at 100° C. under argon for 17 hours. The mixture was concentrated in vacuo and partitioned between water and ethyl acetate. The aqueous layer was acidified with 1M hydrochloric acid and extracted with ethyl acetate. The organic layer was dried with $Na_2SO_4$, filtered and concentrated in vacuo to dryness. The residue was purified by chromatography on silica eluting with 0-50% ethyl acetate/cyclohexane. The fractions containing the desired product were combined and the solvents were removed by evaporation in vacuo to give Intermediate 27 (202 mg) as a yellow solid.

LCMS (Method 2) Rt 3.28 min; m/z (M+H)+ 320

Intermediate 28

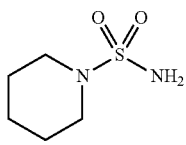

Piperidine (2.05 mL, 20 mmol) and sulfamide (1.92 g, 20 mmol) were dissolved in dioxan (20 mL). The mixture was heated at reflux for 15 hours then concentrated in vacuo to dryness. The solid was collected by filtration from dilute hydrochloric acid, washed with water and dried under vacuum to give Intermediate 28 (1.64 g) as an off white solid.

1H NMR (DMSO-$d_6$) δ: 6.63 (2H, s), 3.01-2.84 (4H, m), 1.63-1.49 (4H, m), 1.48-1.35 (2H, m)

The following compounds were prepared using a similar method as described in Example 13.

| No | Structure | LCMS Method | Rt (min) | Mass [M − H]− |
|---|---|---|---|---|
| 77 | *—N(CH3)CH2Ph | Method 1 | 3.69 | 326 |
| 88 | *—N(CH3)Ph | Method 1 | 3.39 | 312 |
| 147 | *—N(indoline) | Method 1 | 3.52 | 324 |

Example 14: Compound 170

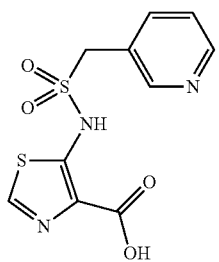 [SMILES: O=C(O)c1ncsc1NS(=O)(=O)Cc1cccnc1]

Intermediate 29 (49 mg, 0.138 mmol) was treated with 95% TFA(aq) (2 mL) and the mixture stirred at room temperature for 3 hours. The solvent was removed in vacuo and the residue azeotroped with toluene to dryness. The residue was purified by reverse phase HPLC. The fractions containing the desired product were combined and lyophilised to give Compound 170 (5.2 mg) as an off white solid.

1H NMR (DMSO-$d_6$) δ: 8.65-8.53 (2H, m), 8.33 (1H, s), 7.98-7.91 (1H, m), 7.58-7.50 (1H, m), 4.70 (2H, s) LCMS (Method 1) Rt 1.49 min; m/z (M−H)− 298

Intermediate 29

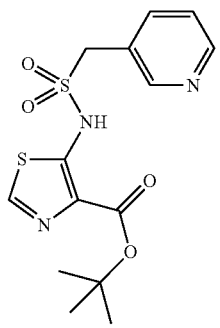 [SMILES: CC(C)(C)OC(=O)c1ncsc1NS(=O)(=O)Cc1cccnc1]

A mixture of Intermediate 30 (212 mg, 1.23 mmol), Pd$_2$dba$_3$ (47 mg, 0.051 mmol), xantphos (89 mg, 0.154 mmol), Cs$_2$CO$_3$ (468 mg, 1.44 mmol) and Intermediate 12 (1.0 mmol) in dry dioxan (5 mL) was heated at 90° C. under nitrogen for 18 hours. The mixture was extracted with ethyl acetate and washed with water. The organic layer was dried with Na$_2$SO$_4$, filtered and concentrated in vacuo to dryness. The product was purified by chromatography on silica eluting with 0-10% methanol/ethyl acetate. The fractions containing the desired product were combined and the solvents removed by evaporation in vacuo to give Intermediate 29 (49 mg).

LCMS (Method 3) Rt 2.60 min; m/z (M+H)+ 356

Intermediate 30

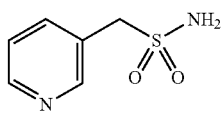 [SMILES: NS(=O)(=O)Cc1cccnc1]

Intermediate 31 (515 mg, 1.76 mmol) was treated with 95% TFA(aq) (2 mL) at room temperature and the mixture heated at 60° C. for 2 hours. The solvent was removed in vacuo and the residue azeotroped with toluene to dryness. The product was triturated with diethyl ether, collected by filtration and dried under vacuum to give Intermediate 30 (212 mg) as an off white solid.

LCMS (Method 2) Rt 0.34 min; m/z (M+H)+ 173

Intermediate 31

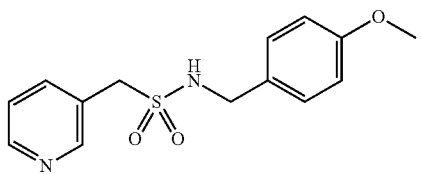 [SMILES: COc1ccc(CNS(=O)(=O)Cc2cccnc2)cc1]

Intermediate 32 (500 mg, 1.91 mmol) was dissolved in NMP (5 mL). To this, 4-methoxybenzylamine (1.25 mL, 9.55 mmol) was added at room temperature and the mixture heated to 130° C. for 18 hours. The mixture was diluted with diethyl ether and washed with water. The aqueous layer was extracted with ethyl acetate and the combined organic layers dried with Na$_2$SO$_4$, filtered and concentrated in vacuo to dryness. The residue was purified by chromatography on silica eluting with 0-10% methanol/dichloromethane. The fractions containing the desired product were combined and the solvents removed by evaporation in vacuo to give Intermediate 31 (515 mg) as a yellow solid.

LCMS (Method 2) Rt 2.04 min; m/z (M+H)$^+$ 293

Intermediate 32

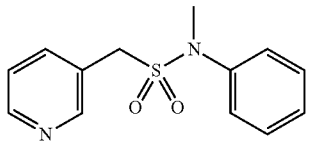 [SMILES: CN(c1ccccc1)S(=O)(=O)Cc1cccnc1]

Intermediate 33 (718 mg, 2.24 mmol) was dissolved in methanol (10 mL). To this, 1N sodium hydroxide solution (11.2 mL, 11.2 mmol) was added at room temperature and the mixture heated at 50° C. for 30 minutes. The mixture was diluted with ethyl acetate and washed with water. The organic layer was washed with brine and the combined aqueous layers extracted with ethyl acetate. The combined organic layers were dried with Na$_2$SO$_4$, filtered and concentrated in vacuo to give Intermediate 32 (500 mg).

LCMS (Method 2) Rt 2.20 min; m/z (M+H)$^+$ 263

Intermediate 33

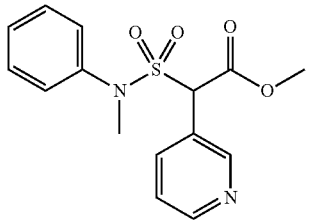 [SMILES: COC(=O)C(c1cccnc1)S(=O)(=O)N(C)c1ccccc1]

Intermediate 34 (500 mg, 2.06 mmol), Pd(PPh$_3$)$_4$ (73 mg, 0.063 mmol), sodium hydride (60% disp. in oil; 190 mg, 4.74 mmol), 3-bromopyridine (250 mg, 1.58 mmol) and dry dioxan (15 mL) were combined at room temperature and heated to 70° C. under nitrogen for 18 hours. The mixture was diluted with ethyl acetate and washed with brine. The organic layer was dried with Na$_2$SO$_4$, filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 33 (358 mg).

LCMS (Method 2) Rt 2.76 min; m/z (M+H)$^+$ 321

Intermediate 34

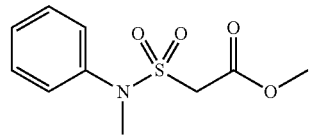 [SMILES: COC(=O)CS(=O)(=O)N(C)c1ccccc1]

N-methylaniline (4.1 g, 34.28 mmol) was dissolved in dichloromethane (50 mL). To this, a solution of methyl 2-(chlorosulfonyl)acetate (3.3 g, 19.12 mmol) in dichloromethane (20 mL) was added drop wise at 0° C. The mixture was allowed to warm to room temperature and stirred for 18 hours. The mixture was diluted with dichloromethane. The organic layer was washed with water, 1N hydrochloric acid solution and brine. The organic layer was dried with Na$_2$SO$_4$, filtered and concentrated in vacuo to dryness. The residue was purified by chromatography on silica eluting with 0-40% ethyl acetate/cyclohexane. The fractions containing the desired product were combined and the solvents removed by evaporation in vacuo to give Intermediate 34 (4.47 g).

1H NMR (CDCl$_3$) δ: 7.52-7.28 (5H, m), 3.96 (2H, s), 3.79 (3H, s), 3.41 (3H, s)

Example 15: Compound 151

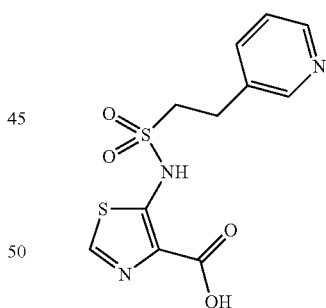

Intermediate 35 (20 mg, 0.0409 mmol) was treated with 95% TFA(aq) (2 mL) at room temperature and the mixture stirred for 1 hour. The solvent was removed in vacuo and the residue azeotroped with toluene to dryness. The residue was purified by reverse phase HPLC. The fractions containing the desired product were combined and lyophilised to give Compound 151 (8 mg) as an off white solid.

1H NMR (DMSO-d$_6$) δ: 8.68 (1H, s), 8.61 (1H, d), 8.44 (1H, s), 8.15 (1H, d), 7.66 (1H, dd), 3.63 (2H, t), 3.15 (2H, t) (1001329)

LCMS (Method 1) Rt 1.41 min; m/z (M−H)$^-$ 312

Intermediate 35

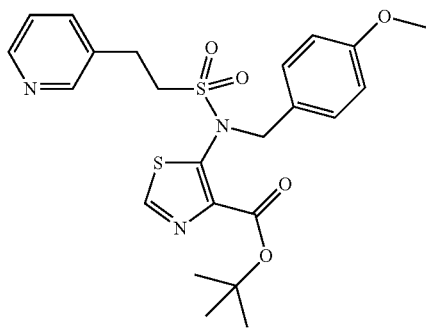 [SMILES: COc1ccc(CN(c2scnc2C(=O)OC(C)(C)C)S(=O)(=O)CCc2cccnc2)cc1]

Intermediate 36 (90 mg, 0.18 mmol) was dissolved in ethanol (5 mL). To this, Pd(OH)$_2$ (20% on carbon, 10 mg) was added and the mixture stirred at room temperature under a hydrogen atmosphere for 24 hours. Additional Pd(OH)$_2$ (20% on carbon, 10 mg) was added and the mixture stirred under a hydrogen atmosphere for 24 hours. The reaction mixture was filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 35 (20 mg).

LCMS (Method 3) Rt 2.69 min; m/z (M+H)$^+$ 490

Intermediate 36

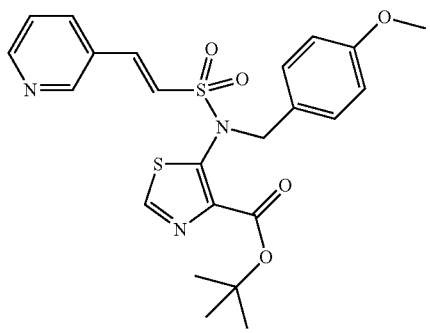 [SMILES: COc1ccc(CN(c2scnc2C(=O)OC(C)(C)C)S(=O)(=O)/C=C/c2cccnc2)cc1]

A mixture of Intermediate 23 (164 mg, 0.4 mmol), 3-bromopyridine (76 mg, 0.48 mmol), TTBP (26 mg, 0.08 mmol), Pd$_2$dba$_3$ (37 mg, 0.04 mmol), N,N-dicyclohexylmethylamine (156 mg, 0.8 mmol) and dioxan (4 mL) was heated by microwave irradiation at 110° C. for 1 hour then thermally at reflux for 6 hours. The mixture was diluted with ethyl acetate. The organic layer was washed with water, brine, dried with MgSO$_4$, filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 36 (100 mg) as a gum.

1H NMR (CDCl$_3$) δ: 8.71 (1H, d), 8.64 (1H, dd), 8.59 (1H, s), 7.77 (1H, dt), 7.41-7.30 (2H, m), 7.20-7.13 (2H, m), 6.99 (1H, d), 6.84-6.76 (2H, m), 4.87 (2H, s), 3.77 (3H, s), 1.56 (9H, s)

Example 16: Compound 165

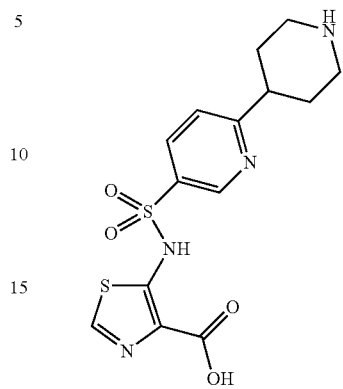

Intermediate 37 (165 mg, 0.248 mmol) was treated with 95% TFA(aq) (10 mL) and the mixture stirred at room temperature for 2 hours. The solvent was removed in vacuo and the residue azeotroped with toluene to dryness. The residue was purified by reverse phase HPLC. The fractions containing the desired product were combined and lyophilised to give Compound 165 (11 mg) as an off white solid.

1H NMR (DMSO-d$_6$) δ: 8.81 (1H, d), 8.10 (1H, s), 8.03 (1H, dd), 7.40 (1H, d), 3.40-3.10 (2H, obs), 3.09-2.92 (3H, m), 2.03-1.92 (2H, m), 1.92-1.78 (2H, m)

LCMS (Method 1) Rt 1.85 min; m/z (M–H)$^-$ 367

Intermediate 37

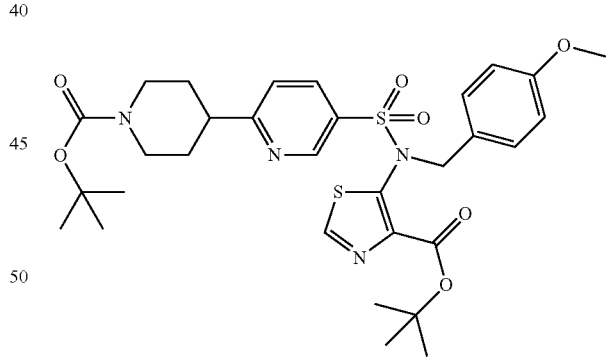

Intermediate 38 (200 mg, 0.312 mmol) was dissolved in ethanol (4 mL). To this, Pd(OH)$_2$ (20% on carbon, 25 mg) was added and the mixture stirred at room temperature under a hydrogen atmosphere for 24 hours. Additional Pd(OH)$_2$ (20% on carbon, 25 mg) was added and the mixture stirred under a hydrogen atmosphere for 3 days. The reaction mixture was filtered and concentrated in vacuo to dryness to give Intermediate 37 (180 mg).

1H NMR (CDCl$_3$) δ: 8.87 (1H, d), 8.58 (1H, s), 7.92 (1H, dd), 7.28-7.21 (1H, obs), 7.14-7.06 (2H, m), 6.80-6.73 (2H, m), 4.92 (2H, s), 4.37-4.16 (2H, m), 3.77 (3H, s), 2.99-2.74 (3H, m), 1.98-1.82 (2H, m), 1.80-1.63 (2H, m), 1.48 (9H, s)

Intermediate 38

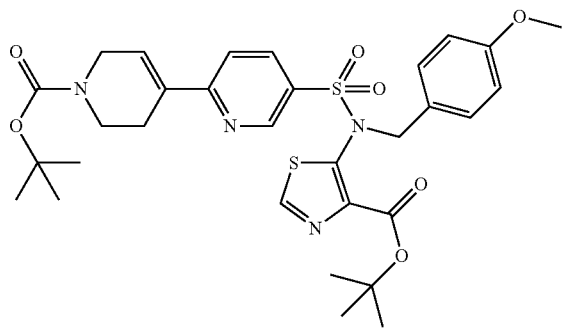 [SMILES: COc1ccc(CN(c2scnc2C(=O)OC(C)(C)C)S(=O)(=O)c2ccc(C3=CCN(C(=O)OC(C)(C)C)CC3)nc2)cc1]

A mixture of Intermediate 20 (300 mg, 0.606 mmol), N-Boc-1,2,3,6-tetrahydropyridine-4-boronic acid pinacol ester (225 mg, 0.727 mmol), Pd(dppf)Cl$_2$.DCM (25 mg, 0.0303 mmol), Cs$_2$CO$_3$ (276 mg, 0.0848 mmol), dioxan (6 mL) and water (1 mL) was heated at 95° C. for 10 hours. N-Boc-1,2,3,6-tetrahydro-pyridine-4-boronic acid pinacol ester (225 mg, 0.727 mmol), Pd(dppf)Cl$_2$.DCM (25 mg, 0.0303 mmol) were added and the mixture heated at 95° C. for 18 hours. The mixture was diluted with ethyl acetate, washed with water, brine, dried with MgSO$_4$, filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 38 (1.19 g) as a yellow gum.

1H NMR (CDCl$_3$) δ: 8.86 (1H, d), 8.58 (1H, s), 7.93 (1H, dd), 7.43 (1H, d), 7.15-7.08 (2H, m), 6.83-6.74 (3H, m), 4.92 (2H, s), 4.21-4.15 (2H, m), 3.77 (3H, s), 3.69-3.60 (2H, m), 2.68-2.59 (2H, m), 1.50 (9H, s)

Example 17: Compound 156

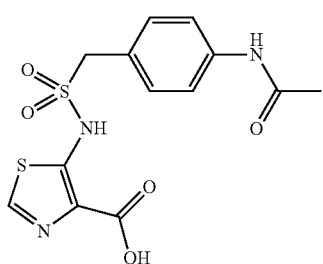 [SMILES: CC(=O)Nc1ccc(CS(=O)(=O)Nc2scnc2C(=O)O)cc1]

Intermediate 39 (55 mg, 0.104 mmol) was treated with 95% TFA(aq) (1.5 mL) at room temperature and the mixture stirred for 2 hours. The solvent was removed in vacuo and the residue azeotroped with toluene to dryness. The residue was triturated with methanol and the solid was purified by reverse phase HPLC. The fractions containing the desired product were combined and lyophilised to give Compound 156 (15 mg) as a white solid.

1H NMR (DMSO-d$_6$) δ: 9.96 (1H, s), 8.40 (1H, s), 7.50 (2H, d), 7.20 (2H, d), 4.60 (2H, s), 2.03 (3H, s) LCMS (Method 1) Rt 2.46 min; m/z (M−H)⁻ 354

Intermediate 39

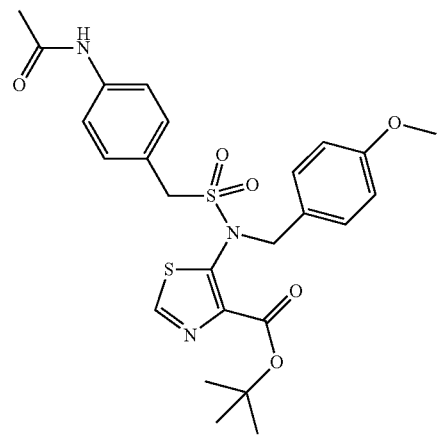 [SMILES: COc1ccc(CN(c2scnc2C(=O)OC(C)(C)C)S(=O)(=O)Cc2ccc(NC(C)=O)cc2)cc1]

A mixture of Intermediate 40 (298 mg, 0.538 mmol), acetamide (38.2 mg, 0.646 mmol), Pd$_2$dba$_3$ (9.9 mg, 0.0108 mmol), xantphos (18.7 mg, 0.0323 mmol), Cs$_2$CO$_3$ (246 mg, 0.754 mmol) and dry dioxan (7.3 mL) was heated at 100° C. under argon for 19 hours. The mixture was filtered and the solid washed with dioxan, ethyl acetate and a small volume of water. The filtrate was concentrated in vacuo to dryness, diluted with ethyl acetate and washed with 0.25M hydrochloric acid. The aqueous layer was washed with ethyl acetate and the combined organic layers washed with brine, dried with MgSO$_4$, filtered and concentrated in vacuo to dryness. The residue was purified by chromatography on silica eluting with 0-40% ethyl acetate/dichloromethane. The fractions containing the desired product were combined and the solvents removed by evaporation in vacuo to give Intermediate 39 (55 mg) as a yellow glass.

LCMS (Method 3) Rt 3.11 min; m/z (M+H)⁺ 532

Intermediate 40

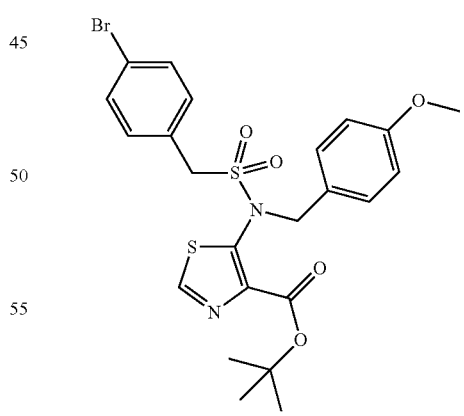

Sodium hydride (60% disp. in oil; 73 mg, 1.83 mmol) was suspended in dry tetrahydrofuran (1.8 mL) under nitrogen. To this, a solution of Intermediate 2 (450 mg, 1.404 mmol) in dry tetrahydrofuran (7.2 mL) was added at room temperature and the mixture was stirred for 30 minutes. To this, a solution of (4-bromophenyl)methanesulfonyl chloride (492 mg, 1.83 mmol) in dry tetrahydrofuran (1.8 mL) was added and the mixture stirred at room temperature for 72 hours. Water was added to the reaction mixture at 0° C. and the mixture extracted with ethyl acetate. The organic layer was washed with brine, dried with MgSO₄, filtered and concentrated in vacuo to dryness. The residue was purified by chromatography on silica eluting with 0-40% ethyl acetate/cyclohexane. The fractions containing the desired product were combined and the solvents removed by evaporation in vacuo to give Intermediate 40 (298 mg) as a yellow solid.

LCMS (Method 3) Rt 4.14 min; m/z (M+H)⁺ 553

Example 18: Compound 172

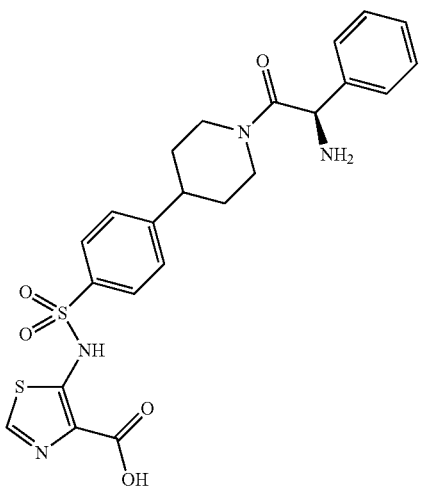 [SMILES: N[C@@H](C(=O)N1CCC(c2ccc(S(=O)(=O)Nc3scnc3C(=O)O)cc2)CC1)c1ccccc1]

Boc-D-alpha-phenylglycine (104 mg, 0.41 mmol) and HATU (115 mg, 0.3 mmol) were dissolved in DMA (1.5 mL) and stirred at room temperature for 15 minutes. To this, a solution of Intermediate 41 (150 mg, 0.28 mmol) and NMM (56 mg, 0.55 mmol) in DMA (1.5 mL) was added at room temperature and stirred for 15 hours. The solution was diluted with water and ethyl acetate. The organic layer was washed with brine, dried with MgSO₄, filtered and concentrated in vacuo to dryness. The residue was treated with 95% TFA(aq) (5 mL) at room temperature and stirred for 2 hours. The solvent was removed in vacuo and the residue was triturated with ethyl acetate. The solid was purified by reverse phase HPLC. The fractions containing the desired product were combined and lyophilised to give Compound 172 (35 mg) as a white solid.

1H NMR (DMSO-d₆) δ: 8.51 (3H, br s), 8.09 (1H, d), 7.68 (1H, d), 7.59 (1H, d), 7.55-7.44 (5H, m), 7.30 (1H, d), 7.04 (1H, d), 5.67-5.54 (1H, m), 4.59-4.50 (1H, m), 3.97-3.75 (1H, m), 3.15-3.04 (1H, m), 2.85-2.63 (3H, m), 1.89-1.69 (1H, m), 1.65-1.39 (1H, m), 1.37-1.16 (1H, m)

LCMS (Method 1) Rt 2.65 min; m/z (M−H)⁻ 499

Intermediate 41

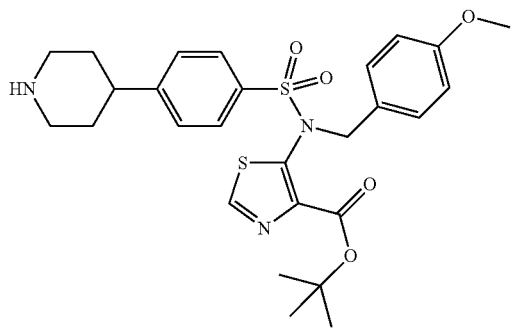 [SMILES: COc1ccc(CN(c2scnc2C(=O)OC(C)(C)C)S(=O)(=O)c2ccc(C3CCNCC3)cc2)cc1]

Intermediate 42 (5.19 g, 8.1 mmol) was dissolved in methanol (50 mL) and tetrahydrofuran (30 mL). To this, a solution of potassium carbonate (5.6 g, 40.5 mmol) in water (15 mL) was added at room temperature and stirred for 1.5 hours. The mixture was concentrated in vacuo, diluted with water and extracted with dichloromethane. The organic layer was washed with brine, dried with MgSO₄, filtered and concentrated in vacuo to dryness. The residue was purified by chromatography on silica eluting with 0-10% 2M NH₃ in methanol/dichloromethane. The fractions containing the desired product were combined, the solvents removed by evaporation in vacuo and the solid triturated with diethyl ether to give Intermediate 41 (2.60 g).

1H NMR (CDCl₃) δ: 8.55 (1H, s), 7.68 (2H, d), 7.32 (2H, d), 7.10 (2H, d), 6.76 (2H, d), 4.88 (2H, s), 3.76 (3H, s), 3.26-3.15 (2H, m), 2.81-2.61 (3H, m), 1.87-1.76 (2H, m), 1.72-1.54 (3H, m), 1.49 (9H, s)

Intermediate 42

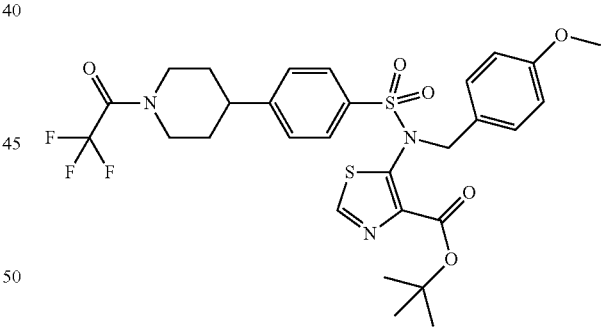

Intermediate 2 (3.26 g, 10.21 mmol) and 15-crown-5 (224 mg, 1.02 mmol) were dissolved in dry tetrahydrofuran (90 mL). To this, sodium hydride (60% disp. in oil; 610 mg, 15.31 mmol) was added at room temperature and the mixture was stirred for 10 minutes. To this, Intermediate 43 (4.0 g, 11.23 mmol) was added and the mixture stirred at room temperature for 1 hour. The mixture was poured into 10% citric acid solution and extracted with ethyl acetate. The organic layer was dried with MgSO₄, filtered and concentrated in vacuo to dryness. The residue was purified by chromatography on silica eluting with 0-100% ethyl acetate/cyclohexane. The fractions containing the desired product were combined and the solvents removed by evaporation in vacuo to give Intermediate 42 (5.19 g) as a yellow solid.

1H NMR (CDCl$_3$) δ: 8.56 (1H, s), 7.71 (2H, d), 7.30 (2H, d), 7.10 (2H, d), 6.76 (2H, d), 4.88 (2H, s), 4.79-4.66 (1H, m), 4.23-4.11 (1H, m), 3.76 (3H, s), 3.33-3.18 (1H, m), 2.97-2.79 (2H, m), 2.03-1.92 (2H, m), 1.81-1.62 (2H, m), 1.49 (9H, s)

Intermediate 43

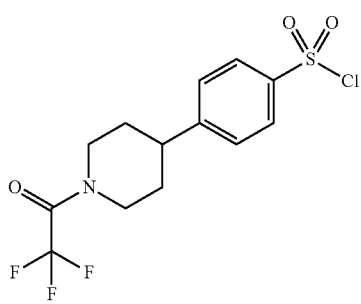 [SMILES: O=C(N1CCC(c2ccc(S(=O)(=O)Cl)cc2)CC1)C(F)(F)F]

Chlorosulfonic acid (19.63 g. 167.8 mmol) was cooled to 0° C. To this, a solution of Intermediate 44 (5.75 g, 22.37 mmol) in dichloromethane (50 mL) was added drop wise and the mixture stirred at the same temperature for 1 hour. The mixture was stirred at room temperature for 2 hours then poured into water, filtered through celite and the filtrate extracted with ethyl acetate. The organic layer was dried with MgSO$_4$, filtered and concentrated in vacuo to dryness. The residue was purified by chromatography on silica eluting with 0-40% ethyl acetate/cyclohexane. The fractions containing the desired product were combined and the solvents removed by evaporation in vacuo to give Intermediate 43 (3.27 g).

1H NMR (CDCl$_3$) δ: 8.01 (2H, d), 7.46 (2H, d), 4.80-4.70 (1H, m), 4.25-4.13 (1H, m), 3.34-3.21 (1H, m), 3.04-2.82 (2H, m), 2.09-1.96 (2H, m), 1.84-1.66 (2H, m)

Intermediate 44

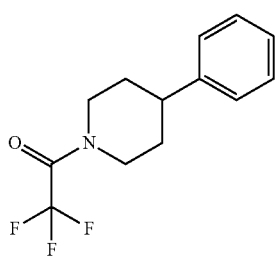 [SMILES: O=C(N1CCC(c2ccccc2)CC1)C(F)(F)F]

4-Phenylpiperidine (2.86 g, 17.76 mmol) and TEA (2.47 mL, 17.76 mmol) were dissolved in dichloromethane (40 mL) and cooled to −78° C. To this, TFAA (2.46 mL, 17.76 mmol) was added drop wise and the mixture warmed to room temperature over 30 minutes. The mixture was diluted with water and the organic layer dried with MgSO$_4$, filtered and concentrated in vacuo to dryness. The residue was purified by chromatography on silica eluting with 0-40% ethyl acetate/cyclohexane. The fractions containing the desired product were combined, the solvents removed by evaporation in vacuo to give Intermediate 44 (3.76 g) as a white solid.

1H NMR (CDCl$_3$) δ: 7.39-7.12 (5H, m), 4.76-4.62 (1H, m), 4.21-4.06 (1H, m), 3.32-3.16 (1H, m), 2.94-2.72 (2H, m), 2.06-1.90 (2H, m), 1.82-1.61 (2H, m)

The following compounds were prepared using a similar method as described in Example 18.

| No | Structure | LCMS Method | Rt (min) | Mass [M − H]− |
|---|---|---|---|---|
| 173 X6 | 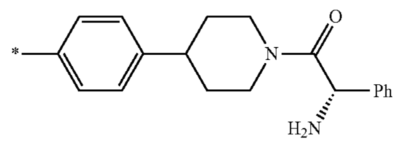 [SMILES: *c1ccc(C2CCN(C(=O)[C@@H](N)c3ccccc3)CC2)cc1] | Method 1 | 2.65 | 499 |

Example 19: Compound 102

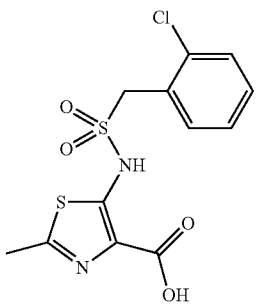 [SMILES: Cc1nc(C(=O)O)c(NS(=O)(=O)Cc2ccccc2Cl)s1]

Intermediate 45 (110 mg, 0.29 mmol) was dissolved in tetrahydrofuran (3 mL) and methanol (1 mL). To this, lithium hydroxide solution (2M; 0.73 mL, 1.47 mmol) was added at room temperature and stirred for 3 hours. The mixture was heated at 40° C. for 17 hours. The mixture was diluted with tetrahydrofuran and the solid formed was collected by filtration and dissolved in water. The solution was acidified with 1M hydrochloric acid and extracted with ethyl acetate. The organic layer was washed with brine, dried with MgSO$_4$, filtered and concentrated in vacuo to dryness to give Compound 102 (68 mg) as a white solid.

1H NMR (DMSO-d$_6$) δ: 7.52-7.42 (2H, m), 7.41-7.28 (2H, m), 4.82 (2H, s), 2.48 (3H, s) LCMS (Method 1) Rt 3.46 min; m/z (M−H)− 345

Intermediate 45

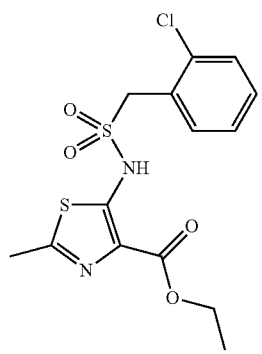 [SMILES: CCOC(=O)c1nc(C)sc1NS(=O)(=O)Cc1ccccc1Cl]

A mixture of Intermediate 46 (200 mg, 0.8 mmol), (2-chlorophenyl)-methanesulfonamide (160 mg, 0.8 mmol), $Pd_2dba_3$ (37 mg, 0.04 mmol), xantphos (69 mg, 0.12 mmol), $Cs_2CO_3$ (780 mg, 2.4 mmol) and dry dioxan (4 mL) was heated at 80° C. under argon for 20 hours. The mixture was diluted with water and extracted with ethyl acetate. The aqueous layer was acidified to pH2 with 1M hydrochloric acid and extracted with ethyl acetate. The organic layer was dried with $MgSO_4$, filtered and concentrated in vacuo to dryness. The residue was purified by chromatography on silica eluting with 0-60% ethyl acetate/cyclohexane. The fractions containing the desired product were combined and the solvents removed by evaporation in vacuo to give Intermediate 45 (116 mg) as a cream solid.

LCMS (Method 2) Rt 3.44 min; m/z $(M+H)^+$ 375

Intermediate 46

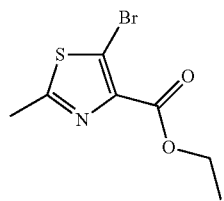

Ethyl 2-methyl-1,3-thiazole-4-carboxylate [6436-59-5] (5.0 g, 29.2 mmol) was dissolved in acetonitrile (50 mL). To this, NBS (5.7 g, 32.03 mmol) was added at room temperature and the mixture heated at reflux for 2 hours. To this, NBS (2.5 g, 14.05 mmol) was added and the mixture heated at reflux for 2 hours. To this, NBS (2.5 g, 14.05 mmol) was added and the mixture heated at reflux for 18 hours. The mixture was diluted with saturated sodium hydrogen carbonate solution and extracted with ethyl acetate. The organic layer was dried with $MgSO_4$, filtered and concentrated in vacuo to dryness. The residue was purified by chromatography on silica eluting with 0-50% ethyl acetate/cyclohexane. The fractions containing the desired product were combined and the solvents removed by evaporation in vacuo to give Intermediate 46 (1.58 g) as a cream solid.

LCMS (Method 2) Rt 2.88 min; m/z $(M+H)^+$ 250/252

Example 20: Compound 96

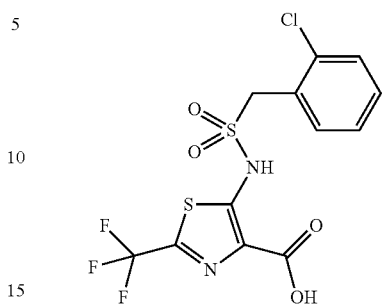

Intermediate 47 (100 mg, 0.23 mmol) was dissolved in tetrahydrofuran (2.4 mL) and methanol (0.8 mL). To this, lithium hydroxide solution (2M; 0.58 mL, 1.17 mmol) was added at room temperature and the mixture stirred for 5 hours. The mixture was heated at 40° C. for 2 hours. The mixture was acidified with saturated citric acid solution and extracted with ethyl acetate. The organic layer was washed dried with $MgSO_4$, filtered and concentrated in vacuo to dryness. The residue was purified by chromatography on silica eluting with 0-25% methanol/dichloromethane. The fractions containing the desired product were combined and the solvent removed by evaporation in vacuo to give Compound 96 (24.6 mg) as an off white solid.

1H NMR (DMSO-$d_6$) δ: 7.43-7.38 (1H, m), 7.33-7.28 (1H, m), 7.25-7.18 (2H, m), 4.40 (2H, s)

LCMS (Method 1) Rt 4.38 min; m/z $(M-H)^-$ 399

Intermediate 47

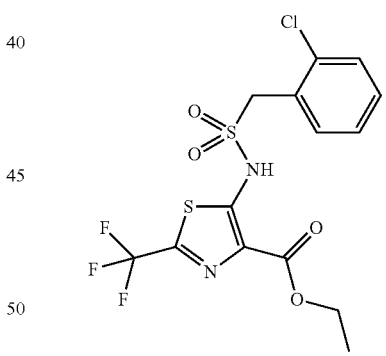

A mixture of (2-chlorophenyl)methanesulfonamide (150 mg, 0.73 mmol), Intermediate 48 (180 mg, 0.59 mmol), $Pd_2dba_3$ (27 mg, 0.03 mmol), xantphos (51 mg, 0.089 mmol), $Cs_2CO_3$ (580 mg, 1.8 mmol) and dry dioxan (3 mL) was heated at 80° C. under argon for 2 hours. The mixture was diluted with saturated citric acid solution and extracted with ethyl acetate. The organic layer was dried with $Na_2SO_4$, filtered and concentrated in vacuo to dryness. The residue was purified by chromatography on silica eluting with 0-20% ethyl acetate/cyclohexane. The fractions containing the desired product were combined and the solvents removed by evaporation in vacuo to give Intermediate 47 (103 mg) as a tan solid.

LCMS (Method 2) Rt 4.35 min; m/z $(M+H)^-$ 427

Intermediate 48

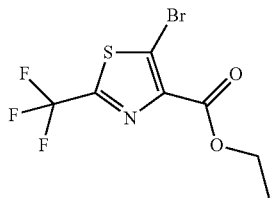

DIPA (0.35 mL, 2.5 mmol) was dissolved in dry tetrahydrofuran (5 mL) and cooled to −78° C. under nitrogen. To this, n-butyllithium (1.6M in hexanes; 1.56 mL, 2.5 mmol) was added over 5 minutes and stirred for 2 minutes. The solution was warmed to room temperature then cooled to −78° C. To this, a solution of ethyl 2-(trifluoromethyl)thiazole-4-carboxylate [133046-46-5](450 mg, 2.0 mmol) in dry tetrahydrofuran (4 mL) was added over 5 minutes and stirred at the same temperature for 45 minutes. To this, a solution of 1,2-dibromotetrachloroethane (980 mg, 3.0 mmol) in dry tetrahydrofuran (3 mL) was added over 5 minutes and warmed to room temperature over 2 hours. The reaction was quenched with saturated ammonium chloride solution. The mixture was diluted with water and extracted with dichloromethane. The organic layer was dried with MgSO$_4$, filtered and concentrated in vacuo to dryness. The residue was purified by chromatography on silica eluting with 0-25% ethyl acetate/cyclohexane. The fractions containing the desired product were combined and the solvents removed by evaporation in vacuo to give Intermediate 48 (250 mg) as an off white solid.

1H NMR (CDCl$_3$) δ: 4.47 (2H, q), 1.44 (3H, t)

Example 21: Compound 49

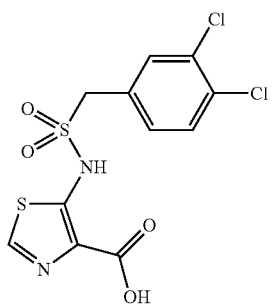 [SMILES: O=C(O)c1ncsc1NS(=O)(=O)Cc1ccc(Cl)c(Cl)c1]

Intermediate 49 (60 mg, 0.15 mmol) was dissolved in tetrahydrofuran (1.5 mL) and water (0.5 mL). To this, lithium hydroxide monohydrate (38 mg, 0.9 mmol) was added at room temperature and the mixture stirred for 72 hours. The mixture was concentrated in vacuo, diluted with water and washed with diethyl ether. The aqueous layer was acidified with 1N hydrochloric acid solution. The product was collected by filtration, washed with n-pentane and dried under vacuum to give Compound 49 (16 mg) as an off white solid.

1H NMR (DMSO-d$_6$) δ: 8.30 (1H, s), 7.60-7.50 (2H, m), 7.35-7.25 (1H, m), 7.56 (1H, t), 4.58 (2H, s)

LCMS (Method 24) Rt 3.20 min; m/z (M−H)⁻ 365

Intermediate 49

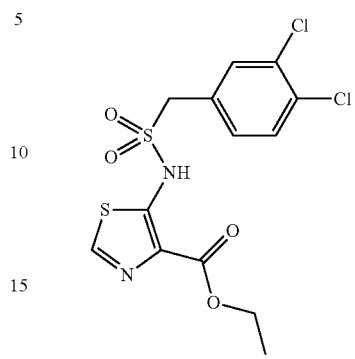

Sodium hydride (60% disp. in oil; 52 mg, 1.3 mmol) was suspended in dry tetrahydrofuran (10 mL) under argon. To this, 5-amino-thiazole-4-carboxylic acid ethyl ester (150 mg, 0.87 mmol) was added at 0° C. and the mixture was stirred for 15 minutes. To this, 3,4-dichlorobenzylsulfonyl chloride (214 mg, 0.87 mmol) was added at 0° C. and the mixture stirred at room temperature for 3 hours. The mixture was diluted with saturated ammonium chloride solution and extracted with ethyl acetate. The organic layer was washed with 1N hydrochloric acid solution, brine, dried with Na$_2$SO$_4$, filtered and concentrated in vacuo to dryness. The residue was purified by preparative TLC eluting with 50% ethyl acetate/petroleum ether to give Intermediate 49 (130 mg) as a pale brown solid.

LCMS (Method 20) Rt: 2.46 min; m/z (M+H)⁺ 395

The following compounds were prepared using a similar method as described in Example 21.

| No | Structure | LCMS Method | Rt (min) | Mass [M − H]− |
|---|---|---|---|---|
| 21 | *—⟨thiophene-2-yl⟩ | Method 27 | 3.32 | 289 |
| 22 | *—⟨2,5-dimethylthiophene⟩ | Method 18 | 2.71 | 319 |
| 35 | *—⟨C$_6$H$_4$⟩—NO$_2$ | Method 33 | 2.43 | 328 |
| 45 | *—⟨3-bromothiophen-2-yl⟩ | Method 22 | 2.35 | 369 |
| 72 | *—⟨CH$_2$⟩—⟨C$_6$H$_4$⟩—OMe | | | |

125-continued

| No | Structure | LCMS Method | Rt (min) | Mass [M−H]− |
|---|---|---|---|---|
| 3 | 2,4,6-trimethylphenyl | | | |
| 6 | 3-methoxyphenyl | | | |
| 9 | 2,3-dichlorothiophen-5-yl | | | |
| 11 | 2-(trifluoromethyl)phenyl | | | |
| 12 | 4-(trifluoromethyl)phenyl | | | |
| 98 | 1-methyl-1H-pyrazol-3-yl | | | |
| 99 | 1-methyl-1H-pyrazol-5-yl | | | |
| 23 | 2-phenylphenyl | | | |
| 38 | benzo[b]thiophen-2-yl | | | |
| 39 | 5-methylthiophen-2-yl | | | |
| 40 | 5-bromothiophen-2-yl | | | |

126-continued

| No | Structure | LCMS Method | Rt (min) | Mass [M−H]− |
|---|---|---|---|---|
| 42 | 3-bromo-2,5-dichlorothiophen-4-yl | | | |
| 47 | 3-phenyl-2-(trifluoromethyl)thiophen-4-yl | | | |
| 73 | 2-(3-(trifluoromethyl)phenyl)ethyl | | | |
| 20 | 5-phenylthiophen-2-yl | | | |
| 19 | 5-chlorothiophen-2-yl | | | |
| 167 | 5-(5-(trifluoromethyl)isoxazol-3-yl)thiophen-2-yl | | | |
| 111 | (tetrahydro-2H-pyran-4-yl)methyl | | | |
| 112 | (1-((benzyloxy)carbonyl)piperidin-4-yl)methyl | | | |
| 100 | 1-((benzyloxy)carbonyl)piperidin-4-yl | | | |

Example 22: Compound 52

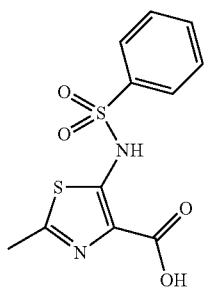 [SMILES: Cc1nc(C(=O)O)c(NS(=O)(=O)c2ccccc2)s1]

5-Amino-2-methyl-thiazole-4-carboxylic acid ethyl ester (150 mg, 0.806 mmol) was dissolved in dichloromethane (3 mL). To this, pyridine (0.195 mL, 2.42 mmol) was added at room temperature. To this, benzenesulfonyl chloride (171 mg, 0.967 mmol) was added at room temperature and stirred for 16 hours. The mixture was concentrated in vacuo, diluted with water and extracted with ethyl acetate. The organic layer was dried with $Na_2SO_4$, filtered and concentrated in vacuo to dryness. The residue was dissolved in tetrahydrofuran (3 mL) and water (1 mL). To this, lithium hydroxide monohydrate (101 mg, 2.41 mmol) was added at room temperature and stirred for 12 hours. The mixture was concentrated in vacuo and diluted with water. The mixture was acidified with 1N hydrochloric acid solution. The product was collected by filtration, washed with diethyl ether and dried under vacuum to give Compound 52 (28 mg).

1H NMR (DMSO-$d_6$) δ: 7.85-7.75 (2H, m), 7.70-7.62 (1H, m), 7.62-7.54 (2H, m), 2.75 (3H, obs)

LCMS (Method 30) Rt 4.63 min; m/z (M–H)⁻ 297

The following compounds were prepared using a similar method as described in Example 22.

| No | Structure | LCMS Method | Rt (min) | Mass [M − H]− |
|----|-----------|-------------|----------|----------------|
| 98 | 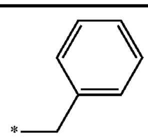          | Method 20   | 1.81     | 313            |
| 99 | 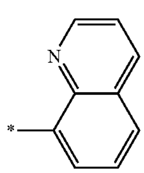 [SMILES: *c1cccc2cccnc12]          | Method 31   | 4.63     | 350            |
| 23 | 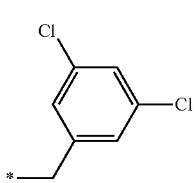 [SMILES: *Cc1cc(Cl)cc(Cl)c1]          | Method 32   | 2.78     | 381            |
| 19 | 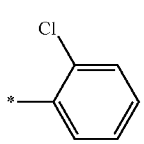 [SMILES: *c1ccccc1Cl]          | Method 29   | 2.33     | 331            |
| 37 |           | Method 17   | 2.92     | 339            |

Example 23: Compound 56

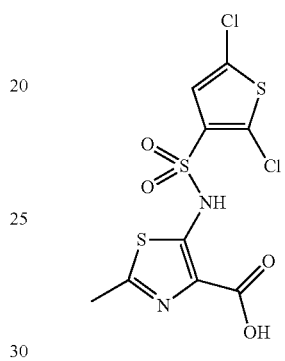

Intermediate 50 (60 mg, 0.149 mmol) was dissolved in tetrahydrofuran (3 mL) and water (1 mL). To this, lithium hydroxide monohydrate (25 mg, 0.596 mmol) was added at room temperature and stirred for 48 hours. The mixture was concentrated in vacuo and diluted with water. The mixture was acidified with 1N hydrochloric acid solution. The product was collected by filtration, washed with n-pentane and dried under vacuum to give Compound 56 (35 mg) as an off white solid.

1H NMR (DMSO-$d_6$) δ: 7.20 (1H, s)

LCMS (Method 33) Rt 1.72 min; m/z (M+H)⁺ 373

Intermediate 50

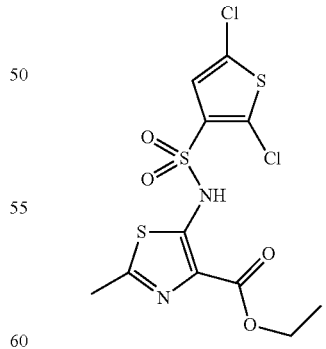

Sodium hydride (60% disp. in oil; 48 mg, 1.21 mmol) was suspended in dry tetrahydrofuran (5 mL) under nitrogen. To this, 5-amino-2-methyl-thiazole-4-carboxylic acid ethyl ester (150 mg, 0.806 mmol) was added at 0° C. and the mixture was stirred for 15 minutes. To this, 2,5-dichlorothiophene-3-sulfonyl chloride (243 mg, 0.967 mmol) was added at 0° C. and the mixture stirred at room temperature for 4 hours. Water was added to the reaction mixture at 0° C. and the mixture concentrated in vacuo. The residue was purified by preparative TLC eluting with 100% ethyl acetate to give Intermediate 50 (60 mg) as an off white solid.

LCMS (Method 33) Rt 1.91 min; m/z (M+H)+ 401

The following compounds were prepared using a similar method as described in Example 23 starting from 5-amino-2-phenyl-thiazole-4-carboxylic acid ethyl ester.

| No | Structure | LCMS Method | Rt (min) | Mass [M − H]− |
|----|-----------|-------------|----------|---------------|
| 58 | 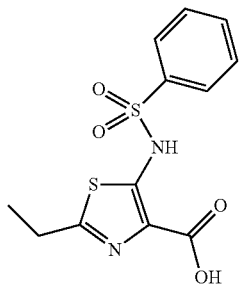 [SMILES: CCc1nc(C(=O)O)c(NS(=O)(=O)c2ccccc2)s1] | Method 33 | 1.86 | 361 |

Example 24: Compound 59

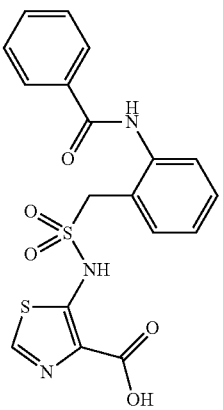

Intermediate 51 (120 mg, 0.352 mmol) was dissolved in tetrahydrofuran (3 mL) and water (1 mL). To this, lithium hydroxide monohydrate (89 mg, 2.12 mmol) was added at room temperature and stirred for 16 hours. To this, lithium hydroxide monohydrate (44 mg, 1.06 mmol) was added at room temperature and stirred for 16 hours. The mixture was concentrated in vacuo and diluted with water. The mixture was acidified with 1N hydrochloric acid solution. The product was collected by filtration, washed with diethyl ether and dried under vacuum to give Compound 59 (52 mg) as an off white solid.

1H NMR (DMSO-$d_6$) δ: 13.5 (1H, br s), 7.75-7.65 (2H, m), 7.50-7.40 (3H, m), 2.68 (2H, q), 1.15 (3H, t)

LCMS (Method 24) Rt 3.07 min; m/z (M+H)+ 313

Intermediate 51

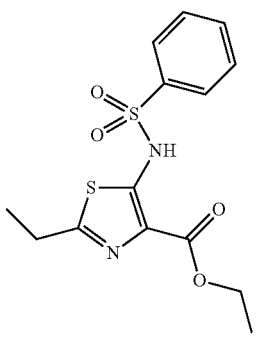 [SMILES: CCOC(=O)c1nc(CC)sc1NS(=O)(=O)c1ccccc1]

5-Amino-2-ethyl-thiazole-4-carboxylic acid ethyl ester (150 mg, 0.749 mmol) was dissolved in dichloromethane (4 mL). To this, pyridine (177 mg, 2.25 mmol) was added at room temperature. To this, benzenesulfonyl chloride (0.115 mL, 0.898 mmol) was added at room temperature and stirred for 16 hours. The mixture was concentrated in vacuo and extracted with ethyl acetate. The organic layer was washed with water, 1N hydrochloric acid solution, dried with Na$_2$SO$_4$, filtered and concentrated in vacuo to dryness. The residue was purified by chromatography on silica eluting with 0-13% ethyl acetate/petroleum ether. The fractions containing the desired product were combined and the solvents removed by evaporation in vacuo to give Intermediate 51 (120 mg) as a brown solid.

LCMS (Method 19) Rt 1.73 min; m/z (M+H)+ 341

The following compounds were prepared using a similar method as described in Example 24.

| No | Structure | LCMS Method | Rt (min) | Mass [M − H]− |
|----|-----------|-------------|----------|---------------|
| 57 | 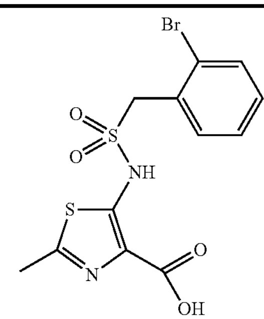 | Method 19 | 1.36 | 391/393 |

Example 25: Compound 26

Intermediate 52 (85 mg, 0.19 mmol) was dissolved in tetrahydrofuran (3 mL) and water (1 mL). To this, lithium hydroxide monohydrate (48 mg, 1.144 mmol) was added at room temperature and stirred for 48 hours. The mixture was concentrated in vacuo and diluted with water. The mixture was acidified with 1N hydrochloric acid solution. The product was collected by filtration, washed with n-pentane and dried under vacuum to give Compound 26 (57 mg).

1H NMR (DMSO-$d_6$) δ: 9.90 (1H, s), 8.34 (1H, s), 7.95-7.88 (2H, m), 7.67-7.50 (4H, m), 7.40-7.30 (2H, m), 7.20-7.10 (1H, m), 4.78 (2H, s)

LCMS (Method 34) Rt 2.52 min; m/z (M−H)⁻ 416

Intermediate 52

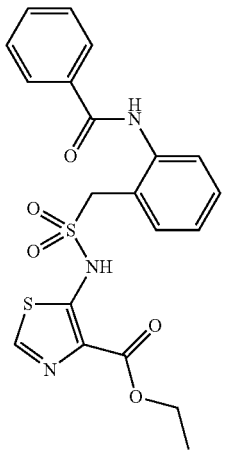 [SMILES: CCOC(=O)c1ncsc1NS(=O)(=O)Cc1ccccc1NC(=O)c1ccccc1]

Sodium hydride (60% disp. in oil; 35 mg, 0.877 mmol) was suspended in dry tetrahydrofuran (20 mL) under nitrogen. To this, Intermediate 53 (200 mg, 0.585 mmol) was added at 0° C. and the mixture was stirred for 15 minutes. To this, benzoyl chloride (82 mg, 0.585 mmol) was added at 0° C. and the mixture stirred at room temperature for 4 hours. Water was added to the reaction mixture at 0° C. and the mixture concentrated in vacuo. The mixture was extracted with ethyl acetate, dried with $Na_2SO_4$, filtered and concentrated in vacuo to dryness. The residue was purified by preparative TLC eluting with 50% ethyl acetate/petroleum ether to give Intermediate 52 (90 mg).

LCMS (Method 33) Rt 1.74 min; m/z (M+H)⁺ 446

Intermediate 53

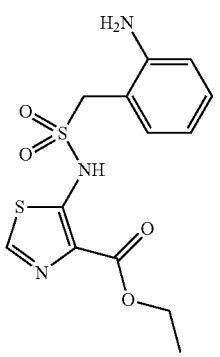 [SMILES: CCOC(=O)c1ncsc1NS(=O)(=O)Cc1ccccc1N]

5-Amino-thiazole-4-carboxylic acid ethyl ester (400 mg, 2.325 mmol) was dissolved in dichloromethane (5 mL). To this, pyridine (0.74 mL) was added at room temperature. To this, (2-nitrophenyl)methanesulfonyl chloride (0.115 mL, 0.898 mmol) was added at room temperature and stirred for 16 hours. The mixture was concentrated in vacuo, diluted with water and extracted with ethyl acetate. The organic layer was dried with $Na_2SO_4$, filtered and concentrated in vacuo to dryness and triturated with n-pentane. The solid was dissolved in ethanol (15 mL) and tetrahydrofuran (15 mL). To this, Pd (10% on carbon, 250 mg) was added at 0° C. The mixture was stirred at room temperature under a hydrogen atmosphere for 4 hours. The reaction mixture was filtered and concentrated in vacuo to dryness. The residue was triturated with n-pentane to give Intermediate 53 (600 mg) as a white solid.

LCMS (Method 33) Rt 1.41 min; m/z (M+H)⁺ 342

In the table below, Compound 25 was prepared using a similar method as described in Example 25. Compound 24 was prepared by hydrolysis of Intermediate 53 using the same method described to obtain Compound 26 from Intermediate 52. Compound 17 was obtained by hydrolysis of the nitro intermediate involved in the preparation of Intermediate 53.

| No | Structure | LCMS Method | Rt (min) | Mass [M − H]− |
|----|-----------|-------------|----------|---------------|
| 17 | *—⟨benzene⟩—NO₂ | Method 17 | 1.26 | 344 |
| 24 | *—⟨benzene⟩—NH₂ | Method 19 | 0.92 | 314 |
| 25 | *—⟨benzene⟩—NHC(O)CH₃ | Method 18 | 1.65 | 356 |

Example 26: Compound 28

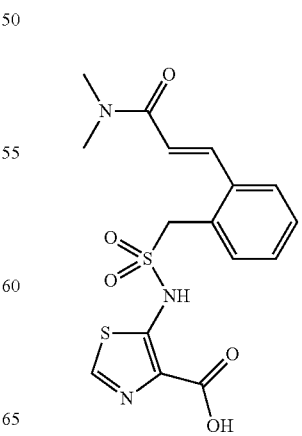

Intermediate 54 (70 mg, 0.165 mmol) was dissolved in tetrahydrofuran (3 mL) and water (1.5 mL). To this, lithium hydroxide monohydrate (42 mg, 0.992 mmol) was added at room temperature and stirred for 48 hours. The mixture was concentrated in vacuo, diluted with water and washed with diethyl ether. The aqueous layer was acidified with 1N hydrochloric acid solution. The product was collected by filtration, washed with n-pentane and dried under vacuum to give Compound 28 (40 mg) as a brown solid.

1H NMR (DMSO-$d_6$) δ: 8.40 (1H, s), 7.80-7.70 (2H, m), 7.40-7.25 (3H, m), 6.98 (1H, d), 4.85 (2H, s), 3.10 (3H, s), 2.85 (3H, s)

LCMS (Method 18) Rt 2.38 min; m/z (M+H)$^+$ 396

Intermediate 54

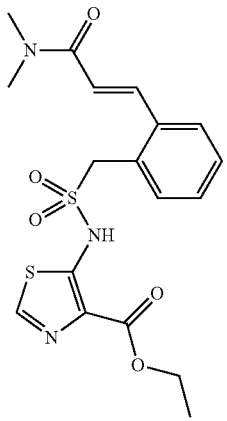 [SMILES: CCOC(=O)c1ncsc1NS(=O)(=O)Cc1ccccc1/C=C/C(=O)N(C)C]

Intermediate 55 (150 mg, 0.37 mmol) was dissolved in DMF (2 mL). To this, N,N-dimethyl acrylamide (44 mg, 0.444 mmol), Pd(OAc)$_2$ (4 mg, 0.018 mmol) and potassium tert-butoxide (62 mg, 0.555 mmol) were added at room temperature. The mixture was heated at 100° C. for 16 hours. The mixture was filtered and the filtrate concentrated in vacuo to dryness. The residue was purified by preparative TLC eluting with 5% methanol/dichloromethane to give Intermediate 54 (72 mg).

LCMS (Method 33) Rt 1.45 min; m/z (M+H)$^+$ 424

Intermediate 55

5-Amino-thiazole-4-carboxylic acid ethyl ester (400 mg, 2.325 mmol) was dissolved in dichloromethane (6 mL). To this, pyridine (551 mg, 6.976 mmol) was added at room temperature. To this, (2-bromophenyl)methanesulfonyl chloride (0.115 mL, 0.898 mmol) was added at room temperature and stirred for 16 hours. The mixture was concentrated in vacuo and extracted with ethyl acetate. The organic layer was washed with water, dried with Na$_2$SO$_4$, filtered and concentrated in vacuo to give Intermediate 55 (582 mg) as a yellow solid.

LCMS (Method 19) Rt 1.77 min; m/z (M+H)$^+$ 405/407

The following compounds were prepared using a similar method as described in Example 26.

| No | Structure | LCMS Method | Rt (min) | Mass [M − H]− |
|----|-----------|-------------|----------|---------------|
| 27 | 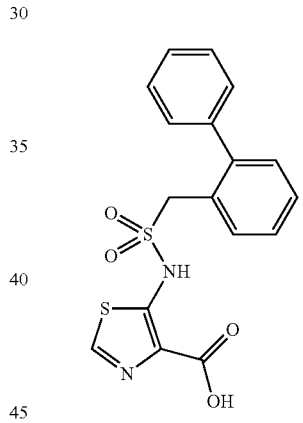 | Method 35 | 3.2 | 399 |

Example 27: Compound 29

Intermediate 55 (150 mg, 0.37 mmol) was dissolved in 1,4-dioxan (7 mL). To this, phenylboronic acid (54 mg, 0.444 mmol), PdCl$_2$(dcpf) (14 mg, 0.018 mmol) and potassium phosphate tribasic (236 mg, 1.111 mmol) were added at room temperature. The mixture was heated at 80° C. under argon for 16 hours. The mixture was concentrated in vacuo and extracted with ethyl acetate. The organic layer was washed with water, dried with Na$_2$SO$_4$, filtered and the filtrate concentrated in vacuo to dryness. The residue (140 mg, 0.348 mmol) was dissolved in tetrahydrofuran (2 mL). To this, sodium hydroxide (1N; 2 mL) was added at room temperature and stirred at 40° C. for 48 hours. The mixture was concentrated in vacuo and acidified with 1N hydrochloric acid solution. The mixture was concentrated in vacuo to dryness. The residue was purified by reverse phase HPLC. The fractions containing the desired product were combined and lyophilised to give Compound 29 (20 mg) as a pale brown solid.

1H NMR (DMSO-$d_6$) δ: 7.95 (1H, s), 7.55-7.50 (1H, m), 7.40-7.25 (7H, m), 7.20-7.15 (1H, m), 4.15 (2H, s)

LCMS (Method 29) Rt 2.72 min; m/z (M−H)$^−$ 373.

Example 28: Compound 131

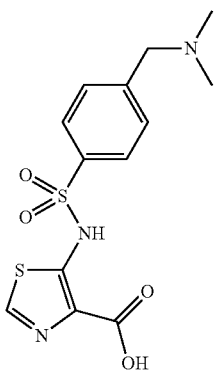 [SMILES: CN(C)Cc1ccc(S(=O)(=O)Nc2scnc2C(=O)O)cc1]

5-Amino-thiazole-4-carboxylic acid ethyl ester (200 mg, 0.909 mmol) and 4-[(dimethylamino)methyl]benzene-1-sulfonamide (195 mg, 0.909) were dissolved in acetonitrile (5 mL). To this, copper (I) iodide (8.6 mg, 0.0454 mmol), N,N'-dimethylethylenediamine (40 mg, 0.454 mmol) and potassium carbonate (377 mg, 2.727 mmol) were added at room temperature under nitrogen. The mixture was heated at 90° C. for 16 hours. The mixture was filtered and the filtrate concentrated in vacuo. The residue was diluted with water and extracted with 10% methanol/dichloromethane. The organic layer was dried with $Na_2SO_4$, filtered and concentrated in vacuo. The residue was purified by preparative TLC eluting with 100% ethyl acetate and concentrated in vacuo. The residue (60 mg, 0.162 mmol) was dissolved in tetrahydrofuran (1.5 mL) and water (0.5 mL). To this, lithium hydroxide monohydrate (21 mg, 0.468 mmol) was added at room temperature and stirred for 16 hours. The mixture was concentrated in vacuo, diluted with water and washed with 10% methanol/dichloromethane. The aqueous layer was acidified with 1N hydrochloric acid solution. The product was collected by filtration and dried under vacuum to give Compound 131 (7 mg) as a brown solid.

1H NMR (DMSO-$d_6$)
LCMS (Method 11) Rt 2.40 min; m/z (M−H)⁻ 340

Example 29: Compound 180

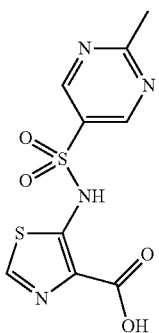 [SMILES: Cc1ncc(S(=O)(=O)Nc2scnc2C(=O)O)cn1]

Intermediate 56 (90 mg, 0.258 mmol) was dissolved in tetrahydrofuran (2 mL) and water (0.2 mL). To this, trimethylboroxine (162 mg, 1.293 mmol), Pd(dppf)Cl₂.DCM (31 mg, 0.039 mmol) and cesium carbonate (421 mg, 1.293 mmol) were added at room temperature. The mixture was heated at 85° C. under argon for 16 hours. The mixture was filtered and the filtrate concentrated in vacuo. The residue was purified by preparative TLC eluting with 70% ethyl acetate/petroleum ether to give an off white solid. The solid (30 mg, 0.091 mmol) was dissolved in tetrahydrofuran (1.5 mL) and water (0.5 mL). To this, lithium hydroxide monohydrate (31 mg, 0.73 mmol) was added at room temperature and stirred for 48 hours. The mixture was concentrated in vacuo, diluted with water and washed with diethyl ether. The aqueous layer was acidified with 1N hydrochloric acid solution. The product was collected by filtration, washed with diethyl ether and dried under vacuum to give Compound 180×13 (10 mg) as an off white solid.

1H NMR (DMSO-$d_6$) δ: 8.99 (2H, s), 7.98 (1H, s), 2.61 (3H, s)

LCMS (Method 13) Rt 1.28 min; m/z (M−H)⁻ 299

Intermediate 56

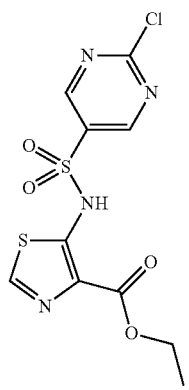 [SMILES: CCOC(=O)c1ncsc1NS(=O)(=O)c1cnc(Cl)nc1]

5-Amino-thiazole-4-carboxylic acid ethyl ester (600 mg, 3.484 mmol) was dissolved in acetone (20 mL). To this, 2-chloro-pyrimidine-5-sulfonyl chloride (890 mg, 4.181 mmol) was added at 0° C. under argon and stirred for 10 minutes. To this, sodium hydroxide solution (5N; 0.4 mL) was added drop wise at 0° C. and stirred for 1 hour; this addition was repeated 3 times. The mixture was concentrated in vacuo. The residue was purified by preparative TLC eluting with 100% ethyl acetate to give Intermediate 56 (156 mg) as a yellow solid.

LCMS (Method 13) Rt 1.70 min; m/z (M+H)⁺ 349

The following compounds were prepared using a similar method as described in Example 29.

| No | Structure | LCMS Method | Rt (min) | Mass [M − H]− |
|---|---|---|---|---|
| 166 | 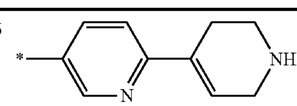 | Method 1 | 1.89 | 365 |
| 181 | 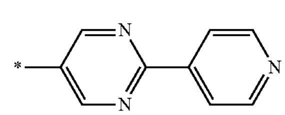 [SMILES: *c1cnc(-c2ccncc2)nc1] | Method 13 | 1.31 | 364 |

Example 30: Compound 179

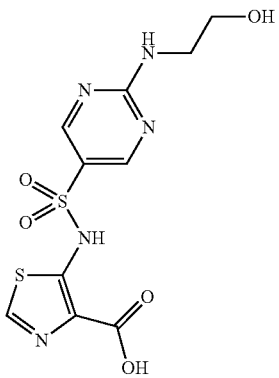 [SMILES: O=C(O)c1ncsc1NS(=O)(=O)c1cnc(NCCO)nc1]

Intermediate 57 (80 mg, 0.214 mmol) was dissolved in tetrahydrofuran (1.5 mL) and water (0.5 mL). To this, lithium hydroxide monohydrate (71 mg, 1.713 mmol) was added at room temperature and stirred for 20 hours. The mixture was concentrated in vacuo, diluted with water and washed with n-pentane. The aqueous layer was acidified with 1N hydrochloric acid solution. The product was collected by filtration, washed with n-pentane and diethyl ether and dried under vacuum to give Compound 179×12 (40 mg) as an off white solid.

1H NMR (DMSO-$d_6$) δ: 8.65-8.45 (3H, m), 8.15 (1H, t), 3.55-3.45 (2H, m), 3.40-3.30 (2H, m)

LCMS (Method 13) Rt 1.51 min; m/z (M+H)$^+$ 346

Intermediate 57

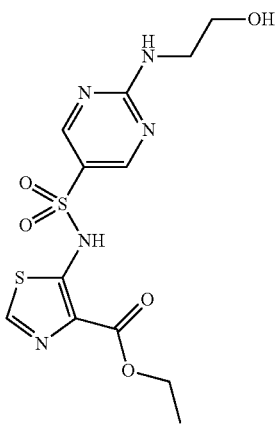 [SMILES: CCOC(=O)c1ncsc1NS(=O)(=O)c1cnc(NCCO)nc1]

Intermediate 56 (100 mg, 0.287 mmol) was dissolved in acetonitrile (5 mL) under argon. To this, ethanolamine (0.17 mL, 0.287 mmol) was added at room temperature and stirred at 50° C. for 2 hours. The mixture was diluted with water and extracted with ethyl acetate. The organic layer was dried with Na$_2$SO$_4$, filtered and concentrated in vacuo. The residue was purified by preparative TLC eluting with 100% ethyl acetate to give Intermediate 57 (90 mg) as a yellow solid.

LCMS (Method 13) Rt 1.85 min; m/z (M+H)$^+$ 374

Example 31: Compound 143

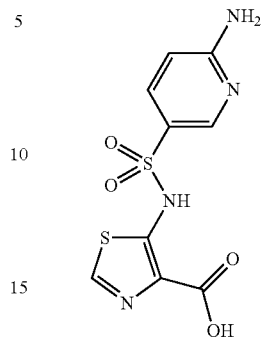

Intermediate 58 (90 mg, 0.274 mmol) was dissolved in tetrahydrofuran (3 mL) and water (1 mL). To this, lithium hydroxide monohydrate (69 mg, 1.645 mmol) was added at room temperature and stirred for 48 hours. The mixture was concentrated in vacuo, diluted with water and washed with diethyl ether. The aqueous layer was acidified with 1N hydrochloric acid solution. The product was collected by filtration, washed with diethyl ether and dried under vacuum to give Compound 143 (30 mg) as an off white solid.

1H NMR (DMSO-$d_6$) δ: 8.40 (1H, s), 7.80-7.70 (2H, m), 7.40-7.25 (3H, m), 6.98 (1H, d), 4.85 (2H, s), 3.10 (3H, s), 2.85 (3H, s)

LCMS (Method 12) Rt 4.57 min; m/z (M+H)$^+$ 301

Intermediate 58

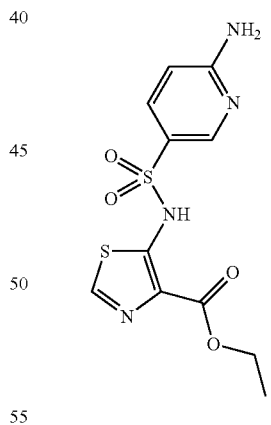

5-Amino-thiazole-4-carboxylic acid ethyl ester (200 mg, 1.161 mmol) was dissolved in acetone (8 mL). To this, 6-aminopyridine-3-sulfonyl chloride (268 mg, 1.393 mmol) was added at 0° C. under argon and stirred for 10 minutes. To this, sodium hydroxide solution (5N; 0.4 mL) was added drop wise at 0° C. and stirred for 1 hour; this addition was repeated 2 times. The mixture was concentrated in vacuo. The residue was purified by preparative TLC eluting with 100% ethyl acetate to give Intermediate 58 (90 mg) as a yellow solid.

LCMS (Method 13) Rt 1.52 min; m/z (M+H)$^+$ 329

Example 32: Compound 119

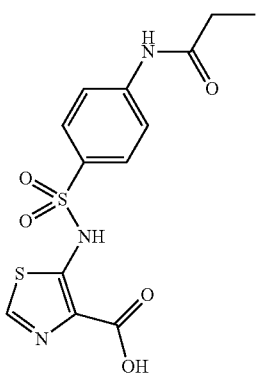 [SMILES: CCC(=O)Nc1ccc(S(=O)(=O)Nc2scnc2C(=O)O)cc1]

Intermediate 59 (90 mg, 0.234 mmol) was dissolved in tetrahydrofuran (3 mL) and water (1 mL). To this, lithium hydroxide monohydrate (39 mg, 0.936 mmol) was added at room temperature and stirred for 36 hours. The mixture was concentrated in vacuo, diluted with water and washed with ethyl acetate. The aqueous layer was acidified with 1N hydrochloric acid solution. The product was collected by filtration, washed with diethyl ether and dried under vacuum to give Compound 226 (40 mg) as a brown solid.

1H NMR (DMSO-$d_6$) δ: 8.40 (1H, s), 7.80-7.70 (2H, m), 7.40-7.25 (3H, m), 6.98 (1H, d), 4.85 (2H, s), 3.10 (3H, s), 2.85 (3H, s)

LCMS (Method 36) Rt 4.54 min; m/z (M+H)$^+$ 356

Intermediate 59

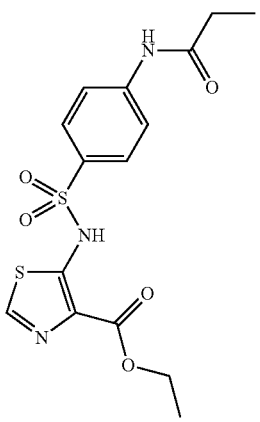 [SMILES: CCOC(=O)c1ncsc1NS(=O)(=O)c1ccc(NC(=O)CC)cc1]

Intermediate 60 (100 mg, 0.305 mmol) and triethylamine (0.125 mL, 0.915 mmol) were dissolved in dichloro-methane (4 mL). To this, propionyl chloride (23 mg, 0.244 mmol) was added drop wise at 0° C. and stirred for 1 hour. The mixture was poured onto ice/water and extracted with 10% methanol/dichloromethane. The organic layer was dried with Na$_2$SO$_4$, filtered and concentrated in vacuo. The residue was washed with 4N hydrochloric acid solution, collected by filtration and dried under vacuum to give Intermediate 59 (90 mg) as a brown solid.

LCMS (Method 10) Rt 3.13 min; m/z (M+H)$^+$ 384

Intermediate 60

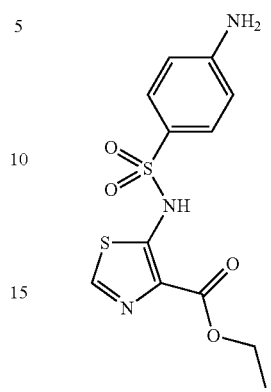

Intermediate 61 (3.3 g, 9.235 mmol) was dissolved in ethanol (40 mL), tetrahydrofuran (40 mL) and water (10 mL) under argon. To this, iron powder (2.5 g, 46.18 mmol) and ammonium chloride (1.26 g, 23.09 mmol) was added at room temperature and heated at 80° C. for 1 hour. The mixture was filtered hot and the residue washed with 10% methanol/dichloromethane. The filtrate was washed with water, dried with Na$_2$SO$_4$, filtered and concentrated in vacuo to give Intermediate 60 (2.2 g).

LCMS (Method 19) Rt 1.46 min; m/z (M+H)$^+$ 328

Intermediate 61

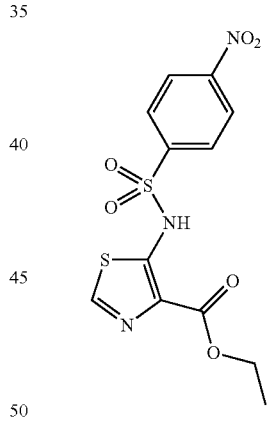

Sodium hydride (60% disp. in oil; 2.79 g, 69.68 mmol) was suspended in dry tetrahydrofuran (60 mL). To this, 5-amino-thiazole-4-carboxylic acid ethyl ester (4 g, 23.23 mmol) was added at 0° C. and the mixture was stirred for 10 minutes. To this, 4-nitrobenzenesulfonyl chloride (6.2 g, 27.87 mmol) was added at 0° C. and the mixture stirred at room temperature for 2 hours. The mixture was diluted with ammonium chloride solution and diethyl ether. The solid formed collected by filtration, washed with ether and dried under vacuum to give Intermediate 61 (3.2 g) as a yellow solid.

LCMS (Method 37) Rt 1.56 min; m/z (M−H)$^-$ 356

The following compounds were prepared using a similar method as described in Example 32. In the table below Compound 125 was prepared using a similar method as described in Example 32.

Compound 36 was prepared by hydrolysis of Intermediate 60 using the same method used to prepare Example 119 from Intermediate 59.

Compounds 120 and 176 were prepared using acetoxyacetylchloride and 2-acetoxyisobutyryl chloride respectively, in place of propionyl chloride used to prepare Example 32.

Compound 174 was prepared by using Boc-glycine in place of the propionyl chloride used to prepare Example 32. A TFA deprotection was required prior to final purification.

Compound 121 was prepared by reacting Intermediate 60 with methylisocyanate followed by hydrolysis as foe Example 32.

| No | Structure | Mass | LCMS Method | Rt (min) | Mass [M−H]− |
|---|---|---|---|---|---|
| 36 | 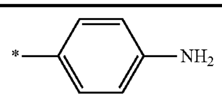 | | | | 299 |
| 120 | 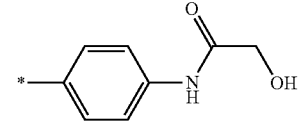 [SMILES: *c1ccc(NC(=O)CO)cc1] | | | | 357 |
| 125 | 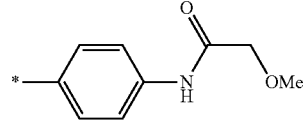 [SMILES: *c1ccc(NC(=O)COC)cc1] | | | | 371 |
| 121 | 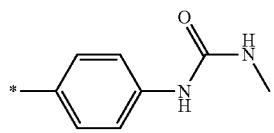 | | | | 356 |
| 174 X7 | 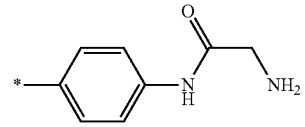 [SMILES: *c1ccc(NC(=O)CN)cc1] | | | | |
| 176 X9 | 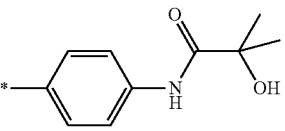 [SMILES: *c1ccc(NC(=O)C(C)(C)O)cc1] | | | | |

Example 33: In Vitro MBL Inhibition Assay

The MBL enzyme VIM-2 is produced and purified as disclosed in Borgianni et al, *Antimicrobial Agents & Chemotherapy*, (2010), 54(8), 3197-3204.

The MBL enzyme IMP-1 is produced and purified as disclosed in Laraki et al, *Antimicrobial Agents & Chemotherapy*, (1999), 43(4), 902-906.

NDM-1 is produced and purified as disclosed in Yong et al, *Antimicrobial Agents & Chemotherapy*, (2009) 53(12), 5046-54.

Reaction buffers were prepared in a UV-transparent 96-well microplate, which buffer contains 10 mM HEPES pH 7.5, 50 μM ZnSO$_4$, 20 μg/mL BSA. An amount of 75 ng of protein was added to each well.

Spectrophometric assays are performed to determine NDM-1/VIM-2/IMP-1 carbapenemase activity using purified proteins (50 ng for NDM-1/VIM-2, 25 ng IMP-1) from NDM-1/VIM-2/IMP-1 expressing bacteria using 300 μm of imipenem as substrate in 10 mM HEPES pH 7.5, 50 μM ZnSO$_4$. MBL hydrolysis is measured at 299 nm for 10 minutes at 30° C. as the absorbance changes due to the opening of beta-lactam ring of the antibiotic. The assays are performed with ethylenediaminetetraacetic acid (EDTA; 25 mM) as control to examine the complete inhibition of carbapenemase activity. A range of inhibitor concentrations are routinely assessed: from 0.1 to 50 μM (2-fold dilutions series) for NDM-1, VIM-2 and IMP-1 assays, delivering IC$_{50}$ values to calculate Ki values for the inhibition of each enzyme, using the standard Cheng-Prusoff equation, Ki=IC$_{50}$/(1+([S]/Km)) and where the Km values for NDM-1, VIM-2 and IMP-1 are 70 μM, 9 μM and 25 μM respectively.

The Ki values obtained for selected example compounds are shown in Table 3, where they are compared with the values for pyridine-2-carboxylic acid.

TABLE 3

| Compound | NDM-1 μM | VIM-2 μM | IMP-1 μM |
|---|---|---|---|
| Pyridine-2-carboxylic acid | 3.0 | 1.0 | 300 |
| 63 | 0.6 | 0.13 | 1.7 |
| 81 | 0.13 | 0.03 | 0.41 |
| 151 | 3.2 | 0.1 | 1.8 |
| 78 | 0.16 | 0.4 | 0.05 |
| 163 | 0.37 | 0.28 | 1.0 |
| 138 | 0.43 | 0.01 | 0.13 |
| 111 | 2.8 | 0.22 | 0.9 |
| 75 | 2.1 | 0.34 | 0.94 |
| 77 | 1.3 | 0.03 | 0.12 |
| 88 | 1.0 | 0.16 | 0.58 |
| 96 | 2.7 | 0.35 | 1.2 |
| 1 | 1.2 | 0.32 | 0.08 |
| 5 | 2.5 | 0.21 | 0.05 |
| 7 | 0.75 | 0.08 | 0.03 |
| 20 | 0.94 | 0.48 | 0.1 |
| 41 | 0.67 | 0.22 | 0.08 |
| 60 | 0.8 | 0.1 | 0.07 |
| 50 | 1.7 | 0.26 | 0.06 |
| 58 | 2.3 | 0.8 | 0.07 |
| 170 X3 | 4.2 | 0.46 | |
| 172 X5 | 0.22 | 0.05 | 0.76 |
| 173 X6 | 0.18 | 0.04 | 0.33 |

Example 34: Antibiotic Activity of Meropenem on MBL Expressing Bacteria in the Presence of the Compounds of the Invention The minimal inhibitory concentration (MIC) of meropenem in presence of the inhibitor is routinely assessed against 3 representative clinical strains:
  NTBC020 Strain: *Escherichia coli* producing NDM-1+TEM-1+CTX-M-15, (isolated in Australia in 2009);
  NTBC023 strain: *Klebsiella pneumoniae* producing VIM-1+SHV-5, (isolated in France in 2002);
  NTBC062 strain: *Klebsiella pneumoniae* producing IMP-1+TEM-1, (isolated in France in 2012);

The assay was performed according to the standard broth microdilution method described by the Clinical and Laboratory Standards Institute (CLSI-M7-A7—*Methods for dilution antimicrobial susceptibility tests for bacteria that grow aerobically; Approved standard*; CLSI, Wayne, Pa., USA. 2006). This method involves the use of small volumes of broth dispensed in sterile, plastic 96-wells microdilution plates. The compounds were tested at a concentration of 100 µM and controls included the susceptibility tests for the three selected strains without the compounds and for the two reference strains E. coli ATCC 25922 and Pseudomonas aeruginosa ATCC 27853 as Quality Controls.

From a stock solution at 20 mM in DMSO, compounds were prepared by diluting 0.04 mL of the compound solution in 0.04 mL of Mueller-Hinton (MH) broth (2-fold dilution). Then, 0.001 mL of the compound dilution was distributed in the 96-wells microdilution plates to give a final concentration of 100 µM for a final volume of 0.1 mL by well.

From a meropenem stock solution at 10 mg/mL in water, meropenem 2-fold serial dilutions were prepared in MH broth at twice the desired final concentrations, e.g from 512 to 0.0037 µg/ml. The 96-wells microdilution plates were then filled with 0.05 mL of the meropenem dilutions. For each susceptibility test, two wells were left free of antibiotic and filled with 0.05 mL of sterile MH broth to serve as growth controls.

The bacterial inoculum was prepared by direct colony suspension from a 24 h-agar plate in saline solution (NaCl 9 g/L). The suspension was adjusted to a 0.5 MacFarland turbidity standard (1-2×10$^8$ CFU/mL) and then diluted 1:100 in MH broth. 0.05 mL of the bacterial dilution was then inoculated to each well giving a final volume of 0.1 mL and a final bacterial concentration of approximately 5×10$^5$ CFU/mL.

Microdilution plates were incubated at 37° C. in an ambient air incubator for 18-20 h. MICs are then reported as the lowest concentration of meropenem (in mg/mL) that completely inhibits growth of the organism.

The results are shown in Table 4.

TABLE 4

| Compound No | Strain | | |
|---|---|---|---|
| | NTBC020 | NTBC023 | NTBC039 |
| 66 | 16 | 8 | 8 |
| 69 | 16 | 4 | 1 |
| 101 | 32 | 8 | 1 |
| 67 | 1 | 16 | 8 |
| 104 | 16 | 4 | 2 |
| 94 | 16 | 8 | 4 |
| 124 | 4 | 4 | 0.25 |
| 144 | 16 | 8 | 1 |
| 118 | 4 | 8 | 4 |
| 163 | 16 | 32 | 16 |
| 138 | 32 | 16 | 1 |
| 111 | 4 | 8 | 0.25 |
| 147 | 8 | 16 | 4 |
| 1 | 32 | 64 | 16 |
| 41 | 64 | 16 | 4 |
| 48 | 4 | 2 | 0.25 |
| 170 | 16 | 1 | 0.25 |
| 172 | 64 | 8 | 8 |
| 173 | 128 | 8 | 8 |

Example 35: Kit for Detecting Bacteria Expressing a MBL Enzyme

A kit according to the invention comprises:
a bacterial lysis buffer, for example Tris-HCl 20 mmol/L lysis buffer,
a carbapenemase activity detection solution, for example a solution made of 3 mg of imipenem monohydrate, pH 7.8, phenol red solution, and 0.1 mmol/L ZnSO$_4$. The phenol red solution has been prepared by mixing 2 mL of a phenol red solution 0.5% (wt/vol) with 16.6 mL of distilled water. The pH value has then been adjusted to 7.8 by adding drops of 1 N NaOH,
a compound of the invention, or a plurality of compounds of the invention,
and instructions of use.

The instructions of use are as follows.

One calibrated amount of the tested bacterial strain is resuspended in the bacterial lysis buffer, vortexed for 1 minute and further incubated at room temperature for 30 minutes. This bacterial suspension is centrifuged at 10,000×g at room temperature for 5 minutes. 30 µL of the supernatant, corresponding to the cell-free enzymatic suspension, are mixed in 96-well trays with 100 µL of the carbapenemase activity detection solution. In some of the wells the compound of the invention is added at a fixed concentration, preferably between 10 nM and 10 µM. The trays are incubated at 37° C. for a maximum of 2 hours. The colour of the solution in each well is assessed visually or using a spectrophotometer at the appropriate wavelength.

The detection technique is based on the variation of the pH of the solution due to hydrolysis of the β-lactam ring of imipenem by MBL enzymes. The colour of the detection solution turns from red to orange or yellow for tested strains that produce MBL enzymes. When a compound of the invention is added to the reaction solution, change of colour or absence of change indicates the presence or absence of MBL enzymes.

The invention claimed is:

1. A compound of formula (I) including all polymorphs thereof:

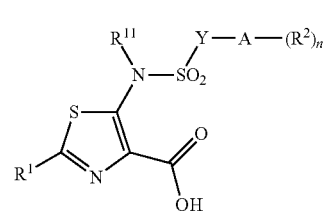

(I)

wherein
R$^1$ is hydrogen;
Y is a single bond, —C$_{1-4}$ alkylene- or —C$_{2-4}$ alkenylene-, either of which may be substituted with a group R$^{17}$; or
—C$_{1-4}$ alkylene-O—; —C$_{1-4}$ alkylene-N(R$^8$)—; —N(R$^8$)—; —C$_{1-4}$ alkylene-C(O)N(R$^8$)—; —C$_{1-4}$ alkylene-N(R$^8$)C(O)— or —N(R$^8$)C$_{1-4}$ alkylene-;
wherein R$^{17}$ is selected from OR$^l$, NR$^l$R$^m$, NR$^l$C(O)R$^m$, C(O)NR$^l$R$^m$, and C(O)OR$^m$;
each R$^l$ and R$^m$ is independently H or C$_{1-4}$ alkyl;
and R$^8$ is hydrogen or C$_{1-6}$ alkyl or —C(O)C$_{1-6}$ alkyl either of which is optionally substituted by one or more substituent R$^d$; and
C$_{1-4}$ alkylene chains may optionally be substituted with one or more substituents R$^e$;
each R$^d$ and R$^e$ is independently halo, CN, OH or OC$_{1-4}$ alkyl optionally substituted by one or more substituents selected from halo or OH;
A represents a cyclic group selected from a 6- to 10-membered aryl, 5- to 10-membered heteroaryl or a 3- to 10-membered carbocyclyl or heterocyclyl group;
n is 0 to 4;
each R$^2$ is independently selected from R$^3$; or C$_{1-4}$ alkyl, C$_{2-4}$ alkenyl, O(C$_{1-4}$ alkyl), S(C$_{1-4}$ alkyl), SO(C$_{1-4}$ alkyl) or SO$_2$(C$_{1-4}$ alkyl), any of which may optionally be substituted with one or more substituent R$^3$; or C(O)OR$^6$; C(O)R$^6$; OR$^5$, NR$^4$R$^5$; NR$^4$C(O)R$^6$, NR$^4$C(O)NR$^5$R$^6$ or SO$_2$NR$^{21}$R$^{22}$;

or when A is saturated or partially saturated, R$^2$ may also be oxo;

each R$^3$ is independently halo, nitro, CN, OH; or —C(O)OR$^{14}$, —C(O)NR$^{14}$R$^{15}$ or —NR$^{14}$R$^{15}$; or phenyl optionally substituted with one or more substituent R$^7$; or naphthyl optionally substituted with one or more substituent R$^7$; or 5- to 10-membered heteroaryl optionally substituted with one or more substituent R$^7$; or 3- to 8-membered carbocyclyl optionally substituted with one or more substituent R$^7$; or 3- to 8-membered heterocyclyl optionally substituted with one or more substituents selected from oxo or R$^7$;

each of R$^{14}$ and R$^{15}$ is independently H, or C$_{1-6}$ alkyl optionally substituted with one or more substituents selected from halo or OH;

each R$^7$ is independently halo, CN, OH; or C$_{1-4}$ alkyl or OC$_{1-4}$ alkyl either of which may optionally substituted by one or more substituents selected from halo or OH; or NR$^j$R$^k$, wherein each R$^j$ and R$^k$ is independently H or C$_{1-4}$ alkyl;

each of R$^{21}$ and R$^{22}$ is hydrogen or C$_{1-4}$ alkyl or R$^{21}$ and R$^{22}$ together with the nitrogen atom to which they are attached may form a 5- or 6-membered heterocyclic ring, optionally containing one further heteroatom selected from N, O or S and optionally substituted with C$_{1-4}$ alkyl or halo;

R$^4$ is hydrogen or C$_{1-6}$ alkyl optionally substituted with halo, CN, OH, NR$^j$R$^k$; or OC$_{1-4}$ alkyl which may optionally substituted by one or more substituent selected from halo or OH;

wherein each R$^j$ and R$^k$ is independently H or C$_{1-4}$ alkyl;

R$^5$ is hydrogen, phenyl, 5- to 6-membered heteroaryl, 3- to 8-membered carbocyclyl or 3 to 8-membered heterocyclyl; or C$_{1-6}$ alkyl optionally substituted with phenyl, 5- to 6-membered heteroaryl, 3- to 8-membered carbocyclyl or 3- to 8-membered heterocyclyl;

wherein phenyl and heteroaryl groups are optionally substituted by one or more substituent R$^f$ and carbocyclyl and heterocyclyl groups are optionally substituted by one or more substituent R$^g$ and wherein:

each R$^f$ is independently halo, CN, OH or C$_{1-4}$ alkyl or OC$_{1-4}$ alkyl either of which may optionally be substituted by one or more substituents selected from halo or OH;

each R$^g$ is independently halo, CN, OH, oxo or C$_{1-4}$ alkyl or OC$_{1-4}$ alkyl optionally substituted by one or more substituents selected from halo or OH;

R$^6$ is C$_{1-6}$ alkyl optionally substituted with one or more R$^h$, or phenyl or 5- to 6-membered heteroaryl either of which is optionally substituted with one or more substituent R$^i$;

each R$^h$ is independently halo, CN, OH, NH$_2$, phenyl, pyridyl, COOH or OC$_{1-4}$ alkyl optionally substituted by one or more substituents selected from halo or OH;

each R$^i$ is independently halo, CN, OH, NH$_2$ or C$_{1-4}$ alkyl or OC$_{1-4}$ alkyl either of which may optionally be substituted by one or more substituents selected from halo or OH;

R$^{11}$ is hydrogen, C$_{1-4}$ alkyl optionally substituted by halo or benzyl optionally substituted by halo;

or a salt thereof;

provided that the compound is not 5-(4-aminophenylsulfonamido)thiazole-4-carboxylic acid.

2. The compound according to claim 1 wherein R$^{11}$ is hydrogen.

3. The compound according to claim 1 wherein Y is a single bond, —C$_{1-4}$ alkylene, —C$_{1-4}$ alkylene-O—, —C$_{1-4}$ alkylene-NR$^8$—, —NR$^8$— or —NR$^8$(C$_{1-4}$ alkylene)-; wherein R$^8$ is hydrogen or methyl, but especially hydrogen and wherein alkylene chains are optionally substituted with one or more substituents R$^e$ as defined in claim 1.

4. The compound according to claim 3 wherein R$^e$ is halo.

5. The compound according to claim 3 wherein Y is a single bond, —CH$_2$—, —(CH$_2$)$_2$—, —(CH$_2$)$_3$—, —C(CH$_3$)—, —CH(CH$_2$CH$_3$)—, —NH—, —N(CH$_3$)—, —NHCH$_2$— or —N(CH$_3$)CH$_2$—.

6. The compound according to claim 1 wherein A represents 6- to 10-membered aryl, 3- to 8-membered cycloalkyl, 5- to 10-membered heteroaryl or 3- to 8-membered heterocyclyl, any of which may be unsubstituted or substituted with one to four R$^2$ groups as defined in claim 1.

7. The compound according to claim 1 wherein A is selected from phenyl, pyridyl, pyrazole, thiophenyl, benzothiophenyl, quinolinyl or isoquinolinyl, any of which may be unsubstituted or substituted with one to four R$^2$ groups as defined in claim 1; or a 5- or 6-membered carbocyclic or heterocyclic ring which may be unsubstituted or substituted with one to four R$^2$ groups as defined in claim 1, for example by one or two oxo groups; or a 9- to 10-membered bicyclic aromatic ring which may be unsubstituted or substituted with one to four R$^2$ groups as defined in claim 1, for example with one to four substitutents selected from halo or, when the ring is partially saturated, with oxo.

8. The compound according to claim 1 wherein A represents phenyl, pyridyl, pyrazolyl, thiophenyl or benzothiophenyl; especially phenyl, 3-pyridyl, 4-pyridyl, thiophen-2-yl, thiophen-3-yl, pyrazol-3-yl, pyrazol-4-yl, pyrazol-5-yl, benzothiophen-2-yl or benzothiophen-3-yl, any of which may be unsubstituted or substituted with one to four R$^2$ groups as defined in claim 1.

9. The compound according to claim 1 wherein n is 0 to 3.

10. The compound according to claim 1 wherein each R$^2$ is independently selected from:

halo, nitro, cyano, OH or when A is saturated or partially saturated, oxo;

C$_{1-4}$ alkyl, C$_{2-4}$ alkenyl, O(C$_{1-4}$ alkyl) any of which may optionally be substituted with one or more substituent R$^3$ as defined in claim 1; or OR$^5$, wherein R$^5$ is as defined in claim 1; or NR$^4$R$^5$, where R$^4$ and R$^5$ are as defined in claim 1; or NR$^4$C(O)R$^6$, where R$^4$ and R$^6$ are as defined in claim 1; or NR$^4$C(O)NR$^5$R$^6$, where R$^4$, R$^5$ and R$^6$ are as defined in claim 1; or C(O)R$^6$ or C(O)OR$^6$, where R$^6$ is as defined in claim 1; or SO$_2$(C$_{1-4}$ alkyl); or SO$_2$NR$^{21}$R$^{22}$, wherein each of R$^{21}$ and R$^{22}$ is hydrogen or where R$^{21}$ and R$^{22}$ together with the nitrogen atom to which they are attached form a piperidine, pyrrolidine or morpholine ring or a piperazine ring optionally substituted on the other nitrogen atom with methyl or ethyl; or a cyclic group selected from phenyl, naphthyl, 5- to 10-membered heteroaryl or 3- to 8-membered heterocyclyl, any of which is optionally substituted with one or more substituent $R^7$ as defined in claim 1.

11. The compound according to claim 10 wherein:
$R^2$ is $C_{1-4}$ alkyl, $C_{2-4}$ alkenyl, $O(C_{1-4}$ alkyl) and is unsubstituted or is substituted by an $R^3$ group selected from halo, phenyl, amino, methylamino or dimethylamino; or
$R^2$ is $OR^5$, wherein $R^5$ is a 5-membered heterocyclic group, for example pyrrolidine; or
$R^2$ is $NR^4R^5$, wherein $R^4$ is hydrogen or $C_{1-4}$ alkyl and $R^5$ is hydrogen or a 5- or 6-membered heterocyclic group such as oxazolyl, isoxazolyl and pyrrolyl and piperidinyl; or
$R^2$ is $NR^4C(O)R^6$, wherein $R^4$ is hydrogen or methyl, especially hydrogen, and $R^6$ is $C_{1-4}$ alkyl optionally substituted with one or more $R^h$, where each $R^h$ is independently, OH, $NH_2$, phenyl, or $OC_{1-4}$ alkyl; or $R^6$ is phenyl; or
$R^2$ is $NR^4C(O)NR^5R^6$, wherein $R^4$ is hydrogen or methyl, especially hydrogen; and $R^5$ is hydrogen and $R^6$ is $C_{1-4}$ alkyl, for example methyl; or
$R^2$ is $C(O)R^6$ or $C(O)OR^6$, wherein $R^6$ is $C_{1-4}$ alkyl substituted with phenyl and/or $NH_2$; or
$R^2$ is a cyclic group selected from phenyl, pyridyl, pyrazolyl, oxazolyl, isoxazolyl, pyrrolidinyl, piperidinyl, piperazinyl, morpholinyl, diazepanyl or azetidinyl, any of which may be substituted by one or more substituents $R^7$, where $R^7$ is halo, $C_{1-4}$ haloalkyl or $NH_2$; and wherein pyrazolyl, pyrrolidinyl, piperidinyl, piperazinyl, morpholinyl, diazepanyl or azetidinyl may be substituted by one or more oxo groups in addition to or instead of an $R^7$ group.

12. The compound according to claim 1 wherein:
A is phenyl or pyridyl;
n is 0 to 3; and
$R^2$ is halo, $CF_3$; nitro, methoxy, phenyl, $SO_2$—$C_{1-4}$ alkyl; or
$C_{1-2}$ alkyl or ethenyl optionally substituted with phenyl or —C(O)$NR^{14}R^{15}$, where $R^{14}$ and $R^{15}$ are each independently H or methyl; or
a 4- to 7-membered carbocyclic or heterocyclic ring optionally substituted with one or more substituents selected from oxo or $R^7$ groups, where $R^7$ is as defined in claim 1; $NHR^4$, $NHR^5$, $NHC(O)R^6$ or $NR^4C(O)NR^5R^6$ where $R^4$, $R^5$ and $R^6$ are defined in claim 1.

13. The compound according to claim 1 wherein
A is phenyl or pyridyl;
n is 0 to 3; and $R^2$ is:
halo, trifluoromethyl, nitro, methoxy, phenyl; or
oxazoline, morpholine, pyrrolidine, piperidine, tetrahydropyridine, piperazine, diazepan or aziridine any of which may optionally be substituted with an oxo group or with $NH_2$ or $C_{1-2}$ alkyl or $C_{1-4}$ haloalkyl; or
oxazole or pyrazole, either of which may optionally be substituted with methyl; or
NHC(O)$C_{1-2}$ alkyl, which may optionally be substituted by OH or methoxy: or
NHC(O)NHCH$_3$, NH$_2$, NH(CH$_3$), CH$_2$N(CH$_3$)$_2$, SO$_2$CH$_3$; or
ethenyl substituted with phenyl or C(O)N(CH$_3$)$_2$.

14. The compound according to claim 1 wherein A is phenyl optionally substituted with 1 to 3 halo substituents $R^2$.

15. The compound according to claim 14 wherein:
one of the halo substituents $R^2$ is at the 2-position; or
one of the halo substituents $R^2$ is at the 3-position; or
one of the halo substituents $R^2$ is at the 4-position.

16. The compound according to claim 1 wherein A is phenyl substituted with one halo substituent $R^2$ and with one or two further substituents $R^2$ as defined in claim 1.

17. The compound according to claim 1 wherein the phenyl group A:
(i) is substituted with two halo substituents $R^2$ at the 2- and 5-positions; or
(ii) is substituted with two halo substituents $R^2$ at the 2- and 3-positions; or
(iii) is substituted with two halo substituents $R^2$ at the 3- and 5-positions; or
(iv) is substituted with two halo substituents $R^2$ at the 3- and 4-positions; or
(v) is substituted with one or two halo substituents $R^2$ and an additional $R^2$ substituent selected from trifluoromethyl or nitro.

18. The compound according to claim 1 wherein A is phenyl substituted with at least one $R^2$ group selected from a trifluoromethyl group or an amino group.

19. The compound according to claim 18 wherein:
the trifluromethyl or amino group is at the 2-position; or
the trifluromethyl or amino group is at the 3-position; or
the trifluoromethyl or amino group is at the 4-position.

20. The compound according to claim 1 wherein A is a 3- to 6-membered carbocyclic or heterocyclic ring optionally fused to a phenyl group.

21. The compound according to claim 20 wherein, independently or in combination:
n is 0-2;
at least one $R^2$ is oxo, or when attached to a ring nitrogen atom is $C(O)OR^6$,
wherein $R^6$ is benzyl.

22. The compound according to claim 1 wherein A is pyazolyl or thiophenyl, especially pyrazol-4-yl, pyrazol-5-yl, thiophen-2-yl or thiophen-3-yl.

23. The compound according to claim 22 wherein independently or in any combination:
n is 1 to 3;
$R^2$ is halo, methyl, trifluoromethyl or phenyl or pyridyl, either of which may optionally be substituted with halo or trifluoromethyl, especially trifluoromethyl.

24. The compound according to claim 1 wherein A is quinolinyl, isoquinolinyl or benzothiophenyl especially quinolin-6-yl or benzothiophen-2-yl and n is 0.

25. The compound according to claim 1 selected from:
5-benzenesulfonamido-1,3-thiazole-4-carboxylic acid;
5-{[(3,5-dichlorophenyl)methyl]sulfonamido}-1,3-thiazole-4-carboxylic acid;
5-(2,4,6-trimethylphenylsulfonamido)thiazole-4-carboxylic acid;
5-{[3-(trifluoromethyl)phenyl]sulfonamido}-1,3-thiazole-4-carboxylic acid;
5-(phenylmethylsulfonamido)thiazole-4-carboxylic acid;
5-(3-methoxyphenylsulfonamido)thiazole-4-carboxylic acid;
5-(2-phenylethylsulfonamido)thiazole-4-carboxylic acid;
5-(thiophene-2-sulfonamido)thiazole-4-carboxylic acid;
5-(4,5-dichlorothiophene-2-sulfonamido)thiazole-4-carboxylic acid;
5-(2,5-dichlorothiophene-3-sulfonamido)thiazole-4-carboxylic acid;
5-(2-(trifluoromethyl)phenylsulfonamido)thiazole-4-carboxylic acid;

5-(4-(trifluoromethyl)phenylsulfonamido)thiazole-4-carboxylic acid;
5-(2-chloro-5-(trifluoromethyl)phenylsulfonamido)thiazole-4-carboxylic acid;
5-(3,5-bis(trifluoromethyl)phenylsulfonamido)thiazole-4-carboxylic acid;
5-({[2-(trifluoromethyl)phenyl]methyl}sulfonamido)-1,3-thiazole-4-carboxylic acid;
5-{[(2-methylphenyl)methyl]sulfonamido}-1,3-thiazole-4-carboxylic acid;
5-((2-nitrophenyl)methylsulfonamido)thiazole-4-carboxylic acid;
5-{[((2-bromophenyl)methyl]sulfonamido}-1,3-thiazole-4-carboxylic acid;
5-(5-chlorothiophene-2-sulfonamido)thiazole-4-carboxylic acid;
5-(5-phenylthiophene-2-sulfonamido)thiazole-4-carboxylic acid;
5-(thiophene-3-sulfonamido)thiazole-4-carboxylic acid;
5-(2,5-dimethylthiophene-3-sulfonamido)thiazole-4-carboxylic acid;
5-([1,1'-biphenyl]-2-ylsulfonamido)thiazole-4-carboxylic acid;
5-((2-aminophenyl)methylsulfonamido)thiazole-4-carboxylic acid;
5-((2-acetamidophenyl)methylsulfonamido)thiazole-4-carboxylic acid;
5-((2-benzamidophenyl)methylsulfonamido)thiazole-4-carboxylic acid;
(E)-5-((2-styrylphenyl)methylsulfonamido)thiazole-4-carboxylic acid;
(E)-5-((2-(3-(dimethylamino)-3-oxoprop-1-en-1-yl)phenyl)methylsulfonamido)thiazole-4-carboxylic acid;
5-([1,1'-biphenyl]-2-ylmethylsulfonamido)thiazole-4-carboxylic acid;
5-((2-(trifluoromethoxy)phenyl)methylsulfonamido)thiazole-4-carboxylic acid;
5-((3-(trifluoromethyl)phenyl)methylsulfonamido)thiazole-4-carboxylic acid;
5-((3-bromophenyl)methylsulfonamido)thiazole-4-carboxylic acid;
5-((3-cyanophenyl)methylsulfonamido)thiazole-4-carboxylic acid;
5-((2-chlorophenyl)methylsulfonamido)thiazole-4-carboxylic acid;
5-(4-nitrophenylsulfonamido)thiazole-4-carboxylic acid;
5-({5-[5-(trifluoromethyl)-1,2-oxazol-3-yl]thiophen-2-yl}sulfonamido)-1,3-thiazole-4-carboxylic acid;
5-(1-benzothiophene-2-sulfonamido)-1,3-thiazole-4-carboxylic acid;
5-[(5-methylthiophen-2-yl)sulfonamido]-1,3-thiazole-4-carboxylic acid;
5-[(5-bromothiophen-2-yl)sulfonamido]-1,3-thiazole-4-carboxylic acid;
5-(1-benzothiophene-3-sulfonamido)-1,3-thiazole-4-carboxylic acid;
5-[(4-bromo-2,5-dichlorothiophen-3-yl)sulfonamido]-1,3-thiazole-4-carboxylic acid;
5-(({[(2-chlorophenyl)methyl]sulfamoyl}amino)-1,3-thiazole-4-carboxylic acid;
5-[({[3-(trifluoromethyl)phenyl]methyl}sulfamoyl)amino]-1,3-thiazole-4-carboxylic acid;
5-[(3-bromothiophen-2-yl)sulfonamido]-1,3-thiazole-4-carboxylic acid;
5-{[(2-iodophenyl)methyl]sulfonamido}-1,3-thiazole-4-carboxylic acid;
5-{[4-phenyl-5-(trifluoromethyl)thiophen-3-yl]sulfonamido}-1,3-thiazole-4-carboxylic acid;
5-{[(2,3-dichlorophenyl)methyl]sulfonamido}-1,3-thiazole-4-carboxylic acid;
5-{[(3,4-dichlorophenyl)methyl]sulfonamido}-1,3-thiazole-4-carboxylic acid;
5-[(1-phenylethyl)sulfonamido]-1,3-thiazole-4-carboxylic acid;
5-{[6-(trifluoromethyl)pyridin-3-yl]sulfonamido}-1,3-thiazole-4-carboxylic acid;
5-[(2-phenoxyethyl)sulfonamido]-1,3-thiazole-4-carboxylic acid;
5-{[2-(1,3-dioxo-2,3-dihydro-1H-isoindol-2-yl)ethyl]sulfonamido}-1,3-thiazole-4-carboxylic acid;
5-{[2-(2-chlorophenyl)ethyl]sulfonamido}-1,3-thiazole-4-carboxylic acid;
5-({1-[5-(trifluoromethyl)pyridin-2-yl]-1H-pyrazol-4-yl}sulfonamido)-1,3-thiazole-4-carboxylic acid;
5-[(2-chlorophenyl)sulfonamido]-1,3-thiazole-4-carboxylic acid;
5-(pyridine-3-sulfonamido)-1,3-thiazole-4-carboxylic acid;
5-[(2,6-dichlorophenyl)sulfonamido]-1,3-thiazole-4-carboxylic acid;
5-(cyclohexylmethyl)sulfonamido-1,3-thiazole-4-carboxylic acid;
5-[(4-methyl-3,4-dihydro-2H-1,4-benzoxazin-7-yl)sulfonamido]-1,3-thiazole-4-carboxylic acid;
5-[(1-phenylpropyl)sulfonamido]-1,3-thiazole-4-carboxylic acid;
5-{[2-(4-methoxyphenyl)ethyl]sulfonamido)-1,3-thiazole-4-carboxylic acid;
5-(2-[3-(trifluoromethyl)phenyl]ethyl})sulfonamido)-1,3-thiazole-4-carboxylic acid;
5-{[2-(4-chlorophenyl)ethyl]sulfonamido)}-1,3-thiazole-4-carboxylic acid;
5-[(piperidine-1-sulfonyl)amino]-1,3-thiazole-4-carboxylic acid;
5-[(phenylsulfamoyl)amino]-1,3-thiazole-4-carboxylic acid;
5-{[benzyl(methyl)sulfamoyl]amino}-1,3-thiazole-4-carboxylic acid;
5-[(4-acetamidophenyl)sulfonamido]-1,3-thiazole-4-carboxylic acid;
5-[(2-methoxyphenyl)sulfonamido]-1,3-thiazole-4-carboxylic acid;
5-(1,2,3,4-tetrahydronaphthalene-1-sulfonamido)-1,3-thiazole-4-carboxylic acid;
5-[(5-methyl-1-phenyl-1H-pyrazol-4-yl)sulfonamido]-1,3-thiazole-4-carboxylic acid;
5-(cyclopropylmethyl)sulfonamido-1,3-thiazole-4-carboxylic acid;
5-{[(2-methoxyphenyl)methyl]sulfonamido}-1,3-thiazole-4-carboxylic acid;
5-{[2-(2-methoxyphenyl)ethyl]sulfonamido}-1,3-thiazole-4-carboxylic acid;
5-{[2-(3-methoxyphenyl)ethyl]sulfonamido}-1,3-thiazole-4-carboxylic acid;
5-{[2-(3-chlorophenyl)ethyl]sulfonamido}-1,3-thiazole-4-carboxylic acid;
5-[(2-methanesulfonylphenyl)sulfonamido]-1,3-thiazole-4-carboxylic acid;
5-{[methyl(phenyl)sulfamoyl]amino}-1,3-thiazole-4-carboxylic acid;
5-([4-(morpholin-4-yl)phenyl]sulfonamido)-1,3-thiazole-4-carboxylic acid;

5-[(4-cyanophenyl)sulfonamido]-1,3-thiazole-4-carboxylic acid;
5-(pyridine-2-sulfonamido)-1,3-thiazole-4-carboxylic acid;
5-[(1-methyl-1H-imidazol-2-yl)sulfonamido]-1,3-thiazole-4-carboxylic acid;
5-[(6-methoxypyridin-3-yl)sulfonamido]-1,3-thiazole-4-carboxylic acid;
5-{[4-(1H-pyrazol-1-yl)phenyl]sulfonamido}-1,3-thiazole-4-carboxylic acid;
5-[(1-ethyl-5-methyl-1H-pyrazol-4-yl)sulfonamido]-1,3-thiazole-4-carboxylic acid;
5-{[(2-cyanophenyl)methyl]sulfonamido})-1,3-thiazole-4-carboxylic acid;
5-[(1-methyl-1H-pyrazol-3-yl)sulfonamido]-1,3-thiazole-4-carboxylic acid;
5-[(1-methyl-1H-pyrazol-5-yl)sulfonamido]-1,3-thiazole-4-carboxylic acid;
5-({(1-[(benzyloxy)carbonyl]piperidin-4-yl}sulfonamido)-1,3-thiazole-4-carboxylic acid;
5-[(3-phenylpropyl)sulfonamido]-1,3-thiazole-4-carboxylic acid;
5-(2,3-dihydro-1H-indene-1-sulfonamido)-1,3-thiazole-4-carboxylic acid;
5-{[4-(1-methyl-1H-pyrazol-5-yl)phenyl]sulfonamido}-1,3-thiazole-4-carboxylic acid;
5-{[2-(1,2,3,4-tetrahydroquinolin-1-yl)ethyl]sulfonamido)-1,3-thiazole-4-carboxylic acid;
5-([2-(N-phenylacetamido)ethyl]sulfonamido}-1,3-thiazole-4-carboxylic acid;
5-{[4-(3-oxomorpholin-4-yl)phenyl]sulfonamido}-1,3-thiazole-4-carboxylic acid;
5-{[4-(2-oxo-1,3-oxazolidin-3-yl)phenyl]sulfonamido}-1,3-thiazole-4-carboxylic acid;
5-[(1,2-dimethyl-1H-imidazol-4-yl)sulfonamido]-1,3-thiazole-4-carboxylic acid;
5-[(oxan-4-ylmethyl)sulfonamido]-1,3-thiazole-4-carboxylic acid;
5-[(({-[(benzyloxy)carbonyl]piperidin-4-yl}methyl)sulfonamido]-1,3-thiazole-4-carboxylic acid;
5-{([4-(2-oxopyrrolidin-1-yl)phenyl]sulfonamido}-1,3-thiazole-4-carboxylic acid;
5-({1-[6-(trifluoromethyl)pyridin-3-yl]-1H-pyrazol-4-yl}sulfonamido)-1,3-thiazole-4-carboxylic acid;
5-{[4-(1,3-oxazol-5-yl)phenyl]sulfonamido}-1,3-thiazole-4-carboxylic acid;
5-{[4-(1H-pyrazol-4-yl)phenyl]sulfonamido}-1,3-thiazole-4-carboxylic acid;
5-[(1-phenyl-1H-pyrazol-4-yl)sulfonamido]-1,3-thiazole-4-carboxylic acid;
5-{[4-(piperidin-4-yl)phenyl]sulfonamido}-1,3-thiazole-4-carboxylic acid;
5-[(4-propanamidophenyl)sulfonamido]-1,3-thiazole-4-carboxylic acid;
5-{[4-(2-hydroxyacetamido)phenyl]sulfonamido}-1,3-thiazole-4-carboxylic acid;
5-({4-[(methylcarbamoyl)amino]phenyl}sulfonamido)-1,3-thiazole-4-carboxylic acid;
5-{[(2,4-dichlorophenyl)methyl]sulfonamido}-1,3-thiazole-4-carboxylic acid;
5-{[(2-fluorophenyl)methyl]sulfonamido}-1,3-thiazole-4-carboxylic acid;
5-{[(2,3-difluorophenyl)methyl]sulfonamido)-1,3-thiazole-4-carboxylic acid;
5-{[4-(2-methoxyacetamido)phenyl]sulfonamido}-1,3-thiazole-4-carboxylic acid;
5-[(2,5-dichlorophenyl)methyl]sulfonamido}-1,3-thiazole-4-carboxylic acid;
5-{[(2,6-dichlorophenyl)methyl]sulfonamido}-1,3-thiazole-4-carboxylic acid;
5-{[(2-chloro-6-fluorophenyl)methyl]sulfonamido}-1,3-thiazole-4-carboxylic acid;
5-{[(2-chloro-4-fluorophenyl)methyl]sulfonamido})-1,3-thiazole-4-carboxylic acid;
5-{[2-chloro-5-(trifluoromethyl)phenyl]methyl}sulfonamido)-1,3-thiazole-4-carboxylic acid;
5-({4-[(dimethylamino)methyl]phenyl}sulfonamido)-1,3-thiazole-4-carboxylic acid;
5-{[(2,3,5-trichlorophenyl)methyl]sulfonamido}-1,3-thiazole-4-carboxylic acid;
5-{[(2,3-dichloro-6-fluorophenyl)methyl]sulfonamido}-1,3-thiazole-4-carboxylic acid;
5-({[2,3-dichloro-6-(trifluoromethyl)phenyl]methyl}sulfonamido)-1,3-thiazole-4-carboxylic acid;
5-{[(4-bromo-2-chlorophenyl)methyl]sulfonamido}-1,3-thiazole-4-carboxylic acid;
5-((2-[methyl(phenyl)amino]ethyl) sulfonamido)-1,3-thiazole-4-carboxylic acid;
5-{[(4-nitrophenyl)methyl]sulfonamido}-1,3-thiazole-4-carboxylic acid;
5-[6-(piperidin-1-yl)pyridin-3-ylsulfonamido]-1,3-thiazole-4-carboxylic acid;
5-[6-(methylamino)pyridin-3-ylsulfonamido]-1,3-thiazole-4-carboxylic acid;
5-[6-(4-methylpiperazin-1-yl)pyridin-3-ylsulfonamido]-1,3-thiazole-4-carboxylic acid;
5-(6-acetamidopyridin-3-ylsulfonamido)-1,3-thiazole-4-carboxylic acid;
5-({4-[(5-methyl-1,2-oxazol-3-yl)amino]phenylsulfonamido}-1,3-thiazole-4-carboxylic acid;
5-(6-aminopyridin-3-ylsulfonamido)-1,3-thiazole-4-carboxylic acid;
5-[(6-chloro-2H-1,3-benzodioxol-5-yl)methylsulfonamido]-1,3-thiazole-4-carboxylic acid;
5-{[(2-chloro-6-nitrophenyl)methyl]sulfonamido}-1,3-thiazole-4-carboxylic acid;
5-(quinoline-6-sulfonamido)-1,3-thiazole-4-carboxylic acid;
5-[(2,3-dihydroindole-1-sulfonyl)amino]-1,3-thiazole-4-carboxylic acid;
5-(4-methanesulfonylphenylsulfonamido)-1,3-thiazole-4-carboxylic acid;
5-[3-(2-oxo-1,3-oxazolidin-3-yl)phenylsulfonamido]-1,3-thiazole-4-carboxylic acid;
5-[3-(2H-pyrazol-3-yl)phenylsulfonamido]-1,3-thiazole-4-carboxylic acid;
5-[2-(pyridin-3-yl)ethylsulfonamido]-1,3-thiazole-4-carboxylic acid;
5-[3-(3-oxomorpholin-4-yl)phenylsulfonamido]-1,3-thiazole-4-carboxylic acid;
5-[3-(2-oxopyrrolidin-1-yl)phenylsulfonamido]-1,3-thiazole-4-carboxylic acid;
5-[6-(piperidin-4-ylamino)pyridin-3-ylsulfonamido]-1,3-thiazole-4-carboxylic acid;
5-(6-{[2-(dimethylamino)ethyl]amino}pyridin-3-yl sulfonamido)-1,3-thiazole-4-carboxylic acid;
5-[(4-acetamidophenyl)methylsulfonamido]-1,3-thiazole-4-carboxylic acid;
5-[6-(piperazin-1-yl)pyridin-3-ylsulfonamido]-1,3-thiazole-4-carboxylic acid;
5-[6-(4-aminopiperidin-1-yl)pyridin-3-ylsulfonamido]-1,3-thiazole-4-carboxylic acid;

5-[6-(3-aminopyrrolidin-1-yl)pyridin-3-ylsulfonamido]-1,3-thiazole-4-carboxylic acid;
5-[6-(pyrrolidin-1-yl)pyridin-3-ylsulfonamido]-1,3-thiazole-4-carboxylic acid;
5-[6-(3-aminopiperidin-1-yl)pyridin-3-ylsulfonamido]-1,3-thiazole-4-carboxylic acid;
5-[6-(1,4-diazepan-1-yl)pyridin-3-ylsulfonamido]-1,3-thiazole-4-carboxylic acid;
5-[4-(pyrrolidin-3-yloxy)phenylsulfonamido]-1,3-thiazole-4-carboxylic acid;
5-[6-(3-aminoazetidin-1-yl)pyridin-3-ylsulfonamido]-1,3-thiazole-4-carboxylic acid;
5-[6-(piperidin-4-yl)pyridin-3-ylsulfonamido]-1,3-thiazole-4-carboxylic acid;
5-[6-(1,2,3,6-tetrahydropyridin-4-yl)pyridin-3-ylsulfonamido]-1,3-thiazole-4-carboxylic acid;
5-{6-[4-(2,2,2-trifluoroethyl)piperazin-1-yl]pyridin-3-ylsulfonamido}-1,3-thiazole-4-carboxylic acid;
5-[1-(2-chlorophenyl)ethylsulfonylamino]thiazole-4-carboxylic acid;
5-[1-(2-chlorophenyl)ethylsulfonylamino]thiazole-4-carboxylic acid;
5-(3-pyridylmethylsulfonylamino)thiazole-4-carboxylic acid;
5-(isoindolin-5-ylmethylsulfonylamino)thiazole-4-carboxylic acid;
5-[[4-[(2-aminoacetyl)amino]phenyl]sulfonylamino]thiazole-4-carboxylic acid;
5-[(4-acetamido-3-fluoro-phenyl)sulfonylamino]thiazole-4-carboxylic acid;
5-[[4-[(2-hydroxy-2-methyl-propanoyl)amino]phenyl]sulfonylamino]thiazole-4-carboxylic acid;
5-[[4-[(2-hydroxy-2-phenyl-acetyl)amino]phenyl]sulfonylamino]thiazole-4-carboxylic acid;
5-[[4-[(2-hydroxy-3-phenyl-propanoyl)amino]phenyl]sulfonylamino]thiazole-4-carboxylic acid;
5-[[2-(2-hydroxyethylamino)pyrimidin-5-yl]sulfonylamino]thiazole-4-carboxylic acid (X12);
5-[(2-methylpyrimidin-5-yl)sulfonylamino]thiazole-4-carboxylic acid;
5-[[2-(4-pyridyl)pyrimidin-5-yl]sulfonylamino]thiazole-4-carboxylic acid;
5-[(6-methyl-3-pyridyl)sulfonylamino]thiazole-4-carboxylic acid; and
5-[(2-chloro-3-nitro-phenyl)methylsulfonylamino]thiazole-4-carboxylic acid;
or a salt of any of the foregoing compounds.

26. A method for reducing or removing resistance of Gram-negative bacteria to antibiotics, the method comprising administering to a patient in need of such treatment an effective amount of the compound according to claim 1.

27. A product comprising (i) the compound according to claim 1, in combination with (ii) an antibiotic agent.

28. A method for the treatment of a bacterial infection, the method comprising administering to a patient in need of such treatment an effective amount of the compound according to claim 1 and an antibiotic agent.

29. The method according to claim 28 wherein the antibiotic agent is a β-lactam antibiotic.

30. The method according to claim 29 wherein the β-lactam antibiotic is selected from carbapenems, penicillins, cephalosporins or penems.

31. The method according to claim 26 wherein the Gram-negative bacteria are bacteria which produce metallo-β-lactamases.

32. The method according to claim 26 wherein the Gram-negative bacteria are selected from Enterobacteriaceae (such as *Klebsiella pneumonia* or *Escherichia coli*), Pseudomonadaceae (such as *Pseudomonas aeruginosa* or *Burkholderia cepacia*) or *Acinetobacter baumannii*.

33. A pharmaceutical or veterinary composition comprising the compound according to claim 1 and a pharmaceutically or veterinarily acceptable excipient or carrier.

34. The pharmaceutical or veterinary composition according to claim 33, further comprising an antibiotic agent.

35. The pharmaceutical or veterinary composition according to claim 34 wherein the antibiotic agent is a β-lactam antibiotic.

36. The pharmaceutical or veterinary composition according to claim 35 wherein the β-lactam antibiotic is selected from carbapenems, penicillins, cephalosporins, oxacephems, monobactums, or penems.

\* \* \* \* \*

UNITED STATES PATENT AND TRADEMARK OFFICE
CERTIFICATE OF CORRECTION

PATENT NO. : 9,914,712 B2
APPLICATION NO. : 14/897811
DATED : March 13, 2018
INVENTOR(S) : Marc Lemonnier, David Davies and Thomas David Pallin It is certified that error appears in the above-identified patent and that said Letters Patent is hereby corrected as shown below:

In the Claims

Claim 25, Column 149, Lines 13 and 14, replace "5-{[((2-bromophenyl)methyl]sulfonamido}-1,3-thiazole-4-carboxylic acid;" with --5-{[(2-bromophenyl)methyl]sulfonamido}-1,3-thiazole-4-carboxylic acid;--

Claim 25, Column 149, Lines 59 and 60, replace "5-(({[(2-chlorophenyl)methyl]sulfamoyl}amino)-1,3-thiazole-4-carboxylic acid;" with --5-({[(2-chlorophenyl)methyl]sulfamoyl}amino)-1,3-thiazole-4-carboxylic acid;--

Claim 25, Column 150, Lines 65 and 66, replace "5-([4-(morpholin-4-yl)phenyl]sulfonamido)-1,3-thiazole-4-carboxylic acid;" with --5-{[4-(morpholin-4-yl)phenyl]sulfonamido}-1,3-thiazole-4-carboxylic acid;--

Claim 25, Column 151, Lines 19 and 20, replace "5-({(-[(benzyloxy)carbonyl]piperidin-4-yl}sulfonamido)-1,3-thiazole-4-carboxylic acid;" with --5-({1-[(benzyloxy)carbonyl]piperidin-4-yl}sulfonamido)-1,3-thiazole-4-carboxylic acid;--

Claim 25, Column 151, Lines 39 and 40, replace "5-[(({-[(benzyloxy)carbonyl]piperidin-4-yl}methyl)sulfonamido]-1,3-thiazole-4-carboxylic acid;" with --5-[({1-[(benzyloxy)carbonyl]piperidin-4-yl}methyl)sulfonamido]-1,3-thiazole-4-carboxylic acid;--

Claim 25, Column 151, Lines 63 and 64, replace "5-{[(2,3-difluorophenyl)methyl]sulfonamido)-1,3-thiazole-4-carboxylic acid;" with --5-{[(2,3-difluorophenyl)methyl]sulfonamido}-1,3-thiazole-4-carboxylic acid;--

Claim 25, Column 152, Lines 1 and 2, replace "5-[(2,5-dichlorophenyl)methyl]sulfonamido}-1,3-thiazole-4-carboxylic acid;" with --5-{[(2,5-dichlorophenyl)methyl]sulfonamido}-1,3-thiazole-4-carboxylic acid;--

Signed and Sealed this
Fifteenth Day of May, 2018

Andrei Iancu
*Director of the United States Patent and Trademark Office*

Claim 25, Column 152, Lines 7 and 8, replace "5-{[(2-chloro-4-fluorophenyl)methyl]sulfonamido})-1,3-thiazole-4-carboxylic acid;" with --5-{[(2-chloro-4-fluorophenyl)methyl]sulfonamido}-1,3-thiazole-4-carboxylic acid;--

Claim 25, Column 152, Lines 9 and 10, replace "5-{[2-chloro-5-(trifluoromethyl)phenyl]methyl}sulfonamido))-1,3-thiazole-4-carboxylic acid;" with --5-({[2-chloro-5-(trifluoromethyl)phenyl]methyl}sulfonamido)-1,3-thiazole-4-carboxylic acid;--

Claim 25, Column 152, Lines 21 and 22, replace "5-((2-[methyl(phenyl)amino]ethyl)sulfonamido)-1,3-thiazole-4-carboxylic acid;" with --5-({2-[methyl(phenyl)amino]ethyl}sulfonamido)-1,3-thiazole-4-carboxylic acid;--

Claim 25, Column 152, Lines 33 and 34, replace "5-({4-[(5-methyl-1,2-oxazol-3-yl)amino]phenylsulfonamido}-1,3-thiazole-4-carboxylic acid;" with --5-{4-[(5-methyl-1,2-oxazol-3-yl)amino]phenylsulfonamido}-1,3-thiazole-4-carboxylic acid;--

Claim 25, Column 152, Lines 59 and 60, replace "5-(6-{[2-(dimethylamino)ethyl]amino}pyridin-3-yl sulfonamido)-1,3-thiazole-4-carboxylic acid;" with --5-(6-{[2-(dimethylamino)ethyl]amino}pyridin-3-ylsulfonamido)-1,3-thiazole-4-carboxylic acid;--